United States Patent
Birnbaum et al.

(10) Patent No.: US 12,061,188 B2
(45) Date of Patent: *Aug. 13, 2024

(54) LIGAND DISCOVERY AND GENE DELIVERY VIA RETROVIRAL SURFACE DISPLAY

(71) Applicant: Massachusetts Institute of Technology, Cambridge, MA (US)

(72) Inventors: Michael Birnbaum, Arlington, MA (US); Connor Dobson, Somerville, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/458,628

(22) Filed: Aug. 30, 2023

(65) Prior Publication Data

US 2024/0044873 A1  Feb. 8, 2024

Related U.S. Application Data

(63) Continuation of application No. 16/826,665, filed on Mar. 23, 2020.

(60) Provisional application No. 62/851,889, filed on May 23, 2019.

(51) Int. Cl.
| | |
|---|---|
| *G01N 33/50* | (2006.01) |
| *C07K 14/005* | (2006.01) |
| *C07K 14/47* | (2006.01) |
| *C07K 14/54* | (2006.01) |
| *C07K 14/705* | (2006.01) |
| *C07K 14/74* | (2006.01) |
| *C07K 16/28* | (2006.01) |
| *C12N 15/86* | (2006.01) |

(52) U.S. Cl.
CPC ......... *G01N 33/505* (2013.01); *C07K 14/005* (2013.01); *C07K 14/4748* (2013.01); *C07K 14/5437* (2013.01); *C07K 14/70532* (2013.01); *C07K 14/70539* (2013.01); *C07K 16/2803* (2013.01); *C12N 15/86* (2013.01); C07K 2317/622 (2013.01); C07K 2319/02 (2013.01); C07K 2319/035 (2013.01); C07K 2319/60 (2013.01); C12N 2740/15045 (2013.01)

(58) Field of Classification Search
CPC ............ G01N 33/505; G01N 33/5047; G01N 33/5008; C07K 14/005; C07K 14/4748; C07K 14/5437; C07K 14/70532; C07K 14/70539; C07K 16/2803; C07K 2317/622; C07K 2319/02; C07K 2319/035; C07K 2319/60; C07K 14/47; C12N 15/86; C12N 2740/15045; C12N 2740/16043; C12N 2740/16045; C12N 2810/85; C12N 2810/852; C12N 2810/855; C12N 2810/859; C40B 30/04

See application file for complete search history.

(56) References Cited

U.S. PATENT DOCUMENTS

| | | | |
|---|---|---|---|
| 7,901,671 B2 | 3/2011 | Leboulch et al. | |
| 9,994,867 B2 | 6/2018 | Baltimore et al. | |
| 2008/0241929 A1* | 10/2008 | Naldini | C12N 15/86 435/456 |
| 2014/0017766 A1* | 1/2014 | Chen | C12N 15/867 435/235.1 |
| 2015/0182617 A1* | 7/2015 | Bauche | C12N 15/86 435/320.1 |
| 2015/0316511 A1 | 11/2015 | Guo | |
| 2017/0051252 A1* | 2/2017 | Morgan | A61K 39/4631 |
| 2017/0176435 A1 | 6/2017 | Seidell, III et al. | |
| 2017/0192011 A1 | 7/2017 | Birnbaum et al. | |
| 2017/0356010 A1* | 12/2017 | Frost | C07K 14/7051 |
| 2018/0201954 A1* | 7/2018 | Buchholz | A61P 37/02 |
| 2018/0362966 A1 | 12/2018 | Flechtner et al. | |
| 2019/0144885 A1* | 5/2019 | Costa Fejoz | C07K 16/2815 |
| 2020/0216502 A1* | 7/2020 | Albertini | C12N 7/00 |
| 2022/0204946 A1* | 6/2022 | Antunes Tomás | C12N 15/86 |

FOREIGN PATENT DOCUMENTS

| | | |
|---|---|---|
| WO | WO 2008/037458 A2 | 4/2008 |
| WO | WO 2012/088381 A2 | 6/2012 |
| WO | WO 2015/104376 A1 | 7/2015 |
| WO | WO 2015/112541 A2 | 7/2015 |
| WO | WO 2015/117027 A1 | 8/2015 |
| WO | WO 2017/182585 A1 | 12/2017 |
| WO | WO 2019/056015 A2 | 3/2019 |

(Continued)

OTHER PUBLICATIONS

Hastie E, Cataldi M, Marriott I, Grdzelishvili VZ. Understanding and altering cell tropism of vesicular stomatitis virus. Virus Res. Sep. 2013;176(1-2):16-32. doi: 10.1016/j.virusres.2013.06.003. Epub Jun. 22, 2013. PMID: 23796410; PMCID: PMC3865924. (Year: 2013).*

Sevier CS, Weisz OA, Davis M, Machamer CE. Efficient export of the vesicular stomatitis virus G protein from the endoplasmic reticulum requires a signal in the cytoplasmic tail that includes both tyrosine-based and di-acidic motifs. Mol Biol Cell. Jan. 2000;11(1):13-22. (Year: 2000).*

(Continued)

*Primary Examiner* — Rachel B Gill
(74) *Attorney, Agent, or Firm* — Wolf, Greenfield & Sacks, P.C.

(57) ABSTRACT

Compositions of retroviruses and methods of using the same for gene delivery, wherein the retroviruses comprise a viral envelope protein comprising at least one mutation that diminishes its native function, a non-viral membrane-bound protein comprising a membrane-bound domain and an extracellular targeting domain.

19 Claims, 25 Drawing Sheets

Specification includes a Sequence Listing.

(56) References Cited

FOREIGN PATENT DOCUMENTS

| WO | WO 2019/057974 A1 | 3/2019 | |
|---|---|---|---|
| WO | WO-2019057974 A1 * | 3/2019 | ........... C07K 14/005 |

OTHER PUBLICATIONS

Dreja H, Piechaczyk M. The effects of N-terminal insertion into VSV-G of an scFv peptide. Virol J. Sep. 2, 2006;3:69. doi: 10.1186/1743-422X-3-69. PMID: 16948856; PMCID: PMC1564393. (Year: 2006).*

Kameyama Y, Kawabe Y, Ito A, Kamihira M. Antibody-dependent gene transduction using gammaretroviral and lentiviral vectors pseudotyped with chimeric vesicular stomatitis virus glycoprotein. J Virol Methods. Oct. 2008;153(1):49-54. doi: 10.1016/j.jviromet.2008.06.013. Epub Jul. 18, 2008. PMID: 18606189. (Year: 2008).*

Yu B, Shi Q, Belk JA, Yost KE, Parker KR, Li R, Liu BB, Huang H, Lingwood D, Greenleaf WJ, Davis MM, Satpathy AT, Chang HY. Engineered cell entry links receptor biology with single-cell genomics. Cell. Dec. 22, 2022;185(26):4904-4920.e22. doi: 10.1016/j.cell.2022.11.016. Epub Dec. 13, 2022. (Year: 2022).*

Nikolic J, Belot L, Raux H, Legrand P, Gaudin Y, A Albertini A. Structural basis for the recognition of LDL-receptor family members by VSV glycoprotein. Nat Commun. Mar. 12, 2018;9(1):1029. doi: 10.1038/s41467-018-03432-4. PMID: 29531262; PMCID: PMC5847621. (Year: 2018).*

Höfig I, Barth S, Salomon M, Jagusch V, Atkinson MJ, Anastasov N, Thirion C. Systematic improvement of lentivirus transduction protocols by antibody fragments fused to VSV-G as envelope glycoprotein. Biomaterials. Apr. 2014;35(13):4204-12. doi: 10.1016/j.biomaterials.2014.01.051. Epub Feb. 12, 2014. (Year: 2014).*

Yang H, Joo KI, Ziegler L, Wang P. Cell type-specific targeting with surface-engineered lentiviral vectors co-displaying OKT3 antibody and fusogenic molecule. Pharm Res. Jun. 2009;26(6):1432-45. doi: 10.1007/s11095-009-9853-y. Epub Mar. 4, 2009. PMID: 19259792; PMCID: PMC2798122. (Year: 2009).*

Frank AM, Buchholz CJ. Surface-Engineered Lentiviral Vectors for Selective Gene Transfer into Subtypes of Lymphocytes. Mol Ther Methods Clin Dev. Oct. 17, 2018;12:19-31. doi: 10.1016/j.omtm.2018.10.006. PMID: 30417026; PMCID: PMC6216101. (Year: 2018).*

Milani M, Annoni A, Bartolaccini S, Biffi M, Russo F, Di Tomaso T, Raimondi A, Lengler J, Holmes MC, Scheiflinger F, Lombardo A, Cantore A, Naldini L. Genome editing for scalable production of alloantigen-free lentiviral vectors for in vivo gene therapy. EMBO Mol Med. Nov. 2017;9(11):1558-1573. (Year: 2017).*

Sirin S, Apgar JR, Bennett EM, Keating AE. AB-Bind: Antibody binding mutational database for computational affinity predictions. Protein Sci. Feb. 2016;25(2):393-409. Epub Nov. 6, 2015. (Year: 2015).*

Sela-Culang I, Kunik V, Ofran Y. The structural basis of antibody-antigen recognition. Front Immunol. Oct. 8, 2013;4:302. (Year: 2013).*

Chen Z, Wang J, Bao L, Guo L, Zhang W, Xue Y, Zhou H, Xiao Y, Wang J, Wu F, Deng Y, Qin C, Jin Q. Human monoclonal antibodies targeting the haemagglutinin glycoprotein can neutralize H7N9 influenza virus. Nat Commun. Mar. 30, 2015;6:6714. (Year: 2015).*

Kussie PH, Parhami-Seren B, Wysocki LJ, Margolies MN. A single engineered amino acid substitution changes antibody fine specificity. J Immunol. Jan. 1, 1994;152(1):146-52. (Year: 1994).*

Winkler K, Kramer A, Küttner G, Seifert M, Scholz C, Wessner H, Schneider-Mergener J, Höhne W. Changing the antigen binding specificity by single point mutations of an anti-p24 (HIV-1) antibody. J Immunol. Oct. 15, 2000;165(8):4505-14. (Year: 2000).*

Bowie JU, Reidhaar-Olson JF, Lim WA, Sauer RT. Deciphering the message in protein sequences: tolerance to amino acid substitutions. Science. Mar. 16, 1990;247(4948):1306-10. (Year: 1990).*

Zhang N, Huang H, Tan B, Wei Y, Xiong Q, Yan Y, Hou L, Wu N, Siwko S, et al. Leucine-rich repeat-containing G protein-coupled receptor 4 facilitates vesicular stomatitis virus infection by binding vesicular stomatitis virus glycoprotein. J Biol Chem. Oct. 6, 2017;292(40):16527-16538. Epub Aug. 23, 2017. (Year: 2017).*

Singaporean Search Report dated Sep. 15, 2023, for Application No. 11202112344V.

Invitation to Pay Additional Fees mailed Jul. 15, 2020, for Application No. PCT/US2020/024175.

International Search Report and Written Opinion mailed Sep. 14, 2020, for Application No. PCT/US2020/024175.

International Preliminary Report on Patentability mailed Dec. 2, 2021, for Application No. PCT/US2020/024175.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Bentzen et al., Evolution of MHC-based technologies used for detection of antigen-responsive T cells. Cancer Immunol Immunother. Mar. 17, 2017;66:657-66.

Buchholz et al., Retroviral display and high throughput screening. Comb Chem High Throughput Screen. Feb. 2008;11(2):99-110.

Cire et al., Immunization of mice with lentiviral vectors targeted to MHC class II+ cells is due to preferential transduction of dendritic cells in vivo. PLoS One. Jul. 24, 2014;9(7):e101644.

Frank et al., Surface-Engineered Lentiviral Vectors for Selective Gene Transfer into Subtypes of Lymphocytes. Mol Ther Methods Clin Dev. Oct. 17, 2018;12:19-31.

Funke et al., Targeted Cell Entry of Lentiviral Vectors. Mol Ther. Aug. 2008;16(8):1427-36.

Grubaugh et al., Proteins as T cell antigens: methods for high-throughput identification. Vaccine. Aug. 20, 2013;31(37).

Guideng et al., T cell antigen discovery via trogocytosis. Nature Methods. Feb. 2019;16(2):183-90.

Hastie et al., Understanding and altering cell tropism of vesicular stomatitis virus. Virus Res. Sep. 2013;176(1-2):16-32. doi: 10.1016/j.virusres.2013.06.003. Epub Jun. 22, 2013.

Joglekar et al., T cell antigen discovery via signaling and antigen-presenting bifunctional receptors. Nature Methods. Sep. 23, 2019;16(2):191-8.

Karlin et al., Applications and statistics for multiple high-scoring segments in molecular sequences. Proc Natl Acad Sci U S A. Jun. 15, 1993;90(12):5873-7.

Karlin et al., Methods for assessing the statistical significance of molecular sequence features by using general scoring schemes. Proc Natl Acad Sci U S A. Mar. 1990;87(6):2264-8.

Nikolic et al., Structural basis for the recognition of LDL-receptor family members by VSV glycoprotein. Nat Commun. Mar. 12, 2018;9:1029.

Ou et al., Specific targeting of human interleukin (IL)-13 receptor α2-positive cells with lentiviral vectors displaying IL-13. Hum Gene Ther Methods. Apr. 2012;23(2):137-47. doi: 10.1089/hgtb.2012.054. Epub May 21, 2012.

Sevier et al., Efficient export of the vesicular stomatitis virus G protein from the endoplasmic reticulum requires a signal in the cytoplasmic tail that includes both tyrosine-based and di-acidic motifs. Mol Biol Cell. Jan. 2000;11(1):13-22.

Taube et al., Lentivirus display: stable expression of human antibodies on the surface of human cells and virus particles. PLoS One. Sep. 11, 2008;3(9):e3181.

Urban et al., Retroviral display in gene therapy, protein engineering, and vaccine development. ACS Chem Biol. Jan. 21, 2011;6(1):61-74. doi: 10.1021/cb100285n. Epub Dec. 20, 2010.

Urban et al., Selection of functional human antibodies from retroviral display libraries. Nucleic Acids Res. Feb. 24, 2005;33(4):e35.

Yang et al., Cell type-specific targeting with surface-engineered lentiviral vectors co-displaying OKT3 antibody and fusogenic molecule. Pharm Res. Jun. 2009;26(6):1432-45. doi: 10.1007/s11095-009-9853-y. Epub Mar. 4, 2009.

Yang et al., Targeting lentiviral vectors to specific cell types in vivo. PNAS. Aug. 1, 2006;103(31):11479-84.

(56) References Cited

OTHER PUBLICATIONS

Chan et al., Conjugation of lentivirus to paramagnetic particles via nonviral proteins allows efficient concentration and infection of primary acute myeloid leukemia cells. J Virol. Oct. 2005;79(20):13190-4.

Goyvaerts et al., Targeting of human antigen-presenting cell subsets. J Virol. Oct. 2013;87(20):11304-8. doi: 10.1128/JVI.01498-13. Epub Jul. 17, 2013.

Goyvaerts et al., Development of the Nanobody display technology to target lentiviral vectors to antigen-presenting cells. Gene Ther. Dec. 2012;19(12):1133-40. doi: 10.1038/gt.2011.206. Epub Jan. 12, 2012.

Peach et al., Both extracellular immunoglobin-like domains of CD80 contain residues critical for binding T cell surface receptors CTLA-4 and CD28. J Biol Chem. Sep. 8, 1995;270(36):21181-7.

Zhang et al., Cell-specific targeting of lentiviral vectors mediated by fusion proteins derived from Sindbis virus, vesicular stomatitis virus, or avian sarcoma/leukosis virus. Retrovirology. Jan. 25, 2010;7:3.

\* cited by examiner

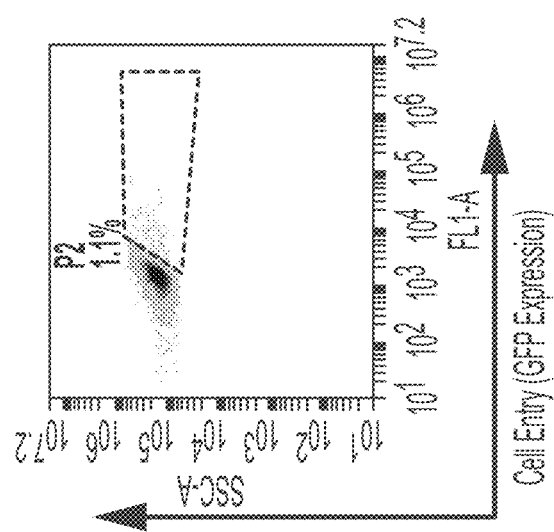
FIG. 3B
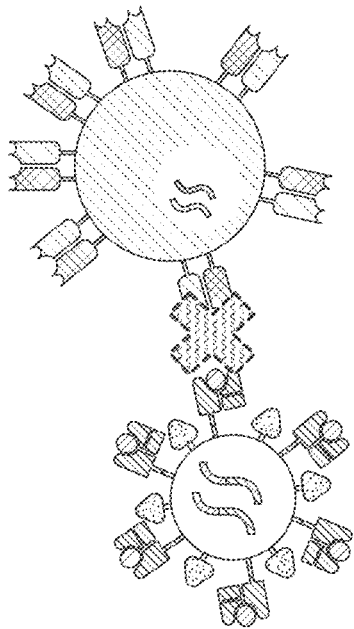
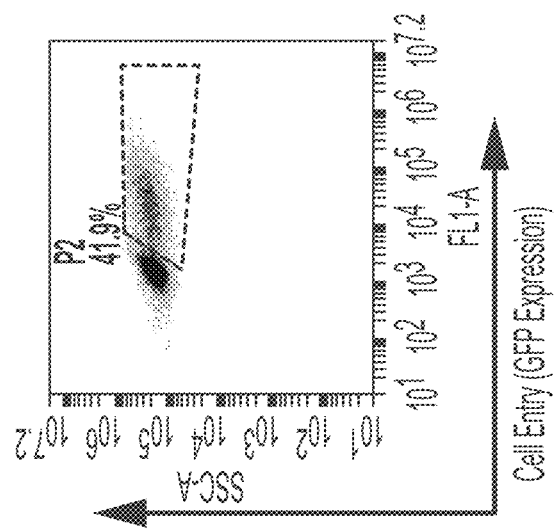
FIG. 3A
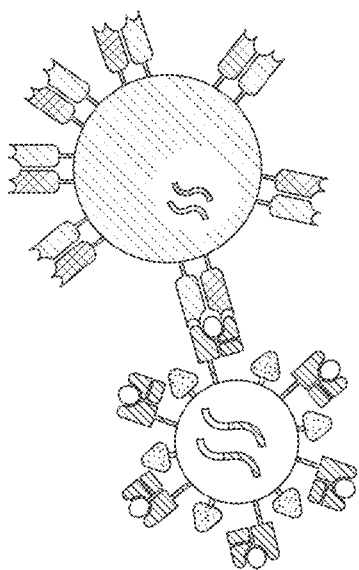

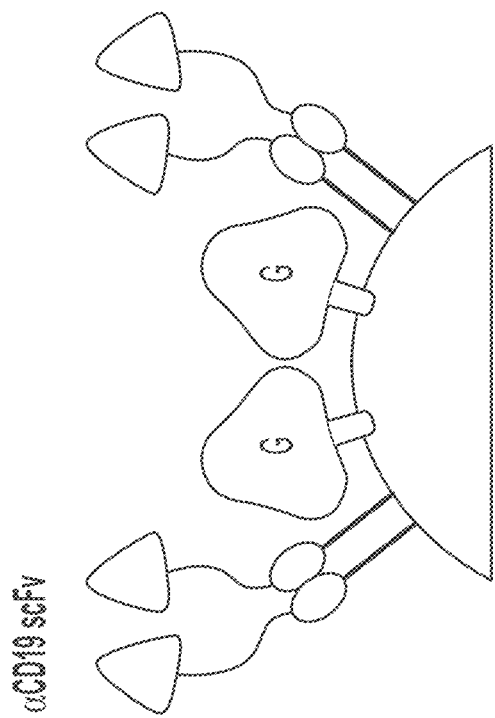

LIGAND DISCOVERY AND GENE DELIVERY VIA RETROVIRAL SURFACE DISPLAY

RELATED APPLICATIONS

This application is a continuation of U.S. application Ser. No. 16/826,665, filed Mar. 23, 2020, entitled "LIGAND DISCOVER AND GENE DELIVERY VIA RETROVIAL SURFACE DISPLAY," which claims the benefit under 35 U.S.C. § 119(e) of the filing date of U.S. Provisional Application Ser. No. 62/851,889, entitled "LIGAND DISCOVERY AND GENE DELIVERY VIA RETROVIRAL SURFACE DISPLAY" and filed on May 23, 2019, the entire contents of each of which are incorporated herein by reference.

GOVERNMENT SUPPORT

This invention was made with government support under CA014051 awarded by the National Institutes of Health, and W81XWH-18-1-0208 awarded by the Army Medical Research and Development Command. The government has certain rights in the invention.

REFERENCE TO AN ELECTRONIC SEQUENCE LISTING

The contents of the electronic sequence listing (M065670463US02-SUBSEQ-HCL.xml; Size: 106,673 bytes; and Date of Creation: Feb. 23, 2024) is herein incorporated by reference in its entirety.

BACKGROUND

It has been well established that retroviruses (e.g., lentiviruses) can have their natural tropism redirected to targets of interest via pseudotyping a virus to express the envelope protein of a different virus. This is most commonly accomplished via pseudotyping with the VSV glycoprotein, which targets the LDL receptor and therefore enables viral entry into a wide range of cells. Recently, groups have shown that if lentiviruses are pseudotyped with envelope proteins from paramyxoviruses such as measles virus or nipah virus, and if mutations are created that abolish native tropism, C-terminal fusions to these viruses allow receptor-mediated entry to the target cell of choice.

SUMMARY

Herein, the inventors have surprisingly demonstrated that a combination of mutations to abolish native function (e.g., tropism) and overexpression of a second membrane protein allows for that second protein to function as the basis for viral entry. These discoveries, as described herein, enable new and innovative methodologies, for example, to screen of cells that are notoriously challenging to screen for specific antigens and function (e.g., T cells), and to deliver nucleic acids to target cells in a target-specific manner.

Some aspects of the disclosure provide compositions of a retrovirus (e.g., a lentivirus) comprising (i) a nucleic acid comprising a non-viral membrane-bound protein comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter; and (ii) a mutated viral envelope protein comprising at least one mutation that diminishes its native function.

Some aspects of the disclosure provide compositions of a retrovirus (e.g., a lentivirus), comprising (i) a CD80 protein domain; and (ii) a mutated viral envelope protein comprising at least one mutation that diminishes its native function. The CD80 protein domain may be an extracellular domain. In some embodiments, the CD80 extracellular domain binds to a receptor on a target cell.

Some aspects of the disclosure provide methods of screening a population of cells, the method comprising (i) providing a retrovirus (e.g., a lentivirus) comprising a viral envelope protein comprising at least one mutation that diminishes its native function, a non-viral membrane-bound protein comprising a membrane-bound domain and an extracellular targeting domain, and a nucleic acid encoding a reporter; (ii) combining the retrovirus with a population of cells; and (iii) sorting the population of cells based on the presence or absence of the reporter. In some embodiments, the retrovirus (e.g., a lentivirus) comprises a nucleic acid comprising a non-viral membrane-bound protein comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter.

In some embodiments, the cells are somatic cells (e.g., antigen-specific cells, e.g., T cells or B cells). In some embodiments, the cells are isolated from a subject (e.g., a human subject). In some embodiments, the cells are isolated from the blood or a tumor of a subject. In some embodiments, the cells are maintained in liquid culture prior to being combined with the retrovirus.

In some embodiments, the viral envelope protein is a VSV-G envelope protein, a measles virus envelope protein, a nipah virus envelope protein, or a cocal virus G protein. A VSV-G envelope protein may be a mutated at one or more of any one of H8, K47, Y209, and/or R354. A measles virus envelope protein may be a mutated at one or more of any one of Y481, R533, S548, and/or F549. A nipah virus envelope protein may be a mutated at one or more of any one of E501, W504, Q530, and/or E533. A cocal virus G protein may be a mutated at K64 and/or R371.

In some embodiments, the non-viral membrane-bound protein comprises a Major Histocompatibility Complex (MHC) protein. In some embodiments, the extracellular targeting domain is a protein (e.g., interleukin-13), a peptide, or an antibody (e.g., anti-CD19 antibody, an anti-TCR antibody, or an anti-CD3 antibody). In some embodiments, the reporter is a fluorescent protein (e.g., green fluorescent protein, yellow fluorescent protein, red fluorescent protein) or an antibiotic resistance marker. In some embodiments, a linker is positioned between the membrane-bound domain and the extracellular targeting domain. A linker may be a rigid linker (e.g., a PDGFR stalk or a CD8a stalk), a flexible linker (e.g., comprising an amino acid sequence comprising GAPGAS (SEQ ID NO: 5) or GGGGS (SEQ ID NO: 7)), or an oligomerized linker (e.g., an IgG4 hinge or an amino acid sequence that can form a tetrameric coiled coil).

In some embodiments, the retrovirus is combined with the population of cells in (ii) for one minute to seventy-two hours and at a temperature ranging from 4° C. to 42° C. In some embodiments, the retrovirus and the population of cells are combined in (ii) in the presence of (a) a cell culture media, optionally RPMI or DMEM cell culture media; (b) a buffered saline solution, optionally phosphate-buffered saline or HEPES-buffered saline; and/or (c) an enhancer of retroviral transduction, optionally heparin sulfate, polybrene, protamine sulfate, and/or dextran. In some embodiments, the extracellular targeting domain is capable of binding to a cognate protein (e.g., a protein receptor) that is present on the cell surface of a subset of the population of cells. In some embodiments, the population of cells is washed between (ii) and (iii) (e.g., using phosphate-buffered saline (PBS), e.g., to remove the retrovirus from the population of cells). In some embodiments, sorting the population of cells is performed using fluorescence-activated cell sorting, single-cell next-generation sequencing, or antibiotic selection.

In some embodiments, the methods further comprise a second retrovirus, wherein the second retrovirus comprises a different extracellular targeting domain and/or a different reporter compared to the first retrovirus.

Other aspects of the disclosure provide methods of delivering a nucleic acid (e.g., a gene of interest, e.g., that encodes a protein) to an cell, the method comprising (i) providing a retrovirus comprising the nucleic acid, a viral envelope protein comprising at least one mutation that diminishes its native function, and a non-viral membrane-bound protein comprising an extracellular targeting domain that is capable of binding to a cognate ligand of the cell; and (ii) contacting the retrovirus with the cell, thereby delivering the nucleic acid to the cell. In some embodiments, the retrovirus enters or infects the cell during (ii).

Some aspects of the disclosure provide methods of delivering a nucleic acid to a cell, the method comprising (i) providing a retrovirus comprising the nucleic acid, a viral envelope protein comprising at least one mutation that diminishes its native function, and a CD80 protein domain; and (ii) contacting the retrovirus with the cell, thereby delivering the nucleic acid to the cell.

Yet other aspects of the disclosure provide methods of detecting an interaction between a retrovirus and an cell, the method comprising: (i) contacting a sample comprising the retrovirus and an cell with an antibody, wherein the retrovirus comprises a viral envelope protein comprising at least one mutation that diminishes its native function, a non-viral membrane-bound protein comprising an extracellular targeting domain, and wherein the antibody binds to the extracellular targeting domain of the retrovirus; (ii) optionally removing unbound antibody from the sample; and (iii) imaging the sample to detect whether the antibody-retrovirus complex is bound to the cell.

In some embodiments, the antibody further comprises a fluorescent label, optionally wherein the antibody is covalently linked to a fluorescent label. In some embodiments, the sample is imaged in (iii) using confocal or fluorescence microscopy.

Some aspects of the disclosure provide libraries of retroviruses, comprising a plurality of unique retroviruses, wherein each unique retrovirus comprises a viral envelope protein comprising at least one mutation that diminishes its native function, a non-viral membrane-bound protein comprising a membrane-bound domain and an extracellular targeting domain (e.g., comprising at least 5, at least 10, at least 15, at least 20, or at least 50 amino acids), and a nucleic acid encoding a reporter, and wherein each unique retrovirus comprises a different and unique extracellular targeting domain.

In some embodiments, a library is capable of being screened against a population of antigen-specific cells, optionally wherein the antigen-specific cells are B cells or T cells. A library may comprise at least $10^2$, at least $10^3$, at least $10^4$, at least $10^5$, at least $10^6$, at least $10^7$, at least $10^8$, at least $10^9$, or at least $10^{10}$ unique retroviruses. In some embodiments, each different and unique extracellular targeting domain is generated through site-directed mutagenesis.

Some aspects of the disclosure provide populations of cells, wherein a subset of the population of cells contain a retrovirus comprising: a viral envelope protein comprising at least one mutation that diminishes its native function, a non-viral membrane-bound protein comprising a membrane-bound domain and an extracellular targeting domain, and a nucleic acid encoding a reporter. In some embodiments, a subset of the population of cells (e.g., antigen-specific cells, e.g., B cells or T cells) contains a retrovirus as described herein. In some embodiments, the subset of the population of cells contains a retrovirus inside each cell of the subset. The subset of the population that contain the retrovirus may be isolated and/or sorted from the cells of the population that do not contain the retrovirus.

BRIEF DESCRIPTION OF THE DRAWINGS

FIG. 1 depicts an exemplary schematic of a retrovirus of the current invention interacting with a cognate ligand of a target cell.

FIG. 2 depicts an exemplary schematic of a protein comprising a signal sequence (SP), an extracellular targeting domain (peptide), a membrane-bound domain (MHC), an internal ribosome entry site (IRES), and a reporter (GFP); and the ability of a retrovirus comprising said protein to interact with a target cell.

FIGS. 3A-3B depict graphs showing retroviral entry into a target cell. FIG. 3A demonstrates that the binding interaction of an extracellular targeting domain present in a retrovirus to a cognate ligand of a target cell leads to entry of the retrovirus and subsequent expression of reporter (GFP). FIG. 3B demonstrates that contacting a retrovirus with a non-target cell does not lead to entry of the retrovirus.

FIG. 4 depicts graphs showing the ability of retroviral entry into target cells at variable affinities between an extracellular targeting domain and its cognate ligand.

FIGS. 5A-5B depict graphs showing that T cell signaling is active during retroviral entry or infection. FIG. 5A demonstrates that the binding interaction of an extracellular targeting domain present in a retrovirus to a cognate ligand of a target cell leads to entry of the retrovirus and T cell signaling activation. FIG. 5B demonstrates that contacting a retrovirus with a non-target cell does not lead to entry of the retrovirus or T cell signaling activation.

FIG. 6 depicts an exemplary schematic of a pMHC retroviral library screening methodology.

FIGS. 7A-7B depict graphs showing retroviral entry into a target cell. FIG. 7A demonstrates that the binding interaction of an interleuken-13 (IL-13) protein domain present in a retrovirus to an IL-13 protein receptor of a target cell leads to entry of the retrovirus and subsequent expression of reporter (GFP). FIG. 7B demonstrates that contacting a retrovirus comprising an IL-13 protein domain with a non-target cell that does not express an IL-13 protein receptor does not lead to entry of the retrovirus.

FIG. 8 depicts three exemplary retroviruses, each comprising a different viral envelope protein.

FIG. 9 depicts the ability of a retrovirus comprising a Nipah viral envelope protein and an anti-CD19 scFv antibody to infect and enter CD19+ Raji cells.

FIGS. 10A-10B depict the ability of a retrovirus comprising a mutated VSV-G viral envelope protein and an anti-CD19 scFv antibody to infect and enter $CD19^+$ Raji cells, while not infecting $CD19^-$ Jurkat cells. A retrovirus comprising a wild-type VSV-G viral envelope protein and an anti-CD19 scFv antibody infects both CD19+ Raji cells and CD19− Jurkat cells.

FIG. 11 depicts exemplary linkers for use in nucleic acids and proteins comprising membrane-bound and extracellular targeting domains.

FIG. 12 depicts graphs showing the effect of short protein linkers (PDGFR; GAPGAS (SEQ ID NO: 5); CAR ECD; top, left to right) and long protein linkers (CD8a; Hinge domain; tetrameric coiled coil; bottom, left to right) on retroviral entry.

Figure 16A:
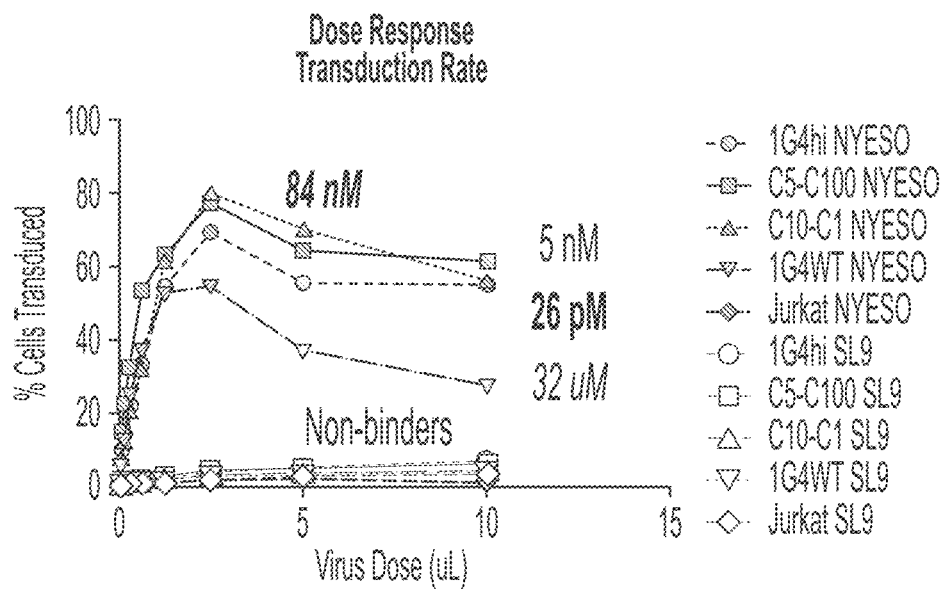
Figure 16B:
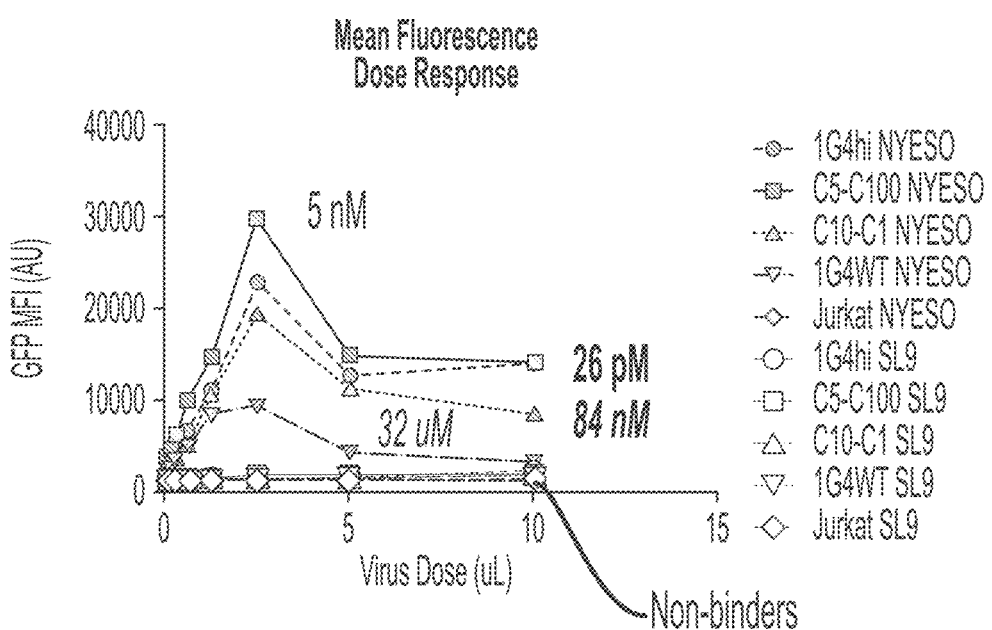

FIGS. 16A-16B depict graphs demonstrating the ability of retroviral entry into target cells at varying concentrations of virus. FIG. 16A shows the ability of NYESO-1 displaying lentiviruses to transduce IG4-expressing T cells. SL-1 displaying lentiviruses do not transduce IG4-expressing T cells. FIG. 16B shows the mean fluorescence provided by the interaction between NYESO-1 displaying lentiviruses and IG4-expressing T cells.

Figures 17, 18A:
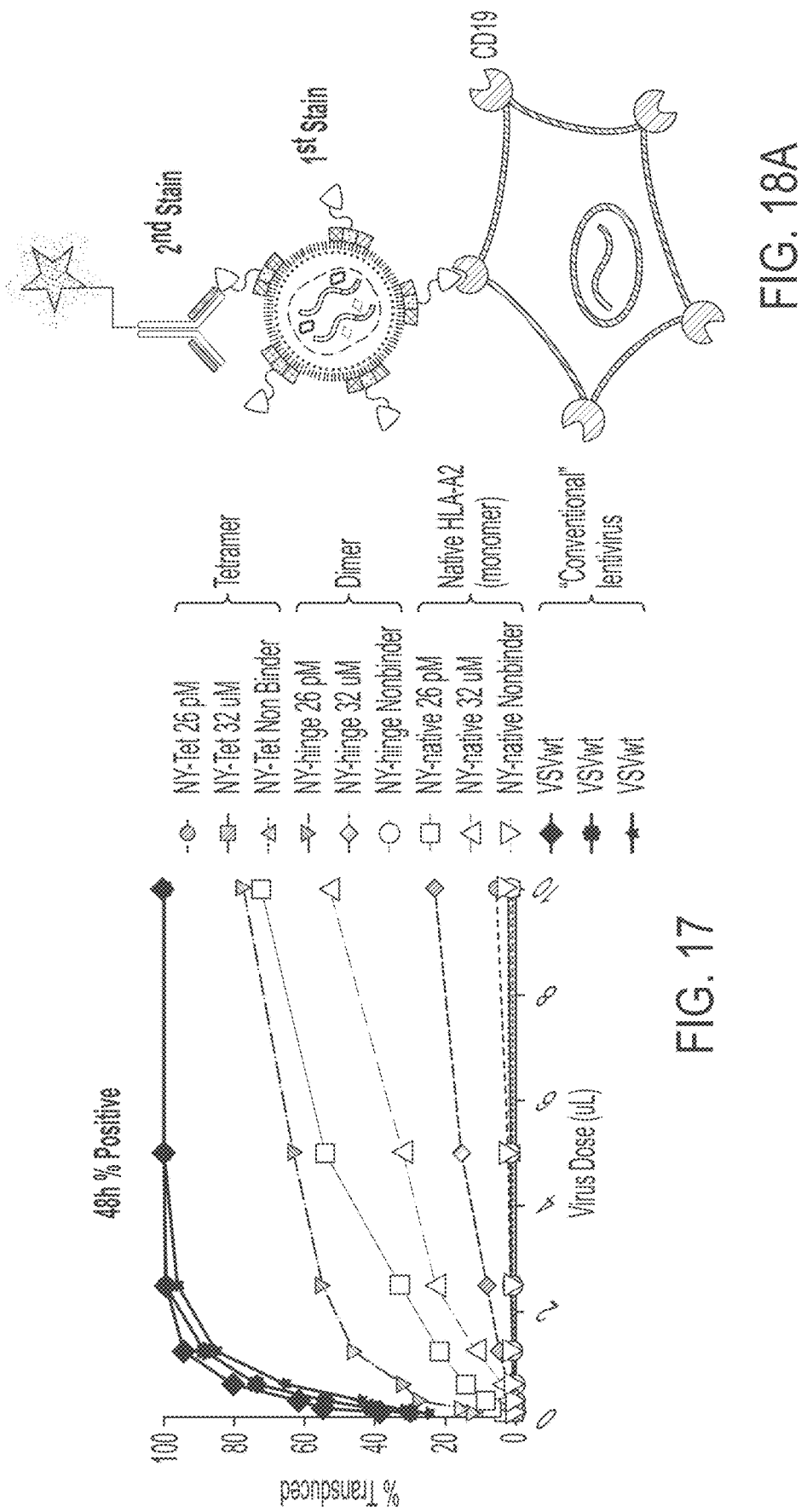

FIG. 17 depicts a graph that demonstrates the impact of protein linker oligomerization on retroviral transduction.

Figure 18B:
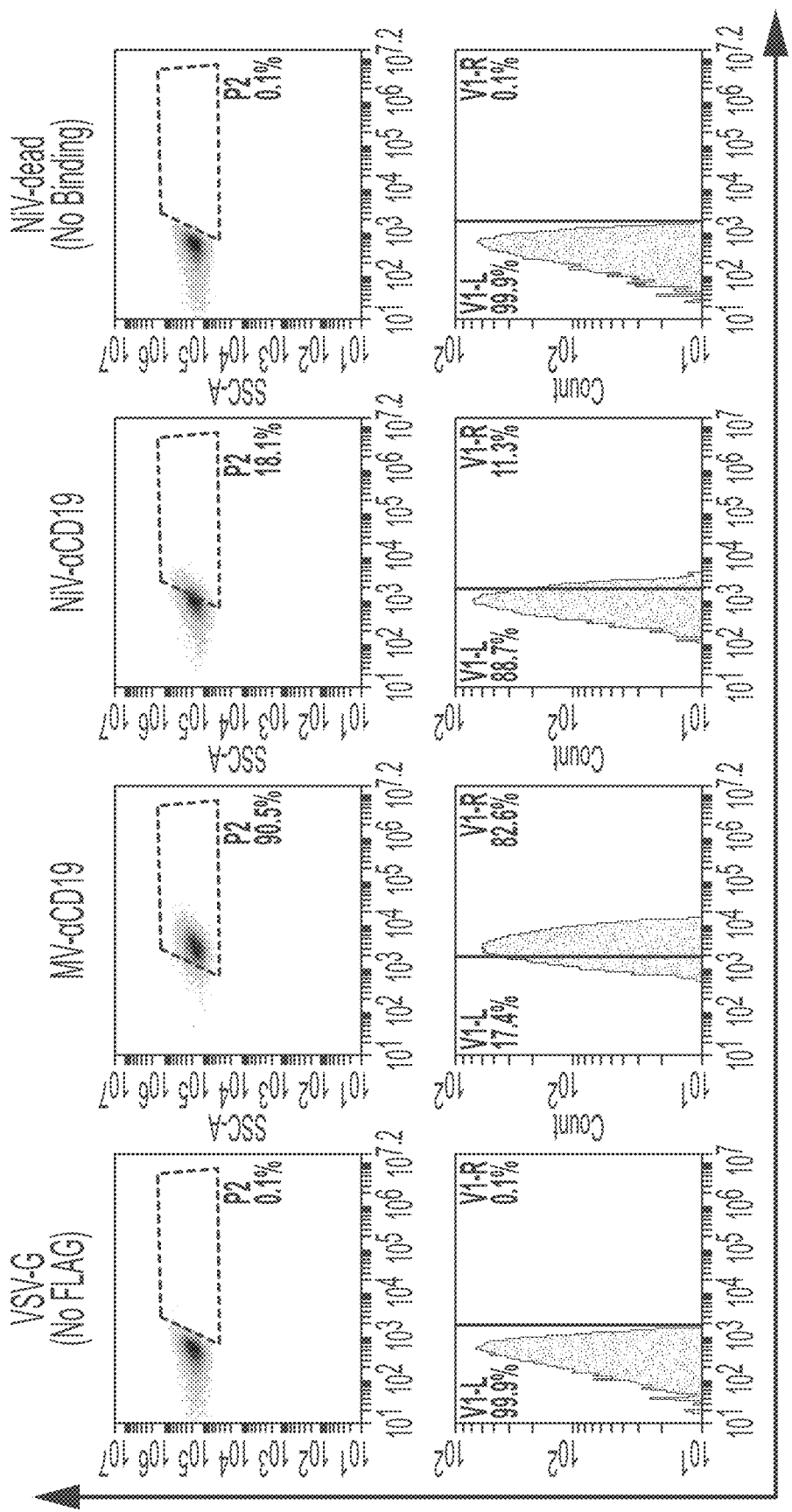

FIGS. 18A-18B depict the ability to detect a binding interaction between a retrovirus comprising an anti-CD19 scFv antibody and a target cell comprising CD19 using a fluorescently labeled antibody that binds to the retrovirus. FIG. 18A depicts an exemplary binding schematic. FIG. 18B depicts graphs showing ability of retroviral constructs to interact with a target cell.

Figure 19:
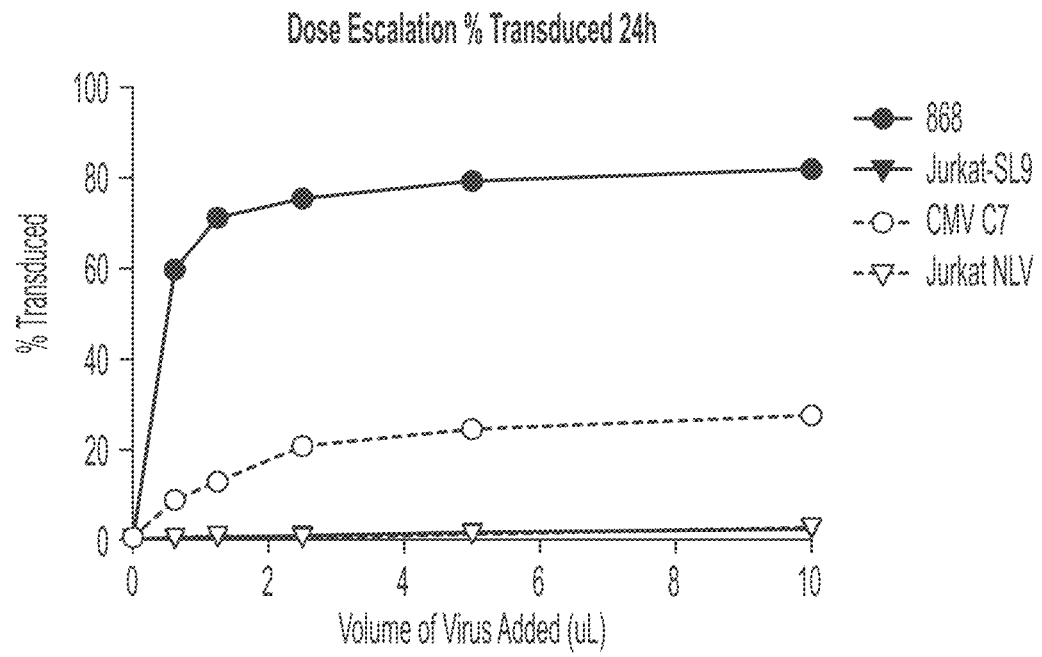

FIG. 19 depicts the ability of SL9 peptide displaying lentiviruses to transduce 868 TCR-expressing T cells ('868') and the ability of CMV NLV peptide displaying lentiviruses to transduce C7 TCR-expressing T cells ('CMV C7').

Figure 20:
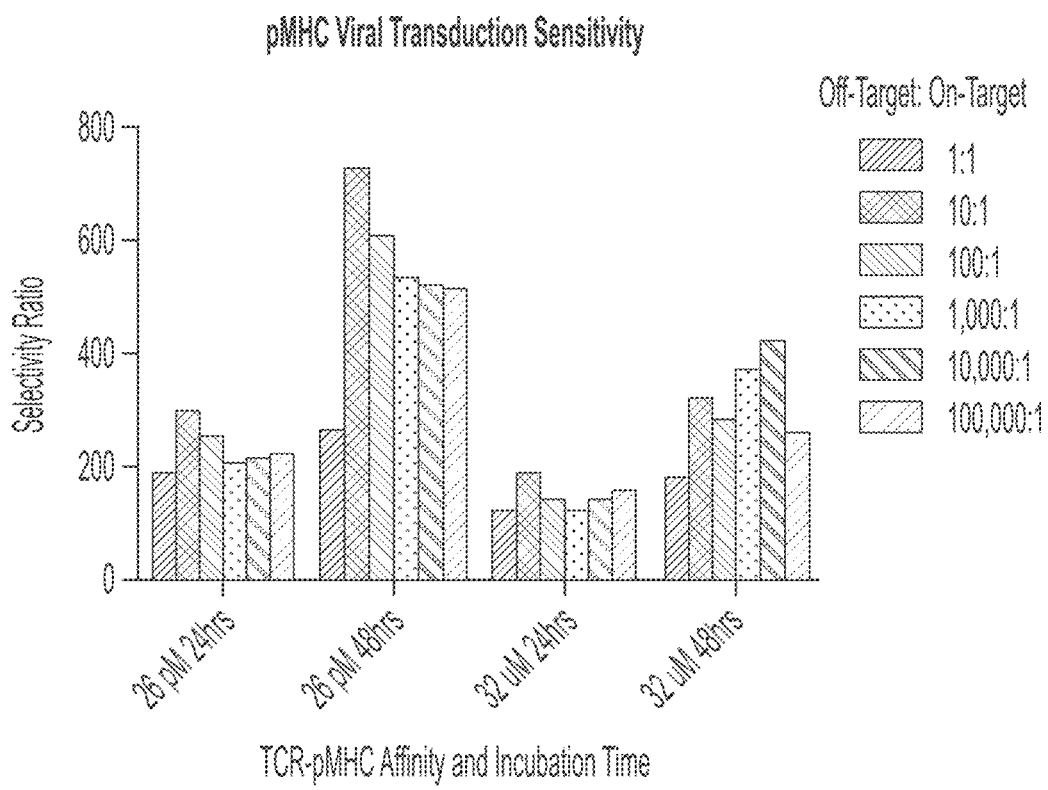

FIG. 20 depicts the ability of NYESO-1 displaying lentiviruses to selectively transduce T cells (target cells) expressing an IG4 T cell receptor (TCR) variant (binding affinities of ~26 PM or ~32 µM for NYESO-1) relative to cells not expressing an IG4 TCR (off-target) at ratios of off-target cells to target cells as high as 100,000:1.

Figure 21:
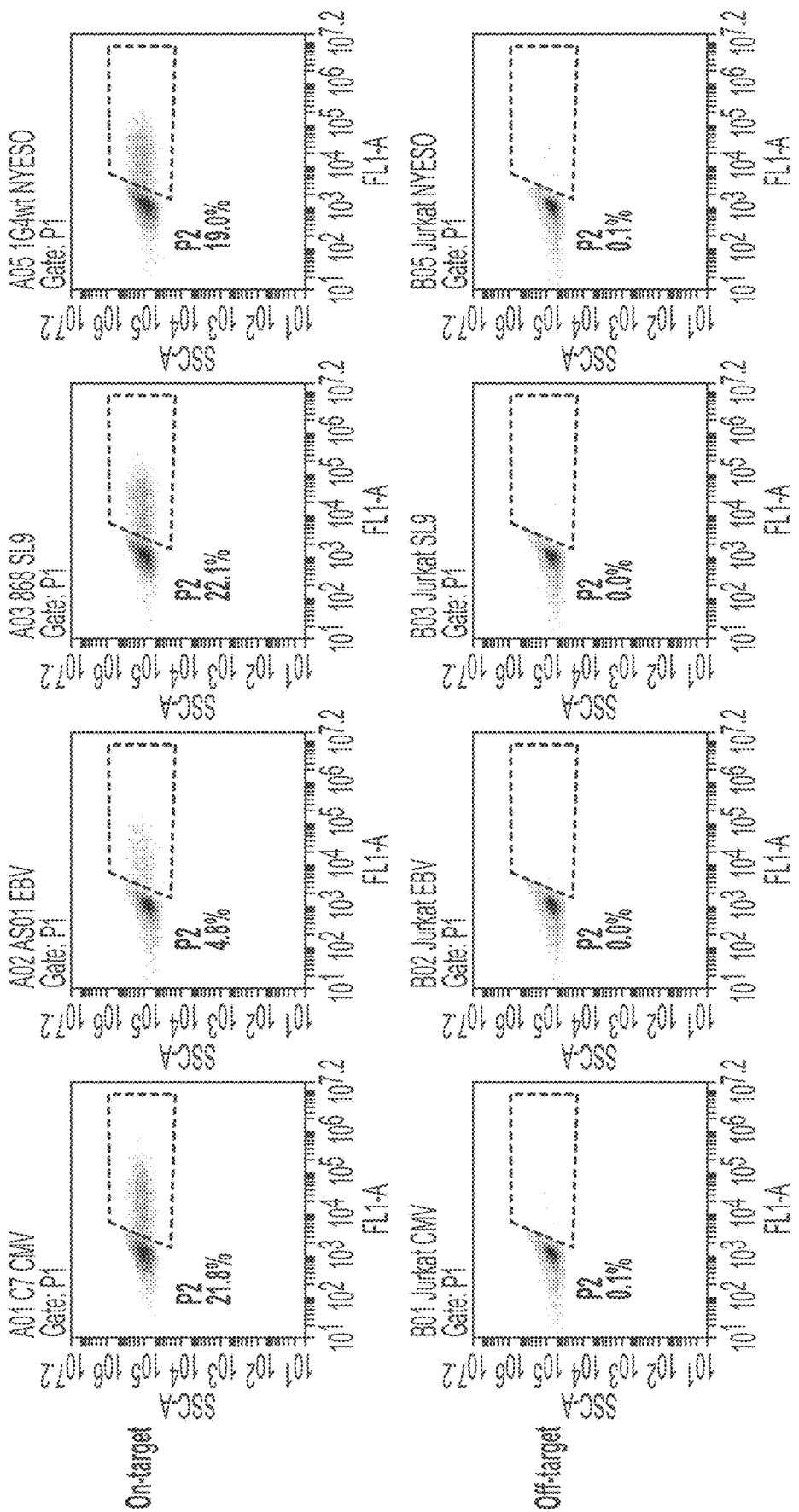

FIG. 21 depicts the ability of lentiviruses displaying varying targeting peptides (CMV NLV; EBV; SL9; GL9; NYESO-1) to selectively transduce T cells that express targeting peptide-specific TCRs (on-target) relative to T cells that do not express the targeting peptide-specific TCRs (off-target).

Figure 22A:
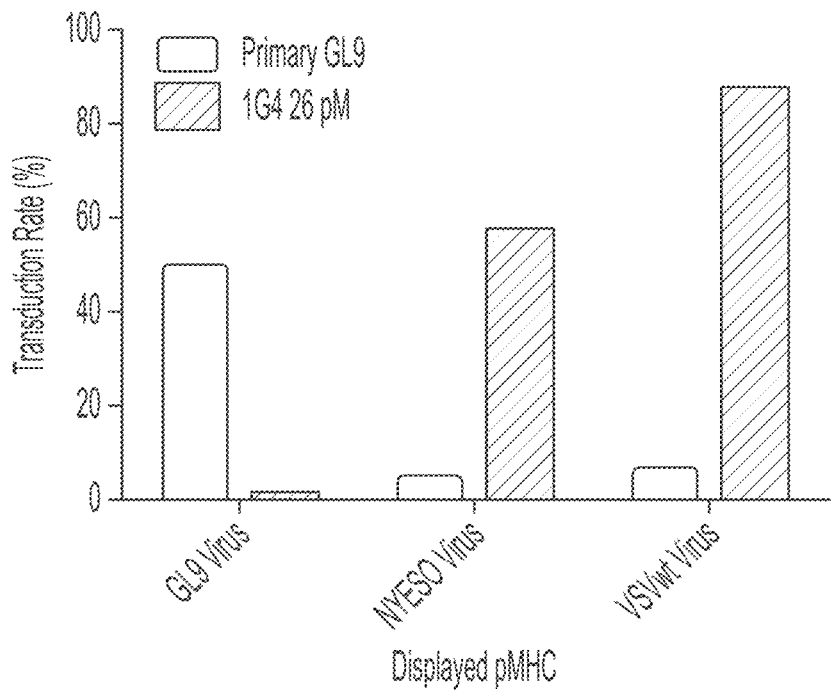
Figure 22B:
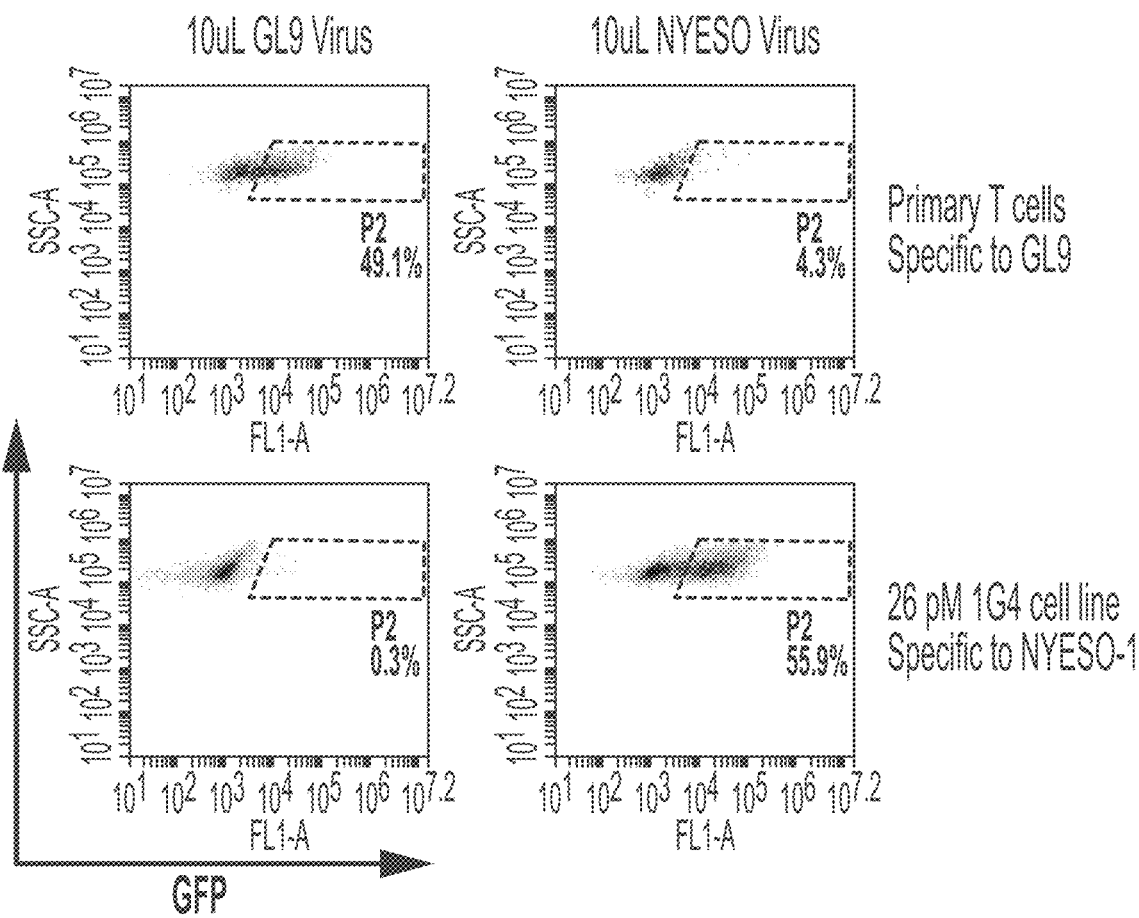

FIGS. 22A-22B depict the ability of varying lentiviruses (GL9 peptide targeting; NYESO-1 peptide targeting; wild-type VSV) to transduce primary T cells that express GL9-specific TCRs and T cells that express an IG4 TCR variant. FIG. 22A depicts the transduction rate for each lentivirus. FIG. 22B depicts graphs showing FACS data for GL9 virus and NYESO-1 virus.

Figure 23:
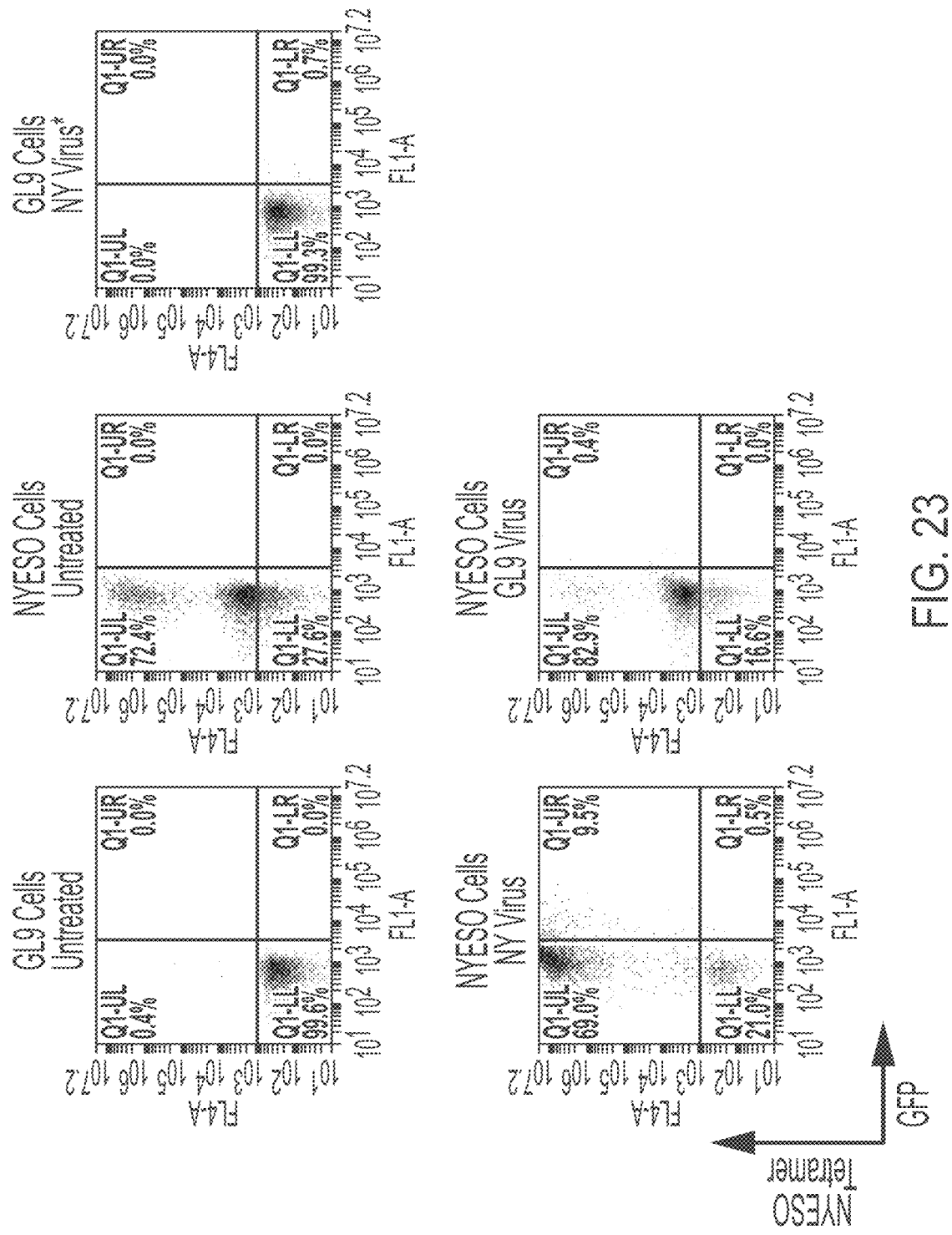

FIG. 23 depicts graphs showing that primary NYESO-1-reactive cells are specifically infected.

Figure 24:
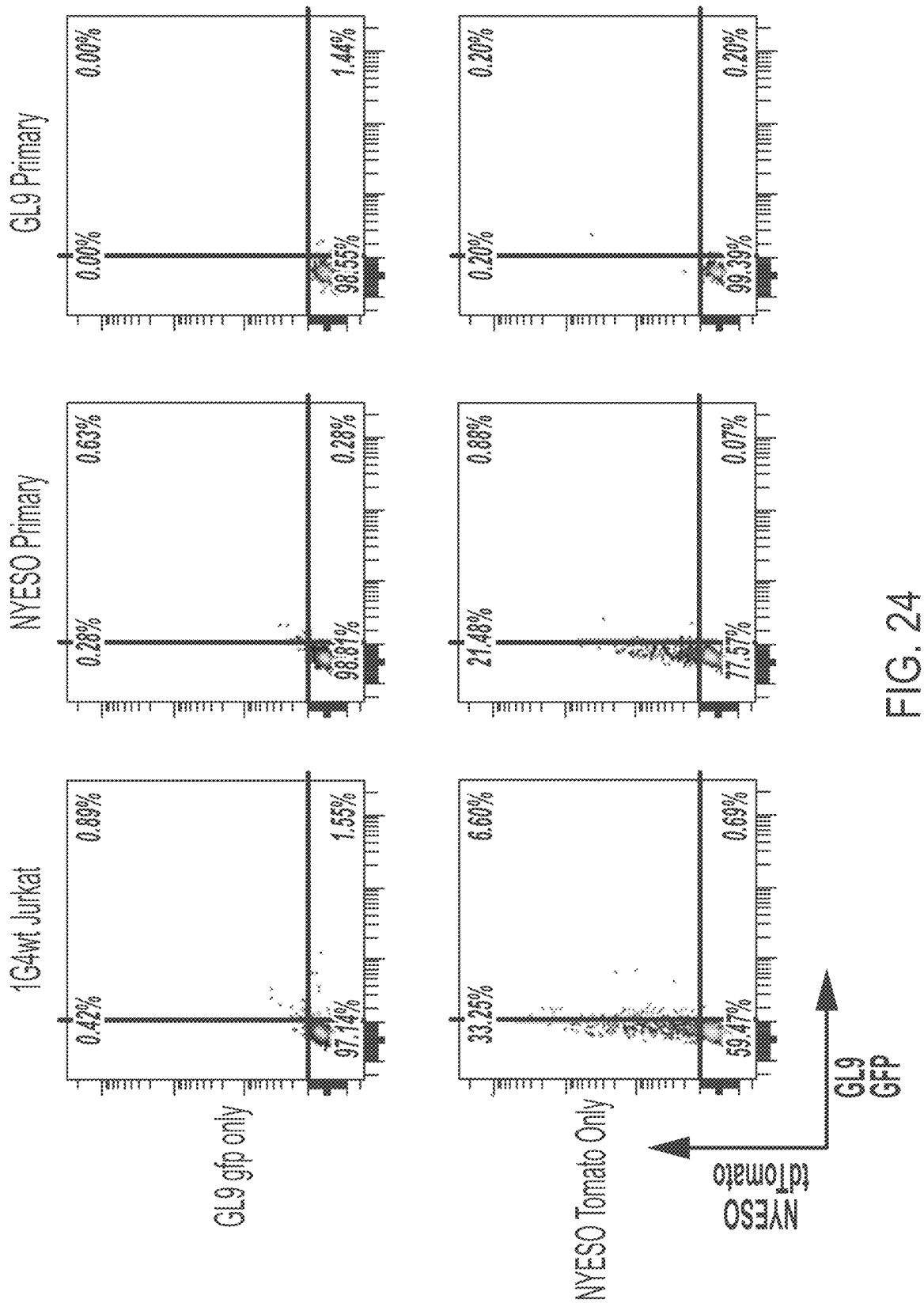

FIG. 24 depicts graphs showing that NYESO-1 targeted virus specifically infects expanded primary cells.

Figure 25:
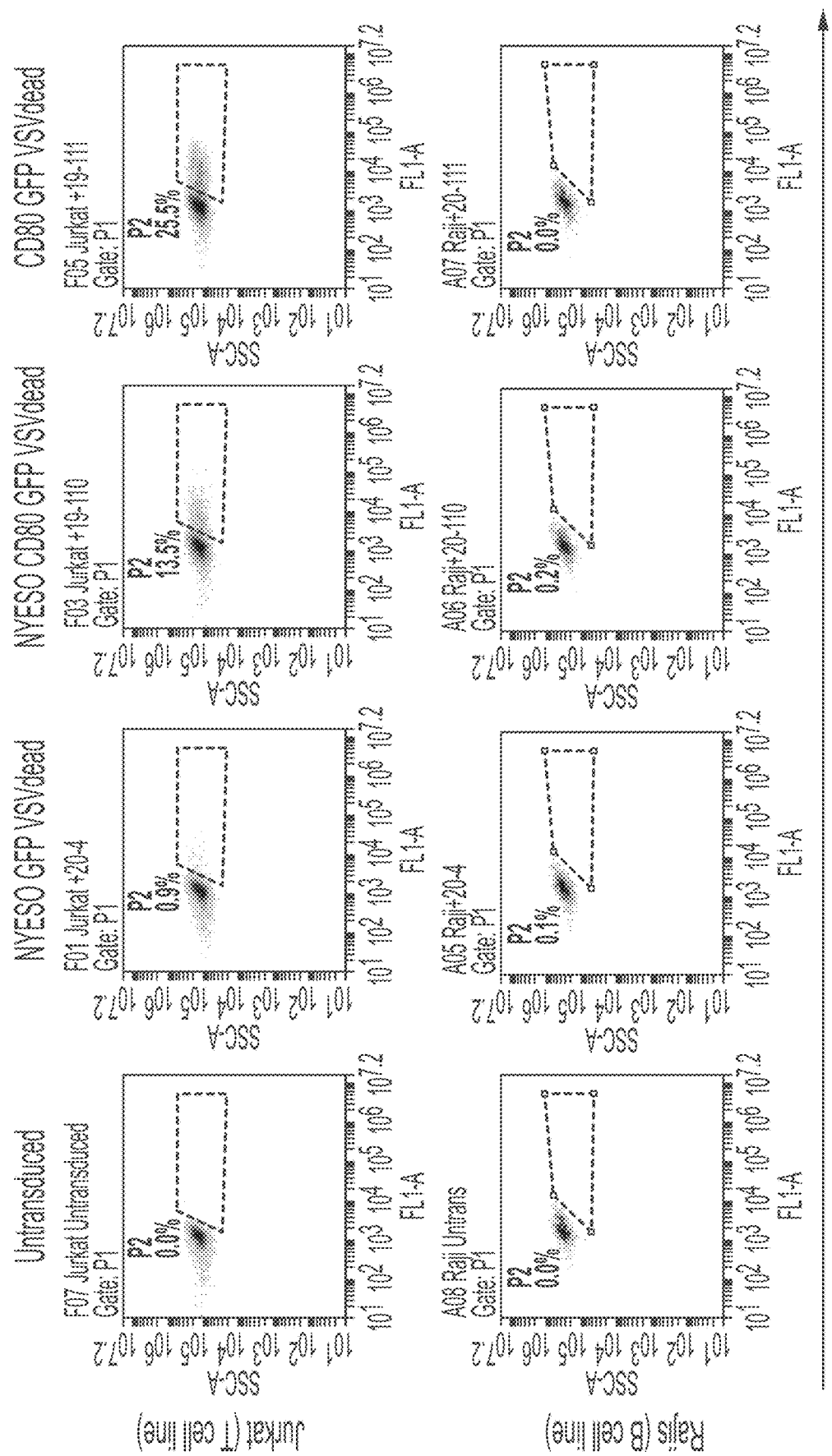

FIG. 25 depicts graphs showing the ability of a retrovirus comprising a mutated VSV-G viral envelope protein and a CD80 domain to specifically infect Jurkat T cells, relative to a B cell line.

Figure 26:
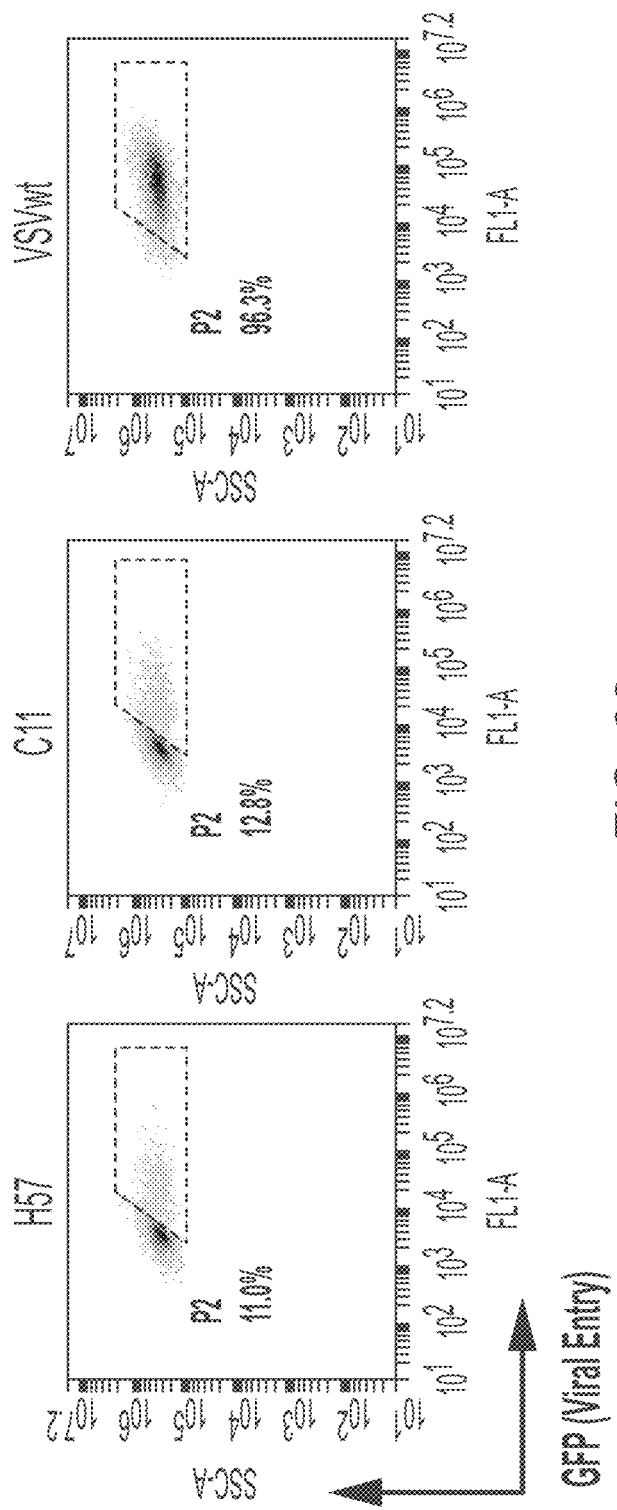

FIG. 26 depicts the ability of retroviruses comprising a mutated VSV-G viral envelope protein and either an anti-TCR-alpha beta antibody (H57) or an anti-CD3 antibody (C11) to infect of TCR-transduced 58−/− mouse cell lines.

Figure 27:
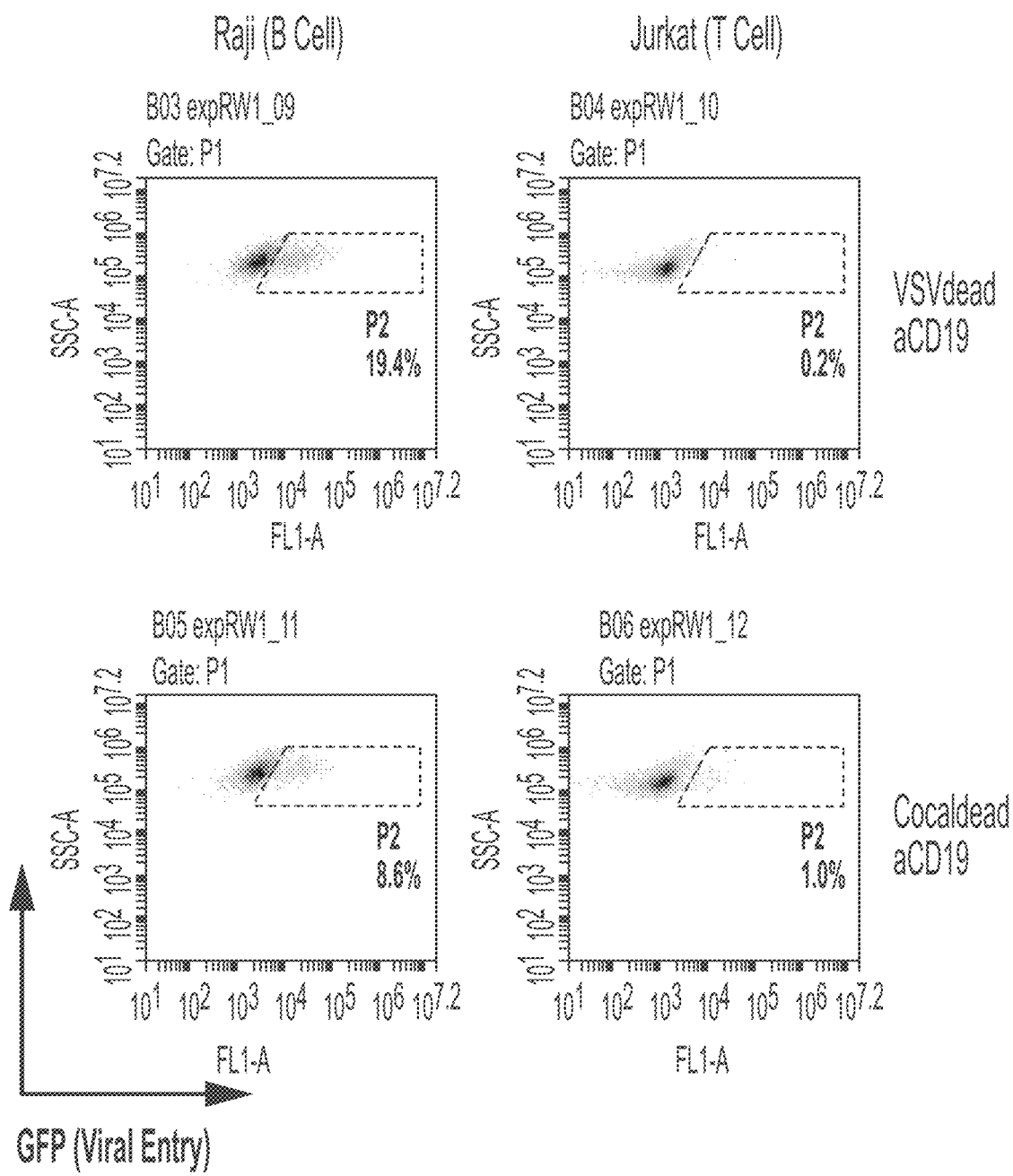

FIG. 27 depicts the ability of a retrovirus comprising either a mutated VSV-G viral envelope protein or a mutated cocal viral envelope protein; and an anti-CD19 scFv antibody to infect and enter CD19+ Raji cells, while not infecting CD19− Jurkat cells. A retrovirus comprising a wild-type VSV-G viral envelope protein and an anti-CD19 scFv antibody infects both CD19+ Raji cells and CD19 Jurkat cells.

DETAILED DESCRIPTION OF THE INVENTION

Herein are provided new and innovative methods, for example, to screen cells that are notoriously challenging to screen for specific antigens and function (e.g., T cells), and to deliver nucleic acids to target cells in a target-specific manner. In some embodiments, described herein are systems that enable, for example, repertoire-scale analysis of T cell receptor (TCR)-peptide-Major Histocompatibility Complex (pMHC) specificity, a previously intractable bottleneck, as previously described methods required considerable effort to determine what a single T cell clone can recognize (e.g., as in a typical immune response). In some embodiments, described herein are retrovirus-based systems that repurpose viral tropism as a method of selecting for molecular interactions and replace the binding functions of wild-type virus surface proteins with those of protein variants of interest, for example, by encoding these protein variants on the corresponding transfer plasmid used to make the virus, thereby ensuring that the resulting virus displays the protein variant on its surface and packaging the corresponding genetic sequence. As such, when the virus enters a target cell (e.g., bearing a receptor that binds the displayed extracellular targeting domain of the protein variant), cell entry results in integration of the genetic sequence of the displayed protein into the genome of the target cell.

Previous approaches for studying T cell specificity required a combination of generated T cell lines, recombinant expression of T cell receptors, and/or the individual validation of T cell binding or activity via a candidate antigen-based approach. Each of these elements provided an inherent limitation in the throughput of T cells or antigens screened. For example, yeast display based methods to deorphanize T cell receptors alleviated the bottleneck of number of antigens examined (with the ability to screen >$10^8$ ligands), but were still severely limited by the need to recombinantly express TCRs. The current strategies of the present invention described herein represents a tremendous advance in the study of T cell specificity and screening of T cells by allowing for screening of >$10^8$ ligands and without need for recombinant TCR expression.

Retroviruses

Described herein are retroviruses comprising a viral envelope protein comprising at least one mutation that diminishes its native function, a non-viral membrane-bound protein comprising a membrane-bound domain and an extracellular targeting domain, and a nucleic acid encoding a reporter. In some embodiments, a retrovirus comprises a viral envelope protein comprising at least one mutation that diminishes its native function and a non-viral membrane-bound protein comprising a membrane-bound domain and an extracellular targeting domain.

The retrovirus disclosed herein comprise one or more elements derived from a retroviral genome (naturally-occurring or modified) of a suitable species. Retroviruses include 7 families: alpharetrovirus (Avian leucosis virus), betaretrovirus (Mouse mammary tumor virus), gammaretrovirus (Murine leukemia virus), deltaretrovirus (Bovine leukemia virus), epsilonretrovirus (Walleye dermal sarcoma virus), lentivirus (Human immunodeficiency virus 1), and spumavirus (Human spumavirus). Six additional examples of retroviruses are provided in U.S. Pat. No. 7,901,671.

In some embodiments, a retrovirus is a lentivirus. Lentivirus is a genus of retroviruses that typically gives rise to slowly developing diseases due to their ability to incorporate into a host genome. Modified lentiviral genomes are useful as viral vectors for the delivery of a nucleic acids to a host cell. Host cells can be transfected with lentiviral vectors, and optionally additional vectors for expressing lentiviral packaging proteins (e.g., VSV-G, Rev, and Gag/Pol) to produce lentiviral particles in the culture medium.

Retrovirus and lentivirus constructs are well known in the art and any suitable retrovirus can be used to construct the retrovirus (or a plurality or library of retroviruses) as described herein. Non-limiting examples of retrovirus constructs include lentiviral vectors, human immunodeficiency viral (HIV) vector, avian leucosis viral (ALV) vector, murine leukemia viral (MLV) vector, murine mammary tumor viral (MMTV) vector, murine stem cell virus, and human T cell leukemia viral (HTLV) vector. These retrovirus constructs comprise proviral sequences from the corresponding retrovirus.

The retrovirus described herein may comprise the viral elements such as those described herein from one or more suitable retroviruses, which are RNA viruses with a single strand positive-sense RNA molecule. Retroviruses comprise a reverse transcriptase enzyme and an integrase enzyme. Upon entry into a target cell, retroviruses utilize their reverse transcriptase to transcribe their RNA molecule into a DNA molecule. Subsequently, the integrase enzyme is used to integrate the DNA molecule into the host cell genome. Upon integration into the host cell genome, the sequence from the retrovirus is referred to as a provirus (e.g., proviral sequence or provirus sequence). The retroviral vectors described herein may further comprise additional functional elements as known in the art to address safety concerns and/or to improve vector functions, such as packaging efficiency and/or viral titer. Additional information may be found in US20150316511 and WO2015/117027, the relevant disclosures of each of which are herein incorporated by reference for the purpose and subject matter referenced herein. Additional information for lentiviruses can be found in, e.g., WO2019/056015, the relevant disclosures of which are incorporated by reference herein for this particular purpose.

In some embodiments, lentiviruses are able to be targeted to target-specific cells via the pMHC-TCR interaction or any other protein-protein cell-to-cell interaction. In some embodiments, T cells with a known and relevant specificity can be enhanced (in the case of cancer or infection) or ablated (in the case of autoimmunity) without affecting other T cells, dramatically limiting the risk of off-target effects. In some embodiments, lentiviruses may encode an extracellular domain to target any other surface-expressed molecule on a target cell.

Viral Envelope Protein

The retroviruses described herein comprise a viral envelope protein comprising at least one mutation that diminishes its native function (e.g., wild-type function of a non-mutated viral envelope protein). In some embodiments, a viral envelope protein is any viral envelope protein of any retrovirus (e.g., lentivirus). A viral envelope protein may be a VSV-G envelope protein, a measles virus envelope protein, a nipah virus envelope protein, or a cocal virus G protein. In some embodiments, the native function that is diminished by a mutation of a viral envelope protein is viral tropism (e.g., ability to infect cells, bind to cells, etc.)

In some embodiments, a viral envelope protein comprising at least one mutation that diminishes its native function is a mutated VSV-G envelope protein. In some embodiments, a viral envelope protein comprising at least one mutation that diminishes its native function is a mutated measles virus envelope protein. In some embodiments, a viral envelope protein comprising at least one mutation that diminishes its native function is a mutated nipah virus envelope protein. In some embodiments, a viral envelope protein comprising at least one mutation that diminishes its native function is a mutated cocal virus G protein.

In some embodiments, a mutated VSV-G envelope protein comprises a mutation at H8, K47, Y209, and/or R354. In some embodiments, a mutated VSV-G envelope protein comprises a H8A, K47A, K47Q, Y209A, R354A, and/or R354Q mutation. In some embodiments, a mutated VSV-G envelope protein is as described in Nikolic et al., "Structural basis for the recognition of LDL-receptor family members by VSV glycoprotein." Nature Comm., 2018, 9:1029, the relevant disclosures of which are incorporated by reference herein for this particular purpose.

In some embodiments, a mutated measles virus envelope protein comprises a mutation at Y481, R533, S548, and/or F549. In some embodiments, a mutated measles virus envelope protein comprises a Y481A, R533A, S548L, and/or F549S mutation.

In some embodiments, a mutated Nipah virus envelope protein comprises a mutation at E501, W504, Q530, and/or E533. In some embodiments, a mutated measles virus envelope protein comprises a E501A, W504A, Q530A, and/or E533A mutation.

In some embodiments, a mutated cocal virus G protein comprises a mutation at K64 and/or R371. In some embodiments, a mutated cocal virus G protein comprises a mutation at K64Q and/or R371A.

In some embodiments, the mutated envelope protein is derived from any other enveloped virus including but not limited to baculovirus, herpes simplex virus (HSV), cytomegalovirus (CMV), lymphocytic choriomeningitis virus (LCMV), Epstein-Barr virus (EBV), vaccinia virus, Hepatitis A, B, or C virus, vaccinia virus, alphavirus, dengue virus, yellow fever virus, Zika virus, influenza virus, hantavirus, Ebola virus, rabies virus, human immunodeficiency virus (HIV), coronavirus, and other members of rhabdoviridae.

In some embodiments, a viral envelope protein comprising at least one mutation comprises 1, 2, 3, 4, 5, 6, 7, 8, 9, 10, or more mutations. In some embodiments, a viral envelope protein comprising at least one mutation comprises a nucleotide sequence and/or amino acid sequence that is at least 50%, 60%, 70%, 80%, 90%, 95%, or 97% identical to a wild-type viral envelope protein. In some embodiments, a viral envelope protein comprising at least one mutation that diminishes its native function retains less than 95%, 90%, 80%, 70%, 60%, 50%, 40%, 30%, 20%, or 10% of the function of a wild-type viral envelope protein. In some embodiments, a viral envelope protein comprising at least one mutation lacks all of its native function. In some embodiments, a retrovirus comprising a viral envelope protein comprising at least one mutation that diminishes its native function comprises less than 95%, 90%, 80%, 70%, 60%, 50%, 40%, 30%, 20%, or 10% of the cellular infectivity of a retrovirus comprising a wild-type viral envelope protein.

Non-Viral Membrane-Bound Protein

The retroviruses described herein comprise a non-viral membrane-bound protein. A non-viral membrane-bound protein may comprise a membrane-bound domain and an extracellular targeting domain. In some embodiments, a non-viral membrane-bound protein is a chimeric protein comprising sequences from at least two different proteins. In some embodiments, a non-viral membrane-bound protein is a full-length or truncated protein comprising sequence from a single protein.

A membrane-bound domain is a protein or peptide that has an amino acid sequence that enables the protein or peptide to be fully or partially embedded or associated with the membrane (e.g., envelope) of the retrovirus. In some embodiments, a membrane-bound domain enables presentation and delivery of the extracellular targeting domain to the extracellular environment. In some embodiments, a membrane-bound domain comprises an intracellular domain, a transmembrane domain, and/or an extracellular domain. In some embodiments, a membrane-bound domain comprises an intracellular domain and a transmembrane domain. In some embodiments, the membrane-bound domain comprises a Major Histocompatibility Complex (MHC) protein or fragment thereof. A MHC protein may be a Class I or Class II MHC protein.

In some embodiments, a membrane-bound domain comprises 10-50, 10-100, 25-100, 50-200, 50-150, 100-500, 100-250, 250-500, or any reasonable number of total amino acids.

In some embodiments, a retrovirus present in a library of retroviruses comprises the same membrane-bound domain as some or all of the other retroviruses in the library. In some embodiments, each retrovirus present in a library of retroviruses comprises a different membrane-bound domain relative to some or all of the other retroviruses in the library.

In some embodiments, an extracellular targeting domain is any protein or peptide that has an amino acid sequence and is a binding partner for a target molecule or ligand (e.g., a cognate protein) on a cell surface. When present in the extracellular environment beyond the interior of the retrovirus, an extracellular targeting domain is capable of binding to a target cell. In some embodiments, an extracellular targeting domain binds or targets to a cognate protein or ligand (e.g., a protein receptor present on a target cell) that is present on the cell surface of a cell or a subset of a population of cells. In some embodiments, an extracellular targeting domain binds to a cognate protein or ligand that is present on the cell surface of a single T cell or a subset of a population of T cells. In some embodiments, a binding interaction between an extracellular targeting domain of a retrovirus and a cognate protein or ligand of a cell enables the retrovirus to enter the cell (e.g., an antigen-specific cell, e.g., a T cell).

In some embodiments, an extracellular targeting domain comprises 10-50, 10-100, 25-100, 50-200, 50-150, 100-500, 100-250, 250-500, or any reasonable number of total amino acids. In some embodiments, an extracellular targeting domain comprises at least 5, at least 10, at least 15, at least 20, or at least 50 amino acids.

In some embodiments, an extracellular targeting domain is a protein, an antibody or peptide. In some embodiments, an antibody is a full-length antibody, an antibody fragment, a nanobody, or a single chain antibody (scFv). In some embodiments, an extracellular targeting domain is an antibody that binds to a cognate protein of a target cell. In some embodiments, an extracellular targeting domain is an antibody that binds to a B-cell or T cell antigen. In some embodiments, an extracellular targeting domain is an anti-CD19 antibody (e.g., an antibody that binds to CD19). In some embodiments, an extracellular targeting domain is an antibody that binds to any cell surface molecule. In some embodiments, an extracellular targeting domain is an antibody that binds to a lineage marker (e.g., CD3, CD20, integrins, or other receptors), phenotypic markers (PD-1, CD25, CD45, or others). In some embodiments, an extracellular targeting domain is a protein or peptide that binds to a receptor (e.g., a receptor that is present on the surface of a target cell). In some embodiments, an extracellular targeting domain is a protein or peptide that binds to a cytokine receptor (e.g., interleukin-13 (IL-13) receptor). In some embodiments, an extracellular targeting domain is a cytokine (e.g., IL-2, IL-6, IL-12, IL-13). In some embodiments, an extracellular targeting domain is a chemokine ligand (e.g. CXCL9, CXCL10, CXCL 11, etc.). In some embodiments, an extracellular targeting domain is a cellular receptor, including cytokine receptors (e.g. IL-13Rα1, IL-13Rα2, IL-2 receptors, common gamma chain), GPCRs (including chemokine receptors such as CSCR3, CXCR4, etc.), and integrins. In some embodiments, an extracellular targeting domain is a peptide that is displayed by a MHC protein. In some embodiments, non-viral membrane-bound protein comprises a membrane-bound domain comprising a MHC protein or fragment and an extracellular targeting domain comprising a peptide that is displayed by a MHC protein. In some embodiments, an extracellular domain binds to a T cell receptor and/or a B cell receptor. T-cell receptors are expressed in nature on the surface of T-cells usually as alpha/beta and gamma/delta heterodimeric integral membrane proteins, each subunit comprising a short intracellular segment, a single transmembrane alpha-helix and two globular extracellular Ig-superfamily domains. B-cell receptors are transmembrane receptor proteins located on the outer surface of B cells.

In some embodiments, an extracellular targeting domain binds to a target cell or cell surface molecule with a binding affinity of $10^{-9}$ to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{-2}$ M. In some embodiments, an extracellular targeting domain binds to a cognate protein or ligand of a target cell with a binding affinity of $10^{-9}$ to $10^{-8}$ M, $10^{-8}$ to $10^{-7}$ M, $10^{-7}$ to $10^{-6}$ M, $10^{-6}$ to $10^{-5}$ M, $10^{-5}$ to $10^{-4}$ M, $10^{-4}$ to $10^{-3}$ M, or $10^{-3}$ to $10^{-2}$ M. In some embodiments, the binding affinity between an extracellular targeting domain and a cognate protein or ligand is in the picomolar to nanomolar range (e.g., between about $10^{-12}$ and about $10^{-9}$ M). In some embodiments, the binding affinity between an extracellular targeting domain and a cognate protein or ligand is in the nanomolar to micromolar range (e.g., between about $10^{-9}$ and about $10^{-6}$ M). In some embodiments, the binding affinity between an extracellular targeting domain and a cognate protein or ligand is in the micromolar to millimolar range (e.g., between about $10^{-6}$ and about $10^{-3}$ M). In some embodiments, the binding affinity between an extracellular targeting domain and a cognate protein or ligand is in the picomolar to micromolar range (e.g., between about $10^{-12}$ and about $10^{-6}$ M). In some embodiments, the binding affinity between an extracellular targeting domain and a cognate protein or ligand is in the nanomolar to millimolar range (e.g., between about $10^{-9}$ and about $10^{-3}$ M).

As used herein, the term antibody generally refers to a protein that includes at least one immunoglobulin variable domain or immunoglobulin variable domain sequence. For example, an antibody can include a heavy (H) chain variable region (abbreviated herein as $V_H$), and/or a light (L) chain variable region (abbreviated herein as $V_L$). In another example, an antibody includes two heavy (H) chain variable regions and/or two light (L) chain variable regions. An antibody can have the structural features of IgA, IgG, IgE, IgD, IgM (as well as subtypes thereof). The $V_H$ and $V_L$ regions can be further subdivided into regions of hypervariability, termed "complementarity determining regions" ("CDR"), interspersed with regions that are more conserved, termed "framework regions" ("FR"). Each $V_H$ and/or $V_L$ is typically composed of three CDRs and four FRs, arranged from amino-terminus to carboxy-terminus in the following order: FR1, CDR1, FR2, CDR2, FR3, CDR3, FR4. The $V_H$ or $V_L$ chain of the antibody can further include a heavy or light chain constant region, to thereby form a heavy or light immunoglobulin chain, respectively. In some embodiments, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3.

In some embodiments, a retrovirus present in a library of retroviruses comprises the same extracellular targeting domain as some or all of the other retroviruses in the library. In some embodiments, each retrovirus present in a library of retroviruses comprises a different extracellular targeting domain relative to some or all of the other retroviruses in the library.

In some embodiments, a non-viral membrane-bound protein further comprises a signal sequence (also referred to as a signal peptide of localization sequence). In some embodiments, the signal sequence is at the N- or C-terminal ends of the non-viral membrane-bound protein. A signal sequence functions to translocate the non-viral membrane-bound protein to the membrane (or envelope) of the retrovirus. In some embodiments, a signal sequence is 5-10, 5-15, 10-20, 15-20, 15-30, 20-30, or 25-30 amino acids. In some embodiments, the signal sequence is an Ig Kappa leader sequence (e.g., a murine Ig Kappa leader sequence comprising: METDTLLL-WVLLLWVPGSTG (SEQ ID NO: 1)) or a B2M signal peptide sequence (e.g., a B2M signal peptide sequence comprising: MSRSVALAVLALLSLSGLEA (SEQ ID NO: 2)). In some embodiments, a retrovirus present in a library of retroviruses comprises the same signal sequence as some or all of the other retroviruses in the library. In some embodiments, each retrovirus present in a library of retroviruses comprises a different signal sequence relative to some or all of the other retroviruses in the library.

In some embodiments, a nucleic acid encoding a non-viral membrane-bound protein further comprises an internal ribosome entry site (IRES). An IRES is an RNA sequence that allows for initiation of translation during protein synthesis. In some embodiments, the IRES is located at or near the C-terminal end. In some embodiments, the IRES is located C-terminal relative to the membrane-bound domain and the extracellular targeting domain. In some embodiments, the IRES is a viral IRES. In some embodiments, the IRES is an IRES that is native to the retrovirus. In some embodiments, the IRES is a sequence derived from encephalomyocarditis virus (EMCV). In some embodiments, a retrovirus present in a library of retroviruses comprises the same IRES as some or all of the other retroviruses in the library. In some embodiments, each retrovirus present in a library of retroviruses comprises a different IRES relative to some or all of the other retroviruses in the library.

In some embodiments, a non-viral membrane-bound protein further comprises a linker positioned between the membrane-bound domain and the extracellular targeting domain. A linker is an amino acid linker and may be a rigid linker, a flexible linker, or an oligomerized linker. A rigid linker is an amino acid sequence that lacks flexibility (e.g., may comprise at least one proline). In some embodiments, a rigid linker comprises a platelet-derived growth factor receptor (PDGFR) stalk or a CD8a stalk. In some embodiments, a PDGFR stalk comprises an amino acid sequence comprising AVGQDTQEVIVVPHSLPFK (SEQ ID NO: 3). In some embodiments, a PDGFR stalk comprises an amino acid sequence comprising ASAKPTTTPAPRPPTPAPTIA-SQPLSLRPEAARPAAGGAVHTRGLDFAK (SEQ ID NO: 4) A flexible linker is an amino acid sequence that has many degrees of freedom (e.g., may comprise a plurality of amino acids with small side chains, e.g., glycine or alanine). In some embodiments, a flexible linker comprises an amino acid sequence comprising GAPGAS (SEQ ID NO: 5). In some embodiments, a flexible linker comprises an amino acid sequence consisting of GAPGSGGGGSGGGGSAS (SEQ ID NO: 6). In some embodiments, a flexible linker comprises an amino acid sequence comprising GGGGS (SEQ ID NO: 7). In some embodiments, a flexible linker comprises an amino acid sequence comprising (GAPGAS)N(SEQ ID NO: 29) or (G4S)N(SEQ ID NO: 30), wherein N is 1, 2, 3, 4, 5, 6, 7, 8, 9, 10, or more. An oligomerized linker is an amino acid that can oligomerize to another related amino amid. In some embodiments, an oligomerized linker is an amino acid sequence that can form a dimer, trimer, or tetramer. In some embodiments, an oligomerized linker comprises an IgG4 hinge domain (e.g., ASESKY-GPPCPPCPAVGQDTQEVIVVPHSLPFK (SEQ ID NO: 8)). In some embodiments, an oligomerized linker comprises an amino acid sequence that can form a tetrameric coiled coil (e.g., ASGGGGSGELAAIKQELAAIKKELAAIKWE-LAAIKQGAG (SEQ ID NO: 9)). In some embodiments, an oligomerized linker comprises an amino acid sequence that can form a dimeric coiled coil (e.g., ASESKYGPPCPPCP (SEQ ID NO: 10)).

Reporter

In some embodiments, the retroviruses described herein may comprise a reporter (e.g., a reporter protein). In some embodiments, the retroviruses described herein comprise a nucleic acid encoding a reporter (e.g., a reporter protein). As used herein, a reporter is generally a protein or gene that can be detected when expressed in a retrovirus and/or target cell. In some embodiments, the presence or absence of a reporter in a target cell or a subset of a target cells in a population of cells allows for the ability to sort cells (e.g., using flow cytometry and/or fluorescence-activated cell sorting).

In some embodiments, a reporter is a fluorescent protein. A fluorescent protein may be a green fluorescent protein (GFP), yellow fluorescent protein (YFP), red fluorescent protein (RFP). A fluorescent protein may be as described in U.S. Pat. No. 7,060,869, entitled "Fluorescent protein sensors for detection of analytes".

In some embodiments, a reporter is an antibiotic resistance marker. In some embodiments, an antibiotic resistance marker is a protein or gene that confers a competitive advantage to a target cell that contains the marker. In some embodiments, the antibiotic resistance marker comprises a hygromycin resistance protein or gene, a kanamycin resistance protein or gene, ampicillin resistant protein or gene, streptomycin resistant protein or gene, or a neomycin resistance protein or gene.

Cells

A cell as described herein may be any bacterial, mammalian, or yeast cell. In some embodiments, a cell is a human, mouse, rat, or a non-human primate cell. In some embodiments, a cell is a somatic cell or a reproductive cell. In some embodiments, a cell is an epithelial cell, a neural cell, a hormone-secreting cell, an immune cell, a secretory cell, a blood cell, an interstitial cell, or a germ cell. In some embodiments, a cell is an antigen-specific cell (e.g., a cell that binds to a specific antigen). In some embodiments, an antigen-specific cell is an immune cell. In some embodiments, an antigen-specific cell is a B cell or a T cell. In some embodiments, a cell is a target cell (e.g., that comprises a cognate protein or ligand capable of being targeted by a retrovirus described herein)

A population of cells as described herein may be any bacterial, mammalian, or yeast cell population. In some embodiments, a population of cells is a population of human, mouse, rat, or non-human primate cells. In some embodiments, a population of cells is a somatic cell population or a reproductive cell population. In some embodiments, a population of cells comprises epithelial cells, neural cells, hormone-secreting cells, immune cells, secretory cells, blood cells, interstitial cells, and/or germ cells. In some embodiments, a population of cells comprises antigen-specific cells (e.g., cells that binds to a specific antigen). In some embodiments, a population of antigen-specific cells comprises immune cells. In some embodiments, a population of antigen-specific cells comprises B cells and/or T cells. In some embodiments, a population of cells comprises a homogenous population of cells. In some embodiments, a population of cells comprises a heterogeneous population of cells.

In some embodiments, a population of cells is a population of cells isolated from a subject. A subject may be a human subject (e.g., a human subject suffering from a disease), a mouse subject, a rat subject, or a non-human primate subject. In some embodiments, a population of cells is isolated from the blood or a tumor of a subject.

In some embodiments, a population of cells has been previously frozen and thawed (e.g., 1, 2, 3, 4, 5, or more freeze/thaw cycles). In some embodiments, a population of cells are maintained in liquid culture media. In some embodiments, a population of cells have been passaged 1, 2, 3, 4, 5, or more times, using any known method. In some embodiments, a population of cells are maintained in liquid culture media prior to being combined with a retrovirus or plurality of retroviruses. In some embodiments, a population of cells are maintained in liquid culture media after to being combined with a retrovirus or plurality of retroviruses. In some embodiments, a population of cells are maintained in liquid culture media prior to while being combined with a retrovirus or plurality of retroviruses.

In some embodiments, a population of cells comprises any of the retroviruses described herein. In some embodiments, a subset of a population of cells contain any of the retroviruses described herein. In some embodiments, a subset of a population of cells contains the retrovirus inside each cell of the subset (e.g., inside the nucleus of each cell of the subset). In some embodiments, a population of cells or a subset thereof expresses a reporter (e.g., a fluorescent protein or an antibiotic resistance marker). In some embodiments, a population of cells or a subset thereof (e.g., containing a retrovirus) are isolated and/or sorted based on the presence or absence of a reporter. In some embodiments, a subset of a population of cells that contain retrovirus described herein are isolated and/or sorted based on the presence or absence of a reporter away from the cells of the population that do not contain the retrovirus. In some embodiments, at least 50%, 60%, 70%, 80%, 90%, or 95% of a population of cells prior to cell sorting contain a retrovirus. In some embodiments, at least 70%, 80%, 90%, 95%, or 100% of a population of cells contain a retrovirus following isolation and/or sorting based on the presence or absence of a reporter.

Methods of Screening

Described herein are methods of screening a population of cells comprising: (i) providing a retrovirus comprising a viral envelope protein comprising at least one mutation that diminishes its native function, a non-viral membrane-bound protein comprising a membrane-bound domain and an extracellular targeting domain, and a nucleic acid encoding a reporter; (ii) combining the retrovirus with a population of cells; and (iii) sorting the population of cells based on the presence or absence of the reporter. In some embodiments, the retrovirus of (i) comprises a nucleic acid comprising a structure: S-ETD-MBD-IRES-R, wherein S encodes a signal sequence, ETD encodes an extracellular targeting domain; MBD encodes a membrane-bound domain, IRES encodes an internal ribosome entry site, and R encodes a reporter; and a mutated viral envelope protein comprising at least one mutation that diminishes its native function.

As used herein, the term "combining" (which, in some embodiments, is synonymous with the terms "providing" and "contacting") generally refers to the act of bringing a retrovirus into close, physical contact with a population of cells, such that the extracellular targeting domain of the retrovirus is capable of binding to the cognate ligand present on a subset of cells of the population. In some embodiments, combining of a retrovirus and a population of cells occurs when a solution comprising the retrovirus and a solution comprising the population of cells are mixed. In some embodiments, combining of a retrovirus and a population of cells occurs when a lyophilized retrovirus and a solution comprising the population of cells are mixed. In some embodiments, combining of a retrovirus and a population of cells occurs when a lyophilized retrovirus and a lyophilized population of cells are mixed and reconstituted with a solution. In some embodiments, the cells of the population are maintained in cell culture media, in a monolayer of cells, and/or are attached to a tissue culture plate or petri dish.

Generally, a retrovirus and a population of cells are combined (e.g., physically combined or contacted) for a defined period of time. In some embodiments, a period of time is measured in seconds, minutes, hours or days. In some embodiments, period of time is 0-30 seconds, 15-45 seconds, 30-60 seconds, 45-90 seconds, 60-90 seconds, or 60-120 seconds. In some embodiments, a retrovirus and a population of cells are combined and in contact for 0-30 seconds, 15-45 seconds, 30-60 seconds, 45-90 seconds, 60-90 seconds, or 60-120 seconds. In some embodiments, period of time is 1-2 minutes, 1-5 minutes, 1-10 minutes, 2-10 minutes, 5-10 minutes, 5-20 minutes, 10-20 minutes, 25-30 minutes, 25-60 minutes, 30-45 minutes, 30-40 minutes, 40-60 minutes, 50-70 minutes, or 60-120 minutes. In some embodiments, a retrovirus and a population of cells are combined and in contact for 1-2 minutes, 1-5 minutes, 1-10 minutes, 2-10 minutes, 5-10 minutes, 5-20 minutes, 10-20 minutes, 25-30 minutes, 25-60 minutes, 30-45 minutes, 30-40 minutes, 40-60 minutes, 50-70 minutes, or 60-120 minutes. In some embodiments, a period of time is 1-2 hours, 1-5 hours, 1-3 hours, 2-5 hours, 3-6 hours, 3-12 hours, 6-12 hours, 12-18 hours, 12-24 hours, 15-30 hours, 18-24 hours, 24-48 hours, 24-36 hours, or 36-50 hours. In some embodiments, a retrovirus and a population of cells are combined and in contact for 1-2 hours, 1-5 hours, 1-3 hours, 2-5 hours, 3-6 hours, 3-12 hours, 6-12 hours, 12-18 hours, 12-24 hours, 15-30 hours, 18-24 hours, 24-48 hours, 24-36 hours, or 36-50 hours. In some embodiments, a period of time is 1, 2, 3, 4, 5, 6, 7, 8, 9, 10, or 5-15 days. In some embodiments, a retrovirus and a population of cells are combined and in contact for 1, 2, 3, 4, 5, 6, 7, 8, 9, 10, or 5-15 days.

In some embodiments, a population of cells are sorted based on the presence or absence of the reporter. In some embodiments, a subset of the population of cells containing the reporter (e.g., express the reporter) are sorted from the remaining subset of the population of cells that do not contain the reporter. In some embodiments, sorting of the population of cells is performed using flow cytometry (e.g., fluorescence-activated cell sorting), next-generation genome sequencing (e.g., single-cell next-generation sequencing), or antibiotic selection.

In some embodiments, the conditions of step (ii) that allow for the retrovirus to have cell-to-cell interactions with a subset of the population of cells comprise combining the retrovirus and the population of cells in the presence of defined solutions, compositions and at specific temperatures. In some embodiments, the retrovirus and the population of cells are combined in the presence of a cell culture media (e.g., RPMI or DMEM cell culture media). In some embodiments, the retrovirus and the population of cells are combined in the presence of a buffered saline solution. In some embodiments, a buffered saline solution is a phosphate-buffered saline or HEPES-buffered saline. In some embodiments, a buffered saline solution comprises bovine serum albumin and/or EDTA. In some embodiments, the retrovirus and the population of cells are combined in the presence of an enhancer of retroviral transduction (e.g., heparin sulfate, polybrene, protamine sulfate, or dextran). In some embodiments, the retrovirus and the population of cells are combined in (ii) at a temperature ranging from 4° C. to 42° C., 4° C. to 8° C., 4° C. to 10° C., 8° C. to 15° C., 10° C. to 20° C., 18° C. to 23° C., 20° C. to 30° C., 25° C. to 35° C., 30° C. to 40° C., or 37° C. to 42° C.

In some embodiments, the methods of screening described herein further comprise washing the population of cells between steps (ii) and (iii) with a wash solution. In some embodiments, a wash solution is any liquid solution that allows for maintenance of healthy cells (e.g., solution comprising neutral pH, low-to-moderate levels of ionic strength). In some embodiments, washing the population of cells removes excess and/or remaining retrovirus from the population of cells. In some embodiments, the population of cells are washed using a cell culture media (e.g., RPMI or DMEM cell culture media). In some embodiments, the population of cells are washed using a buffered saline solution. In some embodiments, a buffered saline solution is a phosphate-buffered saline or HEPES-buffered saline. In some embodiments, a buffered saline solution comprises bovine serum albumin and/or EDTA. In some embodiments, the population of cells are washed at a temperature ranging from 4° C. to 42° C., 4° C. to 8° C., 4° C. to 10° C., 8° C. to 15° C., 10° C. to 20° C., 18° C. to 23° C., 20° C. to 30° C., 25° C. to 35° C., 30° C. to 40° C., or 37° C. to 42° C.

In some embodiments, the population of cells are maintained in liquid culture prior to being combined with the retrovirus. In some embodiments, the population of cells are maintained in liquid culture after being combined with the retrovirus. In some embodiments, the population of cells are maintained in liquid culture during the combining step with the retrovirus. In some embodiments, the population of cells are attached to a cell culture plate or petri dish. In some embodiments, the population of cells are maintained in a monolayer, an embryoid body, or any cell aggregate.

In some embodiments, methods of screening comprise the use of a plurality of retroviruses. In certain embodiments, a plurality of retroviruses comprises at least $10^2$, $10^3$, $10^4$, $10^5$, $10^6$, $10^7$, $10^8$, $10^9$, $10^{10}$, $10^{11}$, or $10^{12}$ unique retroviruses. In some embodiments, there may be at least $10^2$, $10^3$, $10^4$, $10^5$, $10^6$, $10^7$, $10^8$, $10^9$, $10^{10}$, $10^{11}$, or $10^{12}$ copies of each unique retrovirus present in a plurality of retroviruses.

In some embodiments, methods of screening comprise screening a population of cells with at least two different, unique retroviruses. In some embodiments, a different, unique retrovirus comprises a different extracellular targeting domain and/or a different reporter. In some embodiments, methods of screening comprise a first retrovirus and a second retrovirus, wherein the first and second retrovirus comprise different extracellular targeting domains and/or different reporters. In some embodiments, methods of screening comprise screening a population of cells with 2, 3, 4, 5, 6, 7, 8, 9, 10, 50, 100 or more different retroviruses. In some embodiments, methods of screening comprise screening a population of cells with a library of retroviruses. In some embodiments, a library of retroviruses comprises at least $10^2$, at least $10^3$, at least $10^4$, at least $10^5$, at least $10^6$, at least $10^7$, at least $10^8$, at least $10^9$, or at least $10^{10}$ unique retroviruses.

Library of Retroviruses

Described herein are libraries of retroviruses, wherein a library comprises a plurality of unique retroviruses, wherein each unique retrovirus comprises a viral envelope protein comprising at least one mutation that diminishes its native function, a non-viral membrane-bound protein comprising a membrane-bound domain and an extracellular targeting domain, and a nucleic acid encoding a reporter, and wherein each unique retrovirus comprises a different and unique extracellular targeting domain. Also described herein are libraries of cells comprising retroviruses, wherein a library comprises a plurality of unique cells, wherein each unique cell comprises a unique retrovirus.

In some embodiments, libraries include pMHC-encoded (peptide/MHC-encoded) retroviral (e.g., lentiviral) libraries for use in screening populations of T cells. In such libraries, the pMHC displayed on the virus surface will enable T cell infection in a TCR-specific manner. Infected T cells can be collected and sequenced, allowing for the identification of pMHC ligands that can infect a subset of a T cell population of interest and the ability to simultaneously track TCR sequences and reactive pMHC ligands. In some embodiments, pMHC retroviral libraries minimally comprise randomized transfer vectors containing randomized pMHC targeting elements. In some embodiments, randomly derived libraries are generated using degenerate oligonucleotide primers. In some embodiments, targeted libraries that are specific for a unique set of antigens (e.g., all possible viral or bacterial antigens for a particular target of interest— human immunodeficiency virus, tuberculosis TB, etc.; or all possible neoantigens for a particular subject) are generated.

In some embodiments, a library is capable of being screened against a population of antigen-specific cells (e.g., B cells or T cells). In some embodiments, a library comprises at least $10^2$, at least $10^3$, at least $10^4$, at least $10^5$, at least $10^6$, at least $10^7$, at least $10^8$, at least $10^9$, or at least $10^{10}$ unique retroviruses. In some embodiments, a library comprising unique retroviruses comprises extracellular targeting domains that are at least 5, at least 10, at least 15, at least 20, or at least 50 amino acids in length. In some embodiments, each different and unique extracellular targeting domain is generated through site-directed mutagenesis.

Retroviral or cell libraries can vary in size from hundreds to hundreds of thousands, millions, or more unique retroviruses or unique cells. In some embodiments, the libraries of the disclosure comprise at least 500,000 unique retroviruses or unique cells. The libraries of the invention include retroviral libraries and cellular libraries. A library is a synthetic (i.e., isolated, synthetically produced, free from components that are naturally found together in a cell, purified before being put into the library) collection of members having a common element and at least one distinct element. The library comprises a thousand or more (e.g., at least: 1,000; 2,000; 3,000; 4,000; 5,000; 10,000; 50,000; 100,000; 500,000; 600,000; 700,000; 800,000; 900,000; 1,000,000; 2,000,000; 3,000,000; 4,000,000; or more) members. The upper limit of the library size is defined by the combinatorics of domains or modules providing distinctness or diversity among the members. For instance, an upper limit may be 4,000,000 members. Thus, in some embodiments, the library is highly diverse, and includes at least 500,000 distinct members. The highly diverse library may have a diversity of $10^6$ or greater. In some embodiments, a library of retroviruses is generated using site-directed mutagenesis of a nucleic acid described herein. In some embodiments, the site-directed mutagenesis involves the use of primers and a low-fidelity RNA polymerase to allow for randomized mutagenesis of a common nucleic acid as described herein.

Methods of Delivering Nucleic Acid to a Cell

Described herein are methods of delivering a nucleic acid to a cell, comprising (i) providing a retrovirus, as described herein, comprising the nucleic acid, a viral envelope protein comprising at least one mutation that diminishes its native function, and a non-viral membrane-bound protein comprising an extracellular targeting domain that is capable of binding to a cognate ligand of the cell; and (ii) contacting the retrovirus with the cell such that the retrovirus enters or infects the cell. In some embodiments, the nucleic acid encodes an mRNA molecule, optionally wherein the mRNA is a gene of interest. In some embodiments, the nucleic acid encodes a double-stranded RNA, an antisense RNA, a microRNA, or any other RNA molecule. In some embodiments, the gene of interest encodes a protein. In some embodiments, the gene of interest encodes a therapeutic protein (e.g., a protein to compensate for a diseased condition in a subject).

In some embodiments, the nucleic acid is delivered to the cell when the retrovirus enters or infects the cell during step (ii). In some embodiments, the methods of delivering a nucleic acid described herein do not require a transfection agent (e.g., a lipophilic transfection agent such as Lipofectin).

Methods of Detection

Described herein are methods of detecting an interaction between a retrovirus and a cell, comprising: (i) contacting a sample comprising the retrovirus and an cell with an antibody, wherein the retrovirus comprises a viral envelope protein comprising at least one mutation that diminishes its native function, a non-viral membrane-bound protein comprising an extracellular targeting domain, and wherein the antibody binds to the extracellular targeting domain of the retrovirus; (ii) optionally removing unbound antibody from the sample; and (iii) imaging the sample to detect whether the antibody-retrovirus complex is bound to the cell.

In some embodiments, the antibody further comprises at least one fluorescent label. In some embodiments, a fluorescent label is a xanthene derivative (e.g., fluorescein, rhodamine, Oregon green, eosin and Texas red), cyanine derivative (e.g., cyanine, indocarbocyanine, oxacarbocyanine, thiacarbocyanine and merocyanine), naphthalene derivative (e.g., dansyl and prodan derivatives), coumarin derivative, oxadiazole derivative (e.g., pyridyloxazole, nitrobenzoxadiazole and benzoxadiazole), pyrene derivative (e.g., cascade blue), oxazine derivative (e.g., Nile red, Nile blue, cresyl violet and oxazine 170), acridine derivative (e.g., proflavin, acridine orange and acridine yellow), arylmethine derivative (e.g., auramine, crystal violet and malachite green), or tetrapyrrole derivative (e.g., porphin, phthalocyanine and bilirubin). The fluorescent label may be non-covalently associated with the antibody or covalently linked to the antibody.

In some embodiments, the sample is imaged in step (iii) using confocal or fluorescence microscopy. In some embodiments, methods of detection can be accomplished using standard microscopy setups (e.g., confocal or fluorescence microscopes). In some embodiments, a sample is detected in an ultra-multiplexed format while imaging using standard confocal or epi-fluorescence microscope.

Nucleic Acids

As used herein, the term "nucleic acids" generally refers to multiple linked nucleotides (i.e., molecules comprising a sugar (e.g., ribose or deoxyribose) linked to an exchangeable organic base, which is either a pyrimidine (e.g., cytosine (C), thymidine (T) or uracil (U)) or a purine (e.g., adenine (A) or guanine (G)). Nucleic acids include DNA such as D-form DNA and L-form DNA and RNA, as well as various modifications thereof. Modifications include base modifications, sugar modifications, and backbone modifications.

It is to be understood that the nucleic acids used in retroviruses and methods of the invention may be homogeneous or heterogeneous in nature. As an example, they may be completely DNA in nature or they may be comprised of DNA and non-DNA (e.g., LNA) monomers or sequences. Thus, any combination of nucleic acid elements may be used. The modification may render the nucleic acid more stable and/or less susceptible to degradation under certain conditions. For example, in some instances, the nucleic acids are nuclease-resistant. Methods for synthesizing nucleic acids, including automated nucleic acid synthesis, are also known in the art.

The nucleic acids may comprise modifications in their bases. Modified bases include modified cytosines (such as 5-substituted cytosines (e.g., 5-methyl-cytosine, 5-fluoro-cytosine, 5-chloro-cytosine, 5-bromo-cytosine, 5-iodo-cytosine, 5-hydroxy-cytosine, 5-hydroxymethyl-cytosine, 5-difluoromethyl-cytosine, and unsubstituted or substituted 5-alkynyl-cytosine), 6-substituted cytosines, N4-substituted cytosines (e.g., N4-ethyl-cytosine), 5-aza-cytosine, 2-mercapto-cytosine, isocytosine, pseudo-isocytosine, cytosine analogs with condensed ring systems (e.g., N,N'-propylene cytosine or phenoxazine), and uracil and its derivatives (e.g., 5-fluoro-uracil, 5-bromo-uracil, 5-bromovinyl-uracil, 4-thio-uracil, 5-hydroxy-uracil, 5-propynyl-uracil), modified guanines such as 7 deazaguanine, 7 deaza 7 substituted guanine (such as 7 deaza 7 (C2 C6)alkynylguanine), 7 deaza 8 substituted guanine, hypoxanthine, N2-substituted guanines (e.g. N2-methyl-guanine), 5-amino-3-methyl-3H,6H-thiazolo[4,5-d]pyrimidine-2,7-dione, 2,6 diaminopurine, 2 aminopurine, purine, indole, adenine, substituted adenines (e.g. N6-methyl-adenine, 8-oxo-adenine) 8 substituted guanine (e.g. 8 hydroxyguanine and 8 bromoguanine), and 6 thioguanine. The nucleic acids may comprise universal bases (e.g. 3-nitropyrrole, P-base, 4-methyl-indole, 5-nitro-indole, and K-base) and/or aromatic ring systems (e.g. fluorobenzene, difluorobenzene, benzimidazole or dichloro-benzimidazole, 1-methyl-1H-[1,2,4]triazole-3-carboxylic acid amide). A particular base pair that may be incorporated into the oligonucleotides of the invention is a dZ and dP non-standard nucleobase pair reported by Yang et al. NAR, 2006, 34(21):6095-6101. dZ, the pyrimidine analog, is 6-amino-5-nitro-3-(1'-3-D-2'-deoxyribofuranosyl)-2(1H)-pyridone, and its Watson-Crick complement dP, the purine analog, is 2-amino-8-(1'-β-D-1'-deoxyribofuranosyl)-imidazo[1,2-a]-1,3,5-triazin-4(8H)-one.

Amino Acid Substitutions

In some embodiments, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g. Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

EXAMPLES

Example 1. Generation of retrovirus that targets antigen-specific T cells

Figure 1:
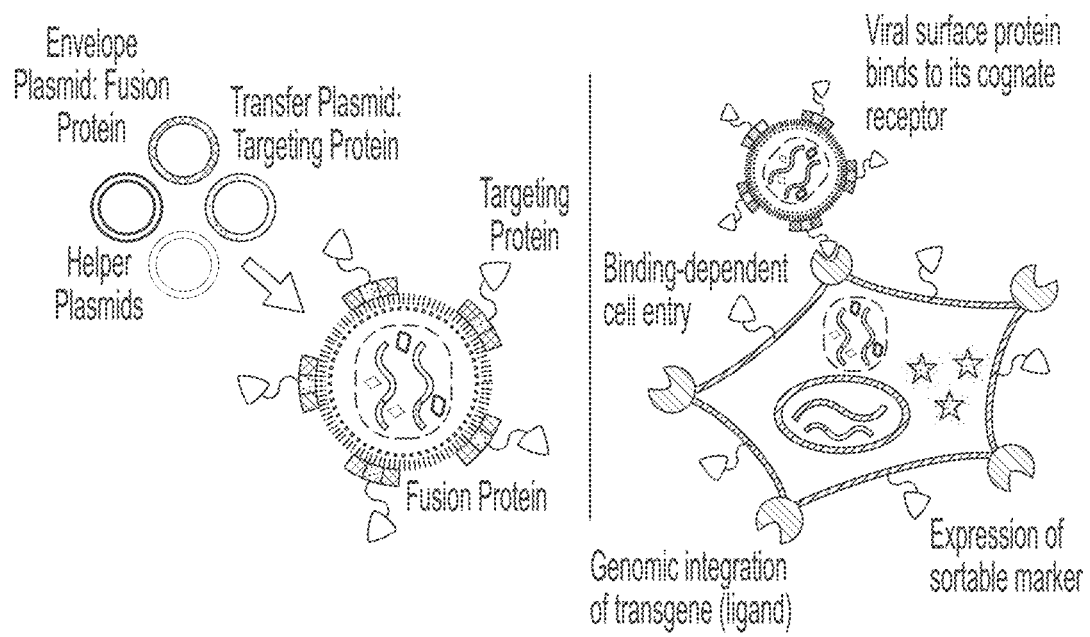
Figure 2:
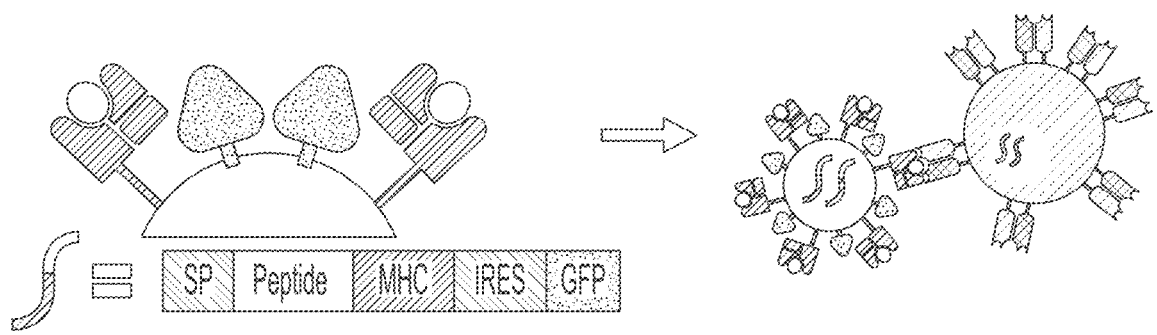

Targeted lentiviruses were generated by polyethylenimine (PEI) transfection of HEK293T cells with the following plasmids: an envelope plasmid encoding a mutated VSV-G envelope protein comprising K47Q and R354A mutations, at least one helper plasmid (pRRE, pRev, or psPAX2.1), and a transfer plasmid (FIG. 1). The transfer plasmids used encoded a nucleic acid comprising a structure: S-ETD-MBD-IRES-R, wherein S encoded a B2M signal sequence (as provided by SEQ ID NO: 2), ETD encoded a variable extracellular targeting domain (e.g., the cancer-testis antigen NYESO-1); MBD encoded a membrane bound domain (e.g., MHC HLA-A2 domain), IRES encoded an internal ribosome entry site derived from encephalomyocarditis virus (EMCV), and R encoded a green fluorescent protein GFP reporter (FIG. 2).

The resulting viruses were harvested and purified by standard centrifugation techniques, prior to mixing (using pipette mixing) with T cell lines (e.g. Jurkat T cells) expressing T cell receptors (TCRs) specific to known pMHCs in the presence of hexadimethrine bromide.

Mixing HLA-A2-NYESO-1 pMHC-displaying viruses with Jurkat T cells expressing an IG4 T cell receptor (TCR) variant (SEQ ID NO: 27) that recognizes the displayed NYESO-1 with a binding affinity of ~26 pM, efficient infection was observed, with 41.9% of T cells expressing the GFP reporter after mixing (FIG. 3A). This result indicated that 41.9% of T cells in this cell population were infected by the virus. Conversely, mixing HLA-A2-NYESO-1 pMHC-displaying viruses were mixed with cells that did not express an IG4 TCR, minimal infection was observed, with only 1.1% of T cells expressing the GFP reporter after mixing (FIG. 3B).

Figure 4:
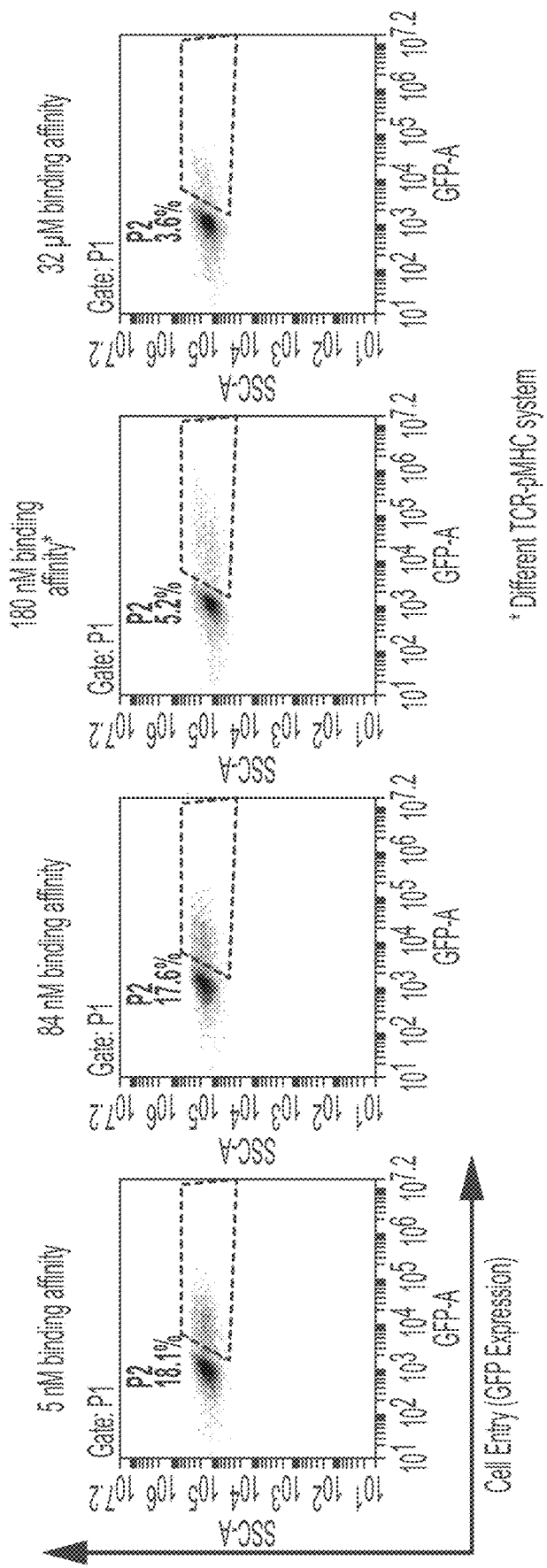

Mixing HLA-A2-NYESO-1 pMHC-displaying viruses with T cells expressing different versions of the IG4 TCR (wherein the different versions of the IG4 TCR exhibit reduced binding to the NYESO-1 antigen, compared to IG4 TCR variant comprising SEQ ID NO: 27) demonstrated that the viruses were able to infect T cells even when the binding affinity between the NYESO-1 antigen and IG4 TCR was down to 32 μM (FIG. 4). A 32 μM binding affinity between NYESO-1 antigen and an IG4 TCR variant (SEQ ID NO: 24) provided 3.6% transduction; a 84 nM binding affinity between NYESO-1 antigen and a IG4 TCR variant (SEQ ID NO: 25) provided 17.6% transduction; and a 5 nM binding affinity between NYESO-1 antigen and a IG4 TCR variant (SEQ ID NO: 26) provided 18.1% transduction; when measuring for GFP expression.

Figure 5B:
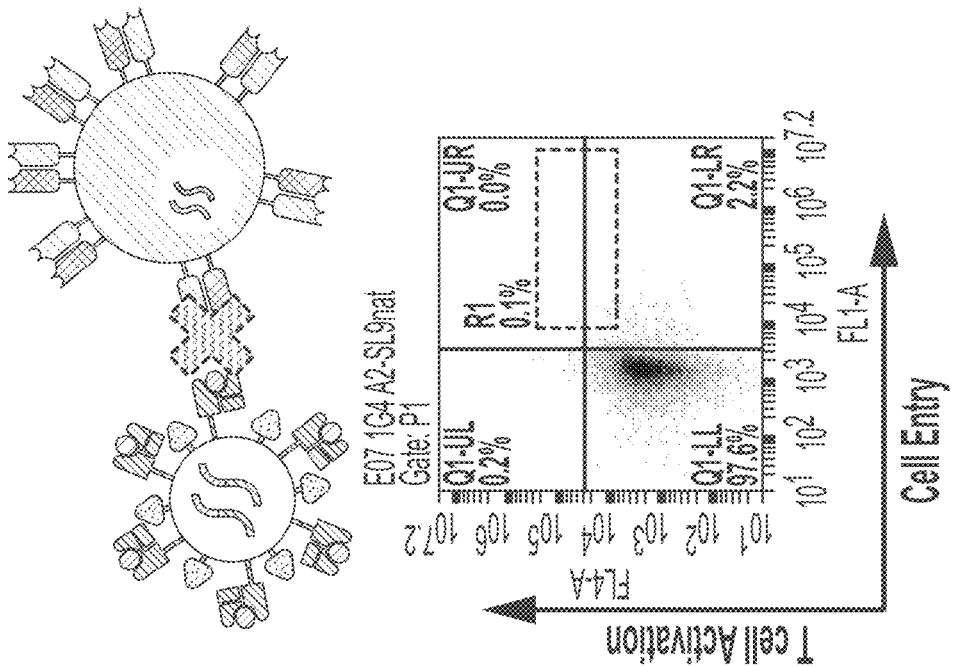
Figure 5A:
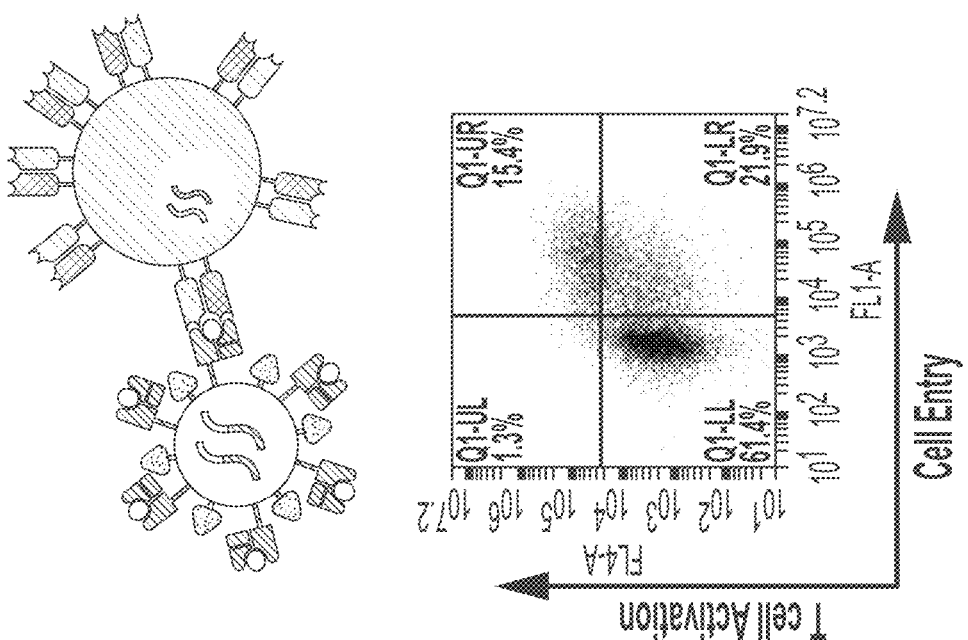
Figure 6:
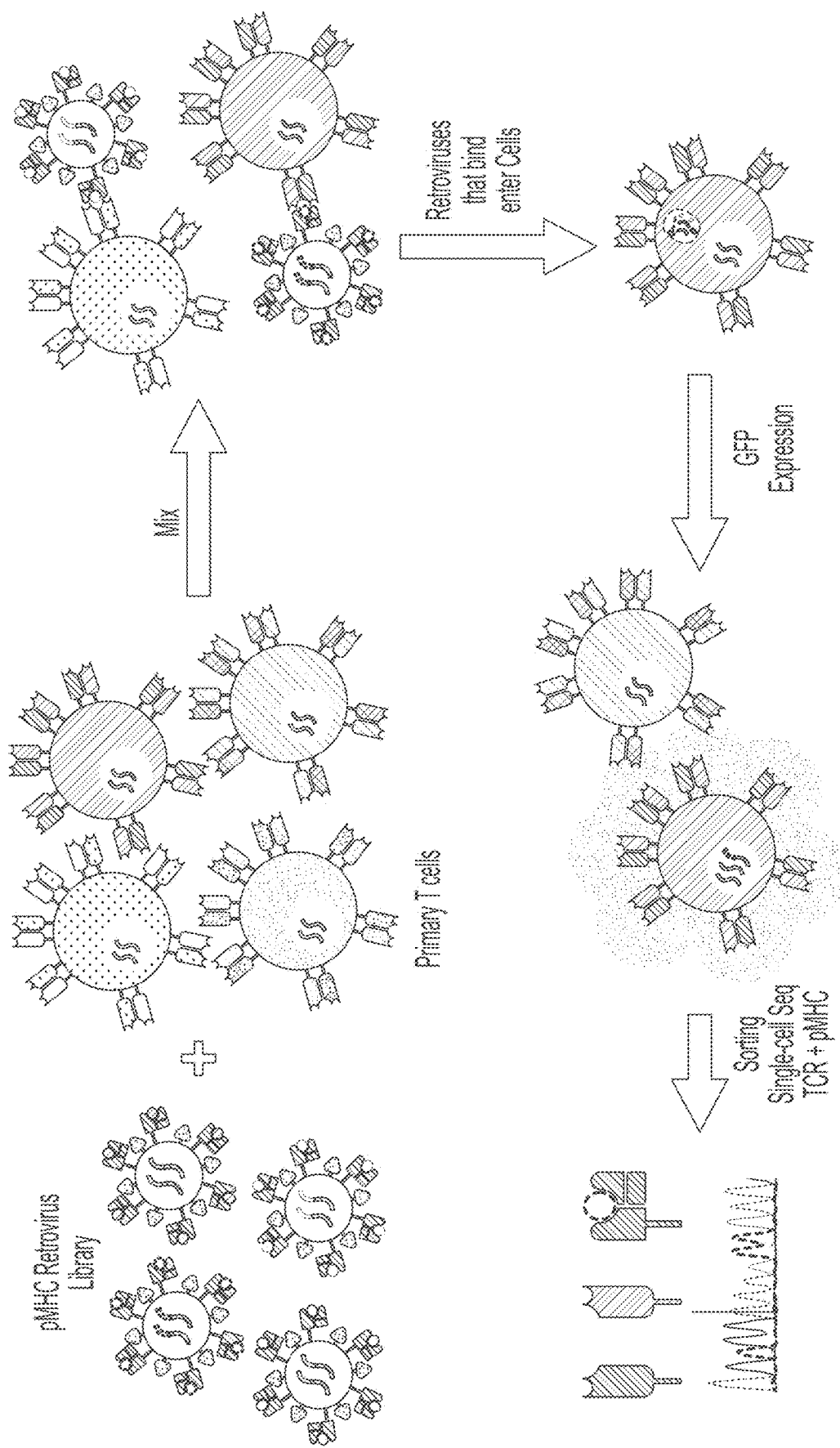
Figures 7A, 7B:
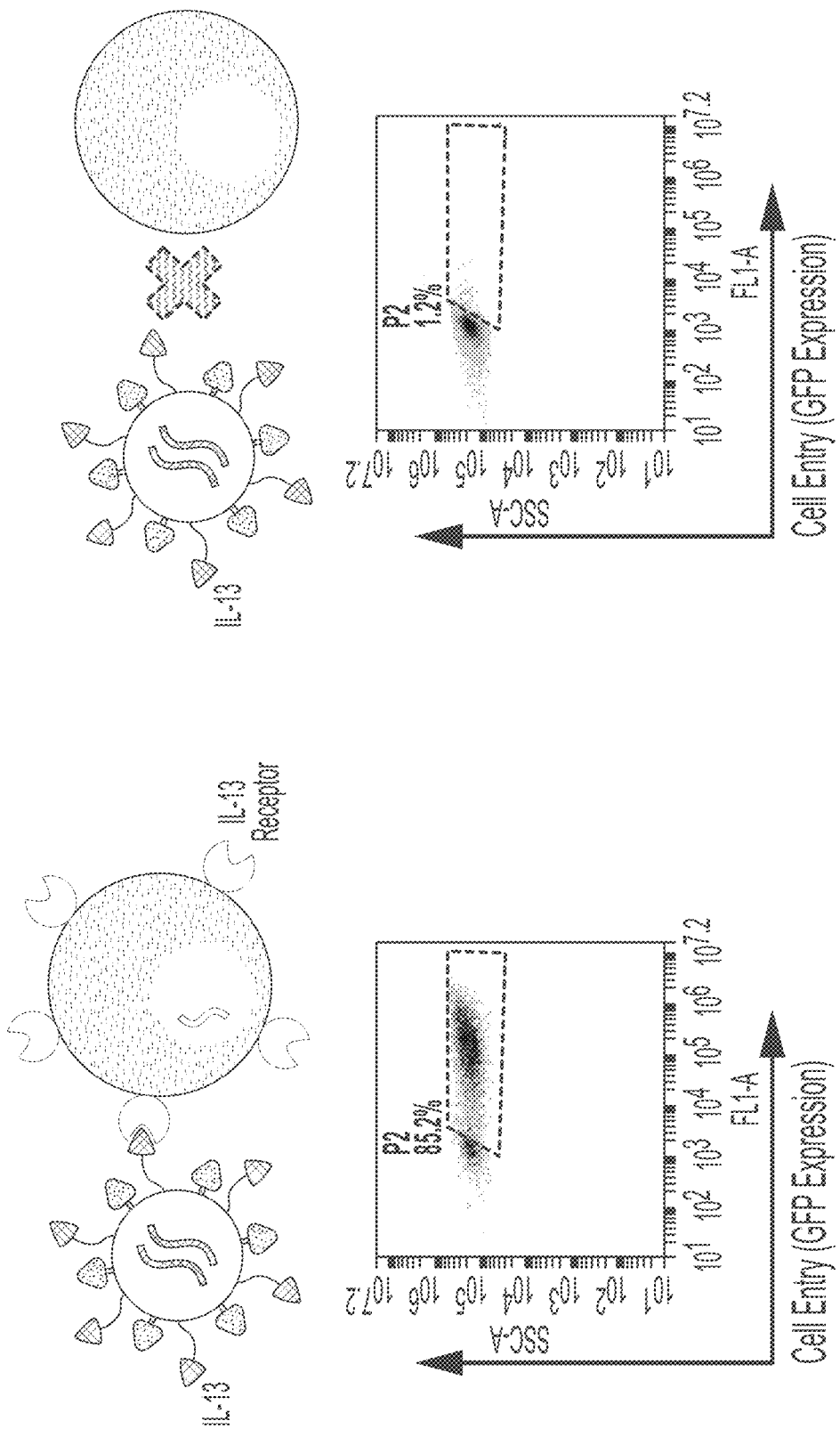
Figure 8:
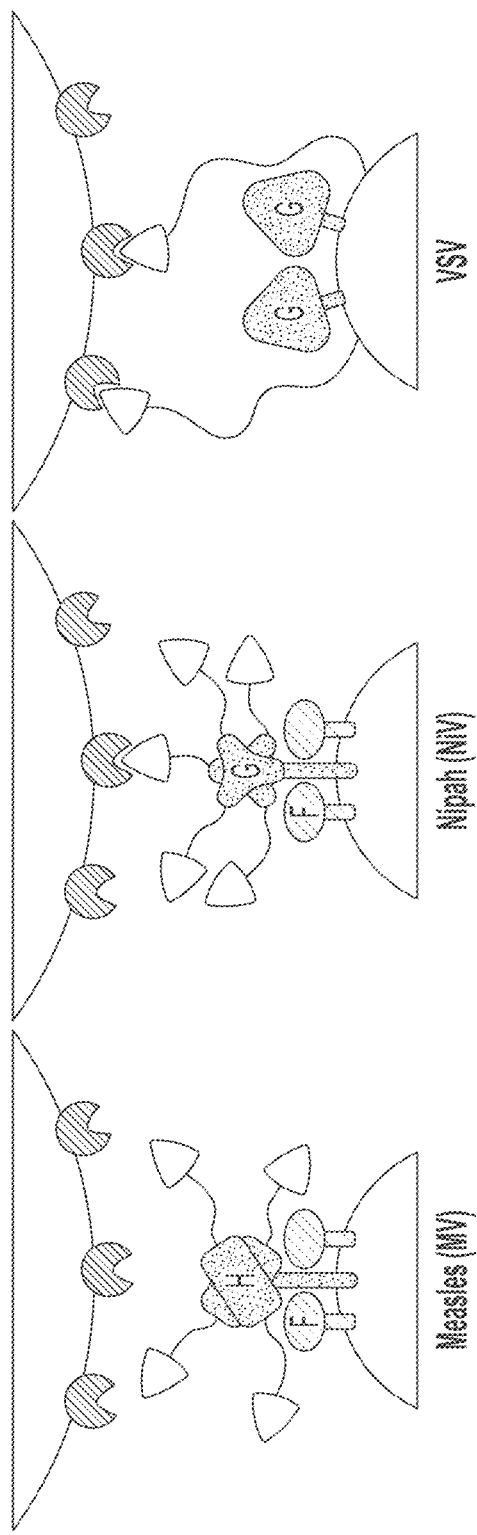
Figure 9:
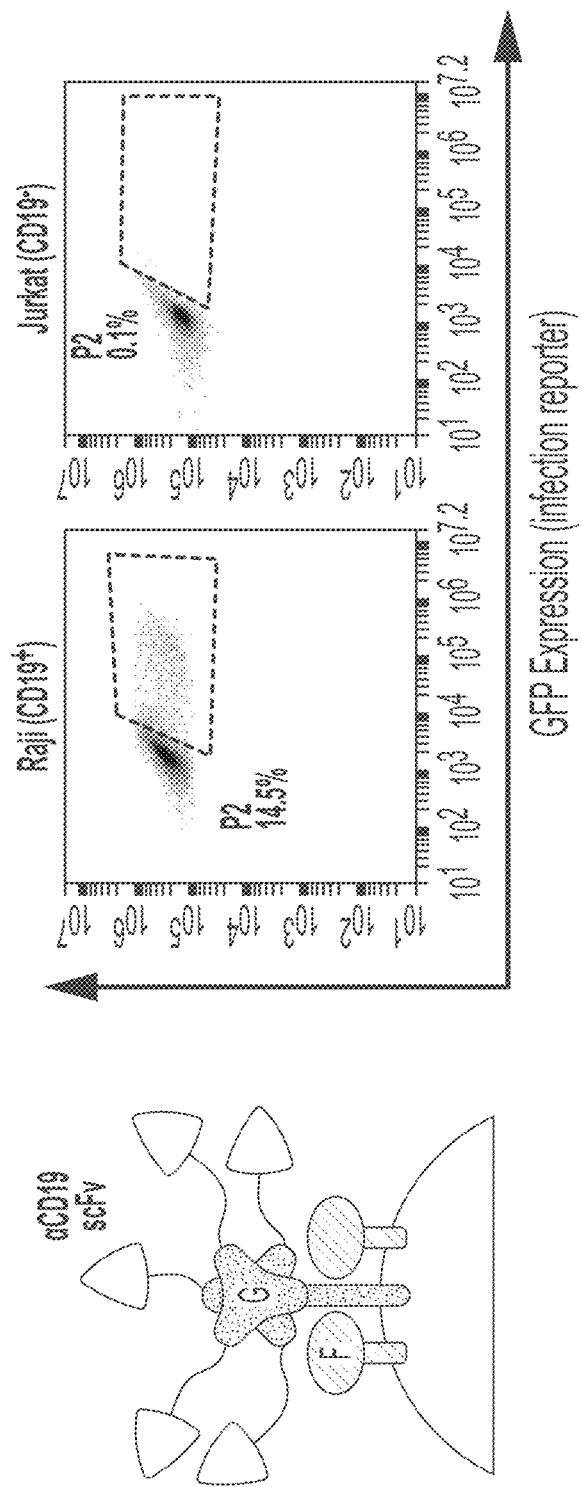
Figure 10B:
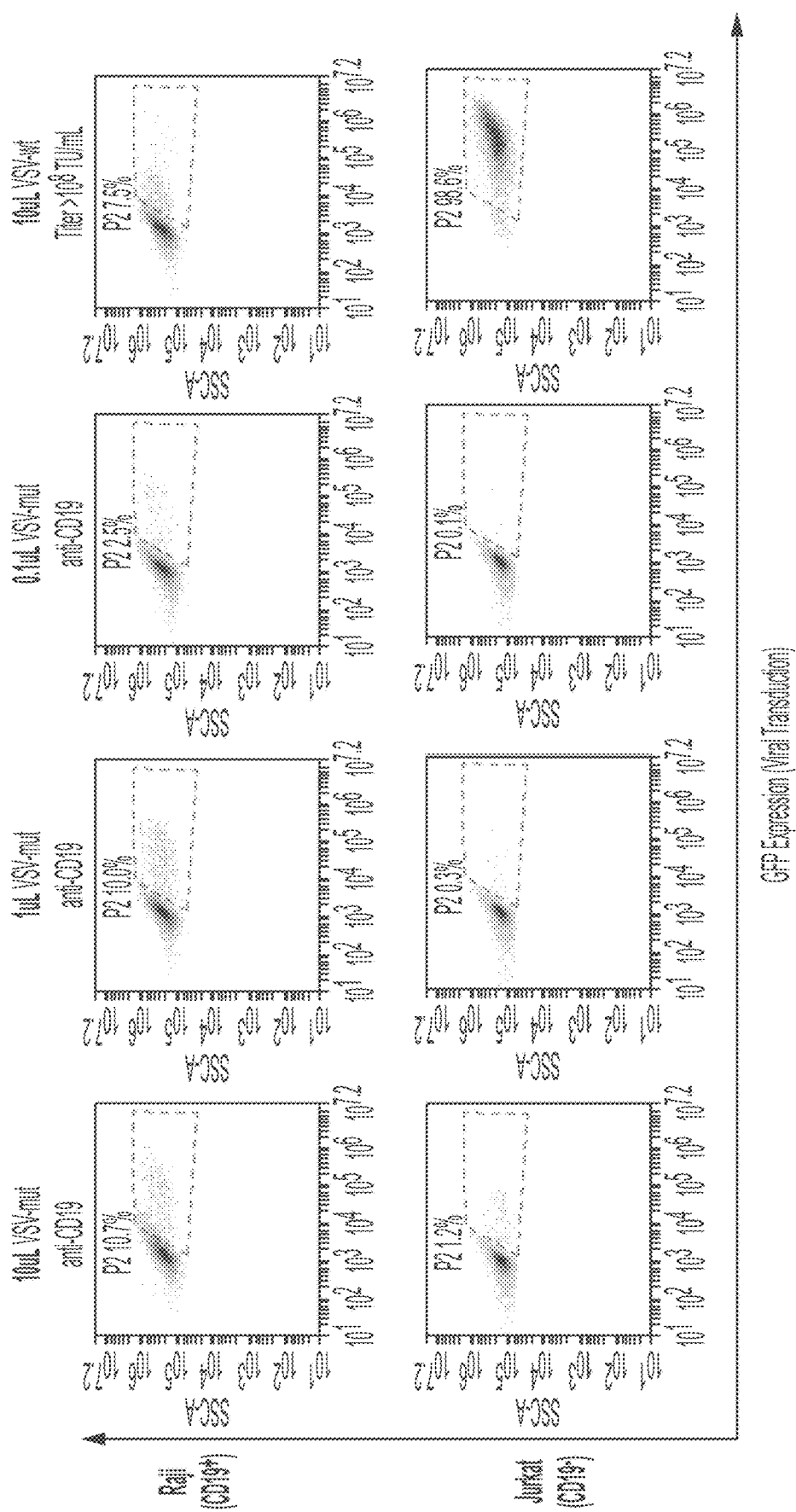
Figure 11:
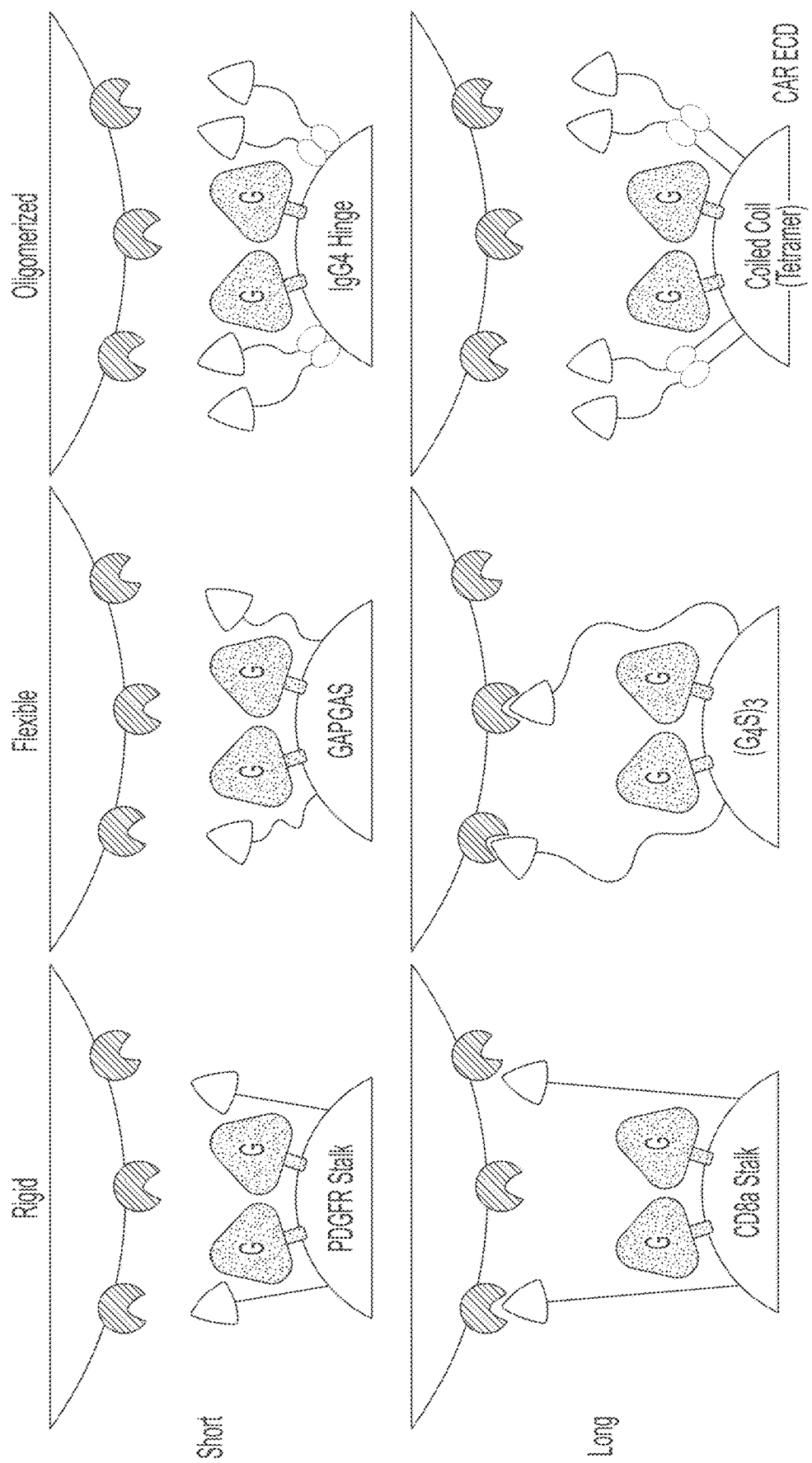
Figure 12:
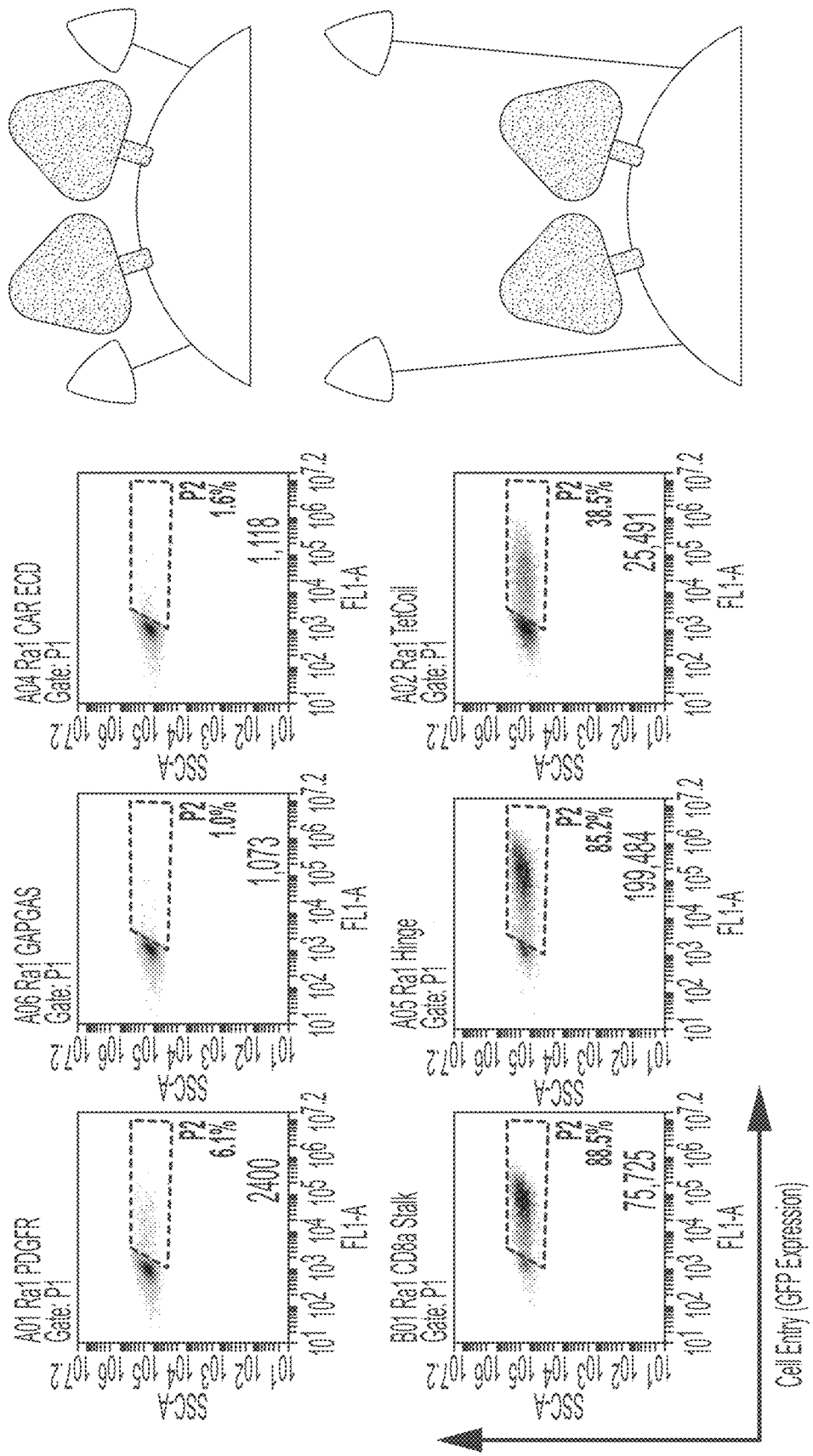
Figure 13:
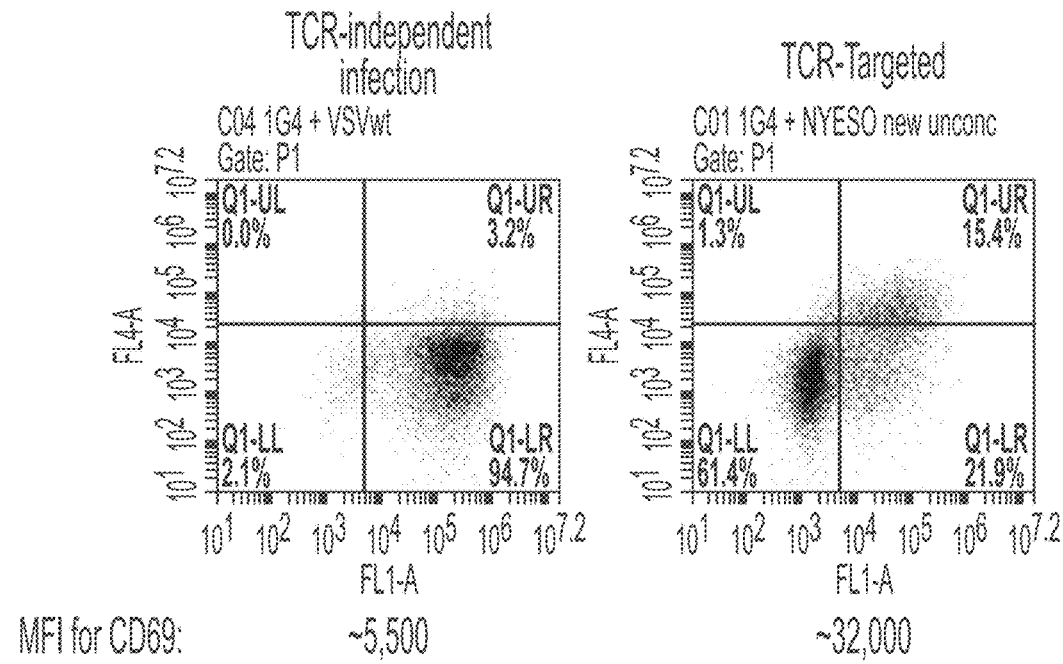
FIG. 13 depicts graphs showing that retroviruses comprising mutated VSV-G viral envelope proteins activate T cell signaling (right panel) and that retroviruses comprising wild-type VSV-G viral envelope proteins do not activate T cell signaling (left panel), as determined by expression of CD69.
Figure 14:
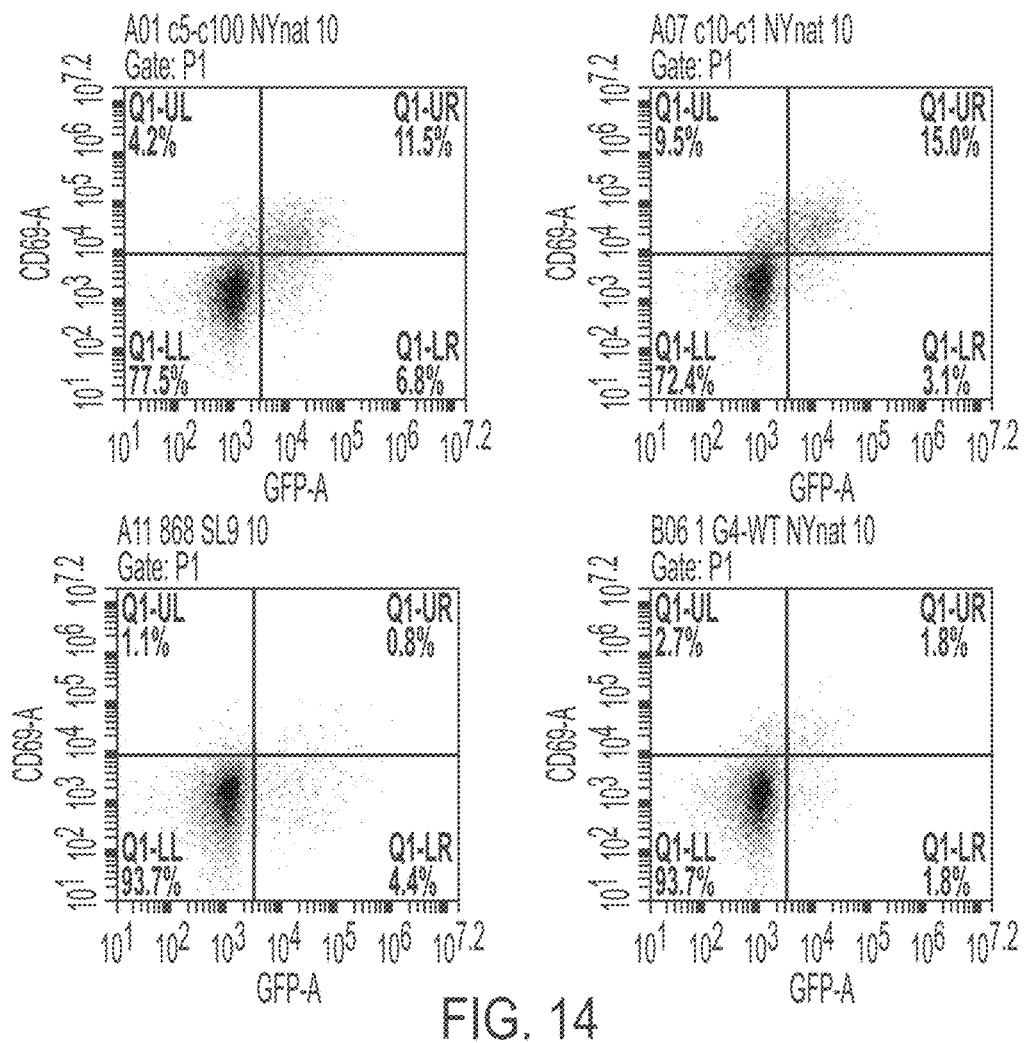
FIG. 14 depicts graphs showing that retroviruses having variable affinities between their extracellular targeting domains and a T cell cognate ligand are able to activate T cell signaling.
Figure 15:
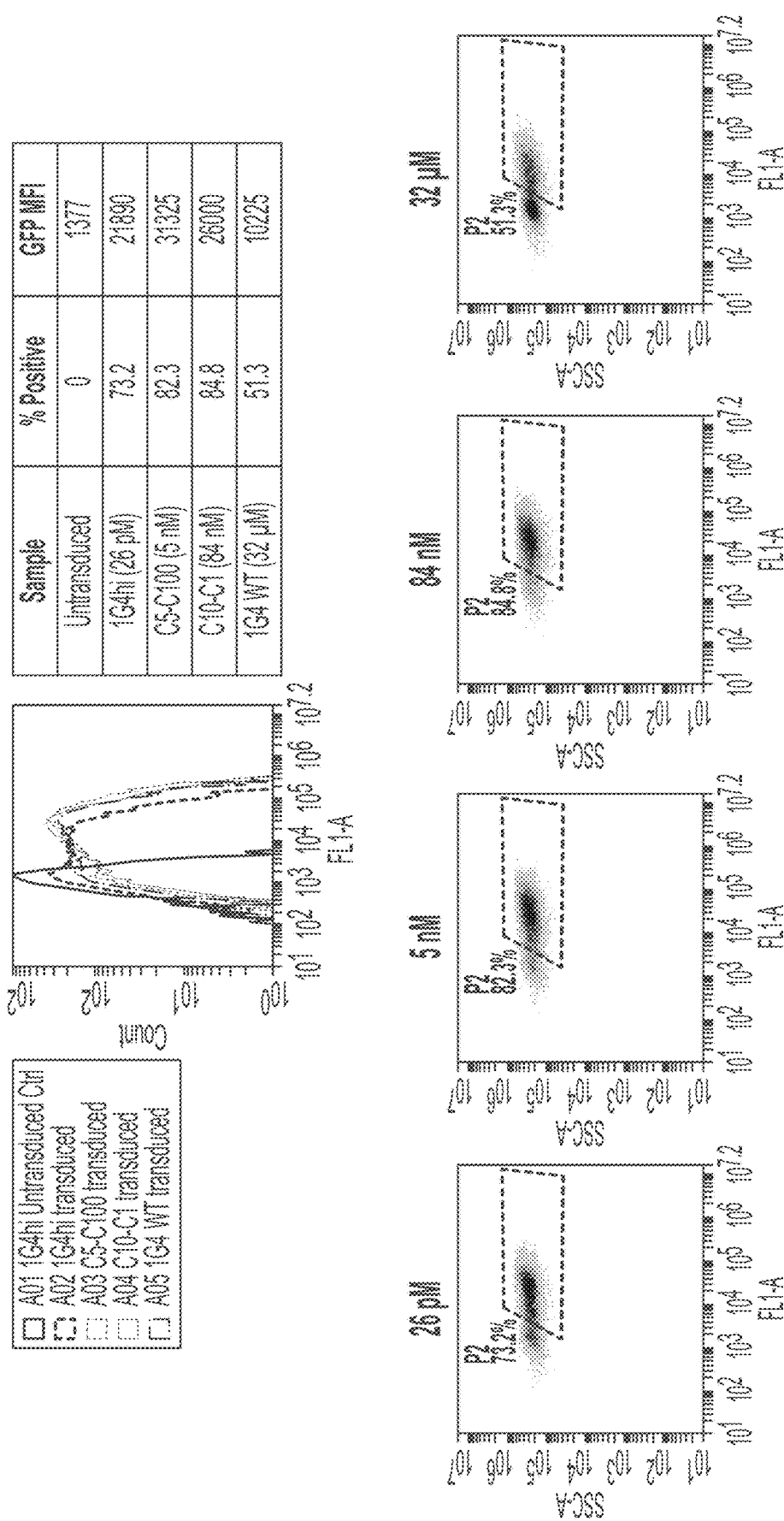
FIG. 15 depicts graphs showing the ability of retroviral entry into target cells at variable affinities, from picomolar to micromolar binding affinities, between an extracellular targeting domain and its cognate ligand.

1G4-expressing T cells exhibited T cell activation when transduced/infected with HLA-A2-NYESO-1-displaying viruses, as evidenced by upregulation of CD69 (FIG. 5A). Conversely, HLA-A2-SL9-displaying viruses did not transduce/infect nor activate 1G4-expressing T cells (FIG. 5B).

Example 2. Generation of Retroviruses that Target IL-13 Receptor

A lentivirus comprising an interleukin-13 (IL-13) extracellular targeting domain was generated, as described in Example 1. The IL-13 extracellular targeting domain consisted of full-length IL-13 protein connected to an IgG4 hinge linker protein linker and a PDGFR transmembrane domain comprising a truncated cytoplasmic tail (PDGFR transmembrane domain: VVVISAILALVVLTIISLIIL-IMLWQKKPR (SEQ ID NO: 28)). When the resultant viruses were mixed with Jurkat cells expressing the IL-13Rα1 receptor, efficient transduction was observed, with 85.2% of the cells expressing the GFP reporter after mixing (FIG. 7A). When the same viruses were mixed with cells not expressing any IL-13 receptors, minimal infection was observed (FIG. 7B).

Additional IL-13 expressing lentiviruses were generated with alternative protein linkers to connect the IL-13 extracellular targeting domain to the PDGFR transmembrane domain. Equivalent volumes of all lentiviruses tested were mixed with Jurkat cells bearing the IL13Rα1 receptor and transduction rates were assessed by GFP reporter (FIG. 12).

Short and long protein linkers were tested for their abilities to allow for cell-to-cell interactions between the extracellular targeting domain (IL-13) and the cognate ligand (IL13Rα1 receptor. Lentiviruses comprising short linkers were marginally able to infect Jurkat cells, with PDGFR linker (AVGQDTQEVIVVPHSLPFK (SEQ ID NO: 3)) enabling infection of 6.1% of cells; GAPGAS linker (GAPGAS (SEQ ID NO: 5)) enabling infection of 1.0% of cells; and a CAR ECD linker (ASESKYGPPCPPCP (SEQ ID NO: 10)) enabling infection of 1.6% of cells. Lentiviruses comprising long linkers were highly successful at infecting Jurkat cells, with CD8a stalk linker (ASAKPTTTPAPRPPTPAPTIASQPLSLRPEAARPAAGGAVHTRGLDFAK (SEQ ID NO: 4)) enabling infection of 88.5% of cells; IgG4 hinge linker (ASESKYGPPCPPCPAVGQDTQEVIVVPHSLPFK (SEQ ID NO: 8)) enabling infection of 85.2% of cells; and an oligomerized linker comprising an amino acid sequence that can form a tetrameric coiled coil (e.g., ASGGGGSGELAAIKQELAAIKKELAAIKWELAAIKQGAG (SEQ ID NO: 9)) enabling infection of 38.5% of cells.

Example 3. Generation of Retroviruses that Target CD19

A lentivirus pseudotyped with a Nipah virus F protein and a Nipah virus G protein fused to an anti-CD19 scFv was able to transduce $CD19^+$ Raji B cells (cells that express CD19), with 14.5% of cells expressing the GFP reporter after mixing (FIG. 9).

A lentivirus pseudotyped with VSV-mut (mutated VSV-G) and an anti-CD19 scFv fused to an IgG hinge domain, a truncated PDGFR stalk, and PDGFR transmembrane domain was able to transduce $CD19^+$ Raji B cells. Application of 1 μL of VSV-mut lentivirus (200× concentrated) to the $CD19^+$ Raji B cells provided 10.0% infected cells (based on expression of GFP reporter); 10 μL VSV-mut provided 10.7% infected cells. (FIG. 10). The same VSV-mut lentivirus construct did not transduce/infect $CD19^-$ Jurkat cells (cells that do not express CD19), demonstrating that the lentivirus is specific for cells expressing the cognate ligand of its extracellular targeting domain (anti-CD19 scFv).

A lentivirus pseudotyped with VSV-wt (wild-type VSV-G) and an anti-CD19 scFv fused to an IgG hinge domain, a truncated PDGFR stalk, and PDGFR transmembrane domain was able to transduce $CD19^+$ Raji B cells and $CD19^-$ Jurkat cells. This comparative result demonstrates the lentivirus comprising a mutated VSV-G (wherein the mutations diminish the native function of VSV-G protein) is selective for transducing/infecting cells that express a cognate ligand targeted by the extracellular targeting domain of the lentivirus.

Example 4. Ability of Targeted Lentiviruses to Induce T Cell Signaling

Viruses were assessed to determine whether infection via TCR targeting resulted in evidence of TCR signaling. While non-targeted VSV-wt viruses efficiently infected T cells, they did not activate T cells, as assessed by CD69 expression levels, compared to controls (FIG. 13, left panel). However, when HLA-A2-NYESO-1 displaying viruses were used to target Jurkat T cells expressing the high-affinity wild-type 1G4 TCR, upregulation of CD69 was observed in transduced cells, indicating TCR signaling occurred during infection (FIG. 13, right panel). These results were replicated when mixing HLA-A2-NYESO-1 displaying viruses with T cells expressing the lower-affinity mutant 1G4 TCR constructs described in Example 1 (FIG. 14)

Example 5. Lentiviral Transduction Through the TCR at Physiological Affinities A population of Jurkat T cells was purified on the basis of expression of IG4 TCR before being contacted with HLA-A2-NYESO-1 displaying viruses. The viruses efficiently transduced the purified populations of Jurkat T cells expressing each of the affinity variants of the 1G4 TCR, based on expression of the GFP reporter (FIG. 15). A 32 μM binding affinity between NYESO-1 antigen and an IG4 TCR variant provided 51.3% transduction; a 84 nM binding affinity between NYESO-1 antigen and an IG4 TCR variant provided 84.8% transduction; a 5 nM binding affinity between NYESO-1 antigen and an IG4 TCR variant provided 82.3% transduction; and a 26 nM binding affinity between NYESO-1 antigen and an IG4 TCR variant provided 73.2% transduction.

The differences among different IG4 TCR affinity variants were further investigated by performing a dose response to incubate varying amounts (0.5-10 μL of virus) of the HLA-A2-NYESO-1 displaying viruses with cells. NYESO-1 displaying lentiviruses transduce IG4-expressing T cells, even at high viral load (FIG. 16A). Conversely, SL-1 displaying lentiviruses (negative controls) do not transduce IG4-expressing T cells (SL-1 and IG4 TCR are not cognate binding partners).

The protein architecture of the membrane-bound NYESO-1 targeting protein was altered to test the ability of oligomerized NYESO-1 displaying constructs to transduce T cells. NYESO-1 displaying expressing lentiviruses were generated with alternative protein linkers to connect the NYESO-1 extracellular targeting domain to transmembrane domain were generated (a protein linker comprising the IgG4 hinge (dimer); and an oligomerized linker comprising an amino acid sequence that can form a tetrameric coiled coil (tetramer)). As demonstrated in FIG. 17, lentiviruses expressing these alternative architectures were able transduce T cells expressing the 26 PM and 32 μM IG4 TCR variants.

Example 6. Virus Binding Assay

Viruses were pseudotyped with either (1) wild-type VSV-G (VSV-G); (2) measles virus F protein and receptor-blinded H protein fused to an anti-CD19 scFv and a FLAG tag (MV-αCD19); (3) Nipah virus F protein and receptor-blinded G protein fused to an anti-CD19 scFv and a FLAG tag (NiV-aCD19); or (4) Nipah virus F and receptor-blinded G protein with a FLAG tag but no scFv (NiV-dead). Each of these viruses was mixed with $CD19^+$ Raji B cells and subsequently exposed to a fluorescently-labeled antibody against the FLAG tag. As demonstrated in FIGS. 18A-18B, the viruses that expressed an anti-CD19 scFv (MV-αCD19 and NiV-aCD19) bound to the Raji B cells. The viruses that did not express an anti-CD19 scFv (VSV-G and NiV-dead) did not bind to the Raji B cells.

Example 7. Screening a Library of Retroviruses Against Population of T Cells

A library of retroviruses ($10^7$-$10^{10}$ unique retroviruses) comprising a mutated VSV-G envelope protein, a non-viral membrane-bound protein comprising a MHC membrane-bound domain, a variable IL-13 extracellular targeting domain, and a GFP reporter.

First, a library of nucleic acids encoding unique non-viral membrane-bound proteins comprising a MHC membrane-bound domain and a variable IL-13 extracellular targeting domain, is prepared using PCR primers that include degenerate codons at positions known to interact with IL-13 receptors and induce random mutagenesis in the IL-13 extracellular targeting domain. The resulting nucleic acid constructs are assembled into viral transfer plasmids with fluorescent reporters by standard molecular cloning techniques. These plasmids ("transfer plasmids"), along with helper plasmids and an envelope plasmid encoding mutated VSV-G envelope protein (or an equivalent pseudotype) are transfected into retroviruses to generate the library of retroviruses. The viruses are purified and mixed with populations of cells (e.g. T cell lines, HEK293 cell lines) that express an IL-13 receptor of interest. The viruses are incubated with the populations of cells at an appropriate temperature (e.g., 37° C.) for an appropriate period of time (e.g., 1-48 hours). Mixing is performed in standard cell culture media with hexadimethrine bromide. After 24-48 hours, the cells are sorted based on the expression of the GFP reporter. High-expressing cells are retained and the sorting process is repeated as needed. After these rounds of selection by sorting, the retained cells are lysed and the cellular RNA and DNA are isolated for analysis using next-generation sequencing methods to determine which IL-13 variants were able to mediate viral entry.

Example 8. Generation of Additional Retroviruses that Targets Antigen-Specific T Cells Additional targeted lentiviruses were generated using the protocols described in Example 1.

As shown in FIG. 19, mixing (i) lentivirus comprising a mutated VSV-G envelope protein and pMHC displaying a SL9 peptide and (ii) 868 TCR-expressing T cells demonstrated that the viruses were able to transduce and infect T cells even at low amounts of added virus (~70% transduction at 1 µL of virus). Conversely, mixing of these viruses with off-target Jurkat cells led to low levels of transduction (less than 5% up to 10 µL of virus added). A similar experiment As also shown in FIG. 19, mixing (i) lentivirus comprising a mutated VSV-G envelope protein and pMHC displaying a cytomegalovirus (CMV) NLV peptide and (ii) C7 TCR-expressing T cells demonstrated that the viruses were able to transduce and infect T cells (~25% transduction at 10 µL of virus). Conversely, mixing of these viruses with off-target Jurkat cells led to low levels of transduction (less than 5% up to 10 µL of virus added).

Example 9. Generation of Retroviruses Comprising Targeted pMHCs Stabilized by Disulfides Additional targeted lentiviruses were generated using the protocols described in Example 1. These additional lentiviruses further comprised a disulfide situated within the pMHC in order to stabilize the structure of the pMHC.

As shown in FIG. 21, mixing (i) lentivirus comprising a mutated VSV-G envelope protein and a disulfide-stabilized pMHC displaying a targeting peptide and (ii) target cells expressing a cognate receptor demonstrated that the targeted viruses were able to transduce and infect target cells. Conversely, mixing of these targeted viruses with off-target cells caused no, or very limited (0.1%) transduction.

Specifically, a lentivirus comprising a disulfide-stabilized CMV NLV pMHC tranduced on-target C7 TCR-expressing T cells at a 21.8% transduction rate; a lentivirus comprising a disulfide-stabilized EBV pMHC tranduced on-target AS01 cells at a 4.8% transduction rate; a lentivirus comprising a disulfide-stabilized SL9 pMHC tranduced on-target 868 TCR-expressing T cells at a 22.1% transduction rate; and a lentivirus comprising a disulfide-stabilized NYESO-1 pMHC tranduced on-target IG4 TCR-expressing T cells at a 19.0% transduction rate.

Example 10. Targeted Viruses Transduce Primary Cells

A primary T cell line specific for GL9 (presented by HLA-A2) was specifically and efficiently transduced by viruses having a mutated VSV-G envelope protein and displaying GL9 (FIGS. 22A-22B). About 50% of primary T cells were transduced by these GL9-targeting viruses. Conversely, these GL9-targeting viruses only transduced 0.3% of IG4 TCR-expressing T cells. The IG4 TCR-expressing T cells were specifically and efficiently transduced by viruses having a mutated VSV-G envelope protein and displaying NYESO-1 (55.9% transduction). Furthermore, the targeted virus infects the primary cells more efficiently than a wild-type VSV-G virus. These results indicate that the targeted viruses can even infect unstimulated primary cells.

Similarly, a primary T cell line specific for NYESO (presented by HLA-A2) was specifically and efficiently transduced by viruses having a mutated VSV-G envelope protein and displaying NYESO-1 (FIGS. 23-24). Conversely, GL9-targeting viruses were unable to efficiently transduce the primary T cell line specific for NYESO. Collectively, these data demonstrate that primary NYESO-1-reactive cells, including expanded primary cells, can be specifically infected by NYESO-targeted viruses.

Example 11. Generation of Retroviruses Comprising CD80 Domain

A virus pseudotyped with a mutated VSV-G envelope protein and comprising a CD80 extracellular domain was generated using the protocol described in Example 1. This virus was able to specifically and efficiently infect Jurkat T cells (25.5% transduction), relative to B cells (0.0% transduction) (FIG. 25).

Similarly, a virus pseudotyped with a mutated VSV-G envelope protein and comprising a NYESO-1 pMHC and a CD80 extracellular domain was generated using the protocol described in Example 1. This virus was able to specifically and efficiently infect Jurkat T cells (13.5% transduction), relative to B cells (0.2% transduction) (FIG. 25). The presence of the CD80 domain enabled the transduction of this virus into the Jurkat T cells, as demonstrated by the inability of a virus a virus pseudotyped with a mutated VSV-G envelope protein and only comprising the NYESO-1 pMHC to infect these Jurkat T cells (0.9% transduction).

Collectively, these data show that the presence of CD80 on the virus surface mediates specific infection of T cells and demonstrates that CD80 could be used to generally target viruses to T cells.

Example 12. Murine Anti-CD3 Antibody Mediates Infection of TCR-Transduced 58−/− Cells Display of antibodies that are specific to the murine TCR constant region (H57 antibody) or the murine CD3 (2C11 antibody) on the surface of a virus enabled the virsues to infect mouse T cell lines. A virus comprising a mutated VSV-G viral envelope protein and the anti-TCR antibody provided 11.0% transduction of 58a B" mouse T hybridoma cells; and a virus comprising a mutated VSV-G viral envelope protein and the anti-CD3 antibody provided 12.8% transduction of 58a B" mouse T hybridoma cells.

Example 13. Generation of Viruses Comprising Dead Cocal Virus G Protein

A lentivirus was pseudotyped with a cocal virus G protein (Cocal-dead; amino acid comprising SEQ ID NO: 53) comprising mutations to reduce its infectivity. These mutations, at K64Q and R371A of the cocal virus G protein, were analogous to those mutations used in the VSV-dead variant described in Example 1. The cocal-dead virus further comprised a displayed anti-CD19 scFv antibody.

This cocal-dead virus was able to transduce CD19$^+$ Raji B cells (8.6% transduction), as shown in FIG. 27, in a similar manner as a lentivirus comprising VSV-dead protein and displayed anti-CD19 scFv antibody.

These data demonstrates that the viral targeting strategy is highly robust and that any viral envelope protein (e.g., mutated VSV-G, mutated Nipah envelope, mutated Measles envelope, mutated cocal viral envelope) that can be mutated to reduce its infectivity can be effectively used.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed.

Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

SEQUENCES
>Kappa leader sequence, amino acid
(SEQ ID NO: 1):
METDTLLLWVLLLWVPGSTG >B2M signal peptide sequence,
amino acid
(SEQ ID NO: 2):
MSRSVALAVLALLSLSGLEA >PDGFR short stalk, amino acid
(SEQ ID NO: 3):
AVGQDTQEVIVVPHSLPFK >PDGFR long stalk, amino acid
(SEQ ID NO: 4):
ASAKPTTTPAPRPPTPAPTIASQPLSL

RPEAARPAAGGAVHTRGLDFAK

>Short flexible linker, amino acid
(SEQ ID NO: 5):
GAPGAS

>Long flexible linker, amino acid
(SEQ ID NO: 6):
GAPGSGGGGSGGGGSAS

>Short flexible linker, amino acid
(SEQ ID NO: 7):
GGGGS

>IgG4 hinge domain, amino acid
(SEQ ID NO: 8):
ASESKYGPPCPPCPAVGQDTQEVIVVPHSLPFK >Tetrameric coiled coil, amino acid
(SEQ ID NO: 9):
ASGGGGSGELAAIKQELAAIKKELAAIKWELAAIKQGAG >Dimeric coiled coil, amino acid
(SEQ ID NO: 10):
ASESKYGPPCPPCP >Wild-type VSV-G envelope protein
(with leader sequence),
DNA sequence
(SEQ ID NO: 11):
atgaagtgccttttgtacttagcctttttattcattggggtgaat tgcaagttcaccatagttttccacacaaccaaaaaggaaactgg aaaaatgttccttctaattaccattattgcccgtcaagctcagat ttaaattggcataatgacttaataggcacagccatacaagtcaaa atgcccaagagtcacaaggctattcaagcagacggttggatgtgt catgcttccaaatgggtcactacttgtgatttcgctggtatgga ccgaagtatataacacagtccatccgatccttcactccatctgta gaacaatgcaaggaaagcattgaacaaacgaaacaaggaacttgg ctgaatccaggcttccctcctcaaagttgtggatatgcaactgtg acggatgccgaagcagtgattgtccaggtgactcctcaccatgtg ctggttgatgaatacacaggagaatgggttgattcacagttcatc aacggaaaatgcagcaattacatatgccccactgtccataactct acaacctggcattctgactataaggtcaaagggctatgtgattct aacctcatttccatggacatcaccttcttctcagaggacggagag ctatcatccctgggaaaggagggcacaggggttcagaagtaactac tttgcttatgaaactggaggcaaggcctgcaaaatgcaatactgc aagcattggggagtcagactcccatcaggtgtctggttcgagatg gctgataaggatctctttgctgcagcagattccctgaatgccca gaagggtcaagtatctctgctccatctcagacctcagtggatgta agtctaattcaggacgttgagaggatcttggattattccctctgc caagaaacctggagcaaaatcagagcgggtcttccaatctctcca gtggatctcagctatcttgctcctaaaaacccaggaaccggtcct gcttcaccataatcaatggtaccctaaaatactttgagaccaga tacatcagagtcgatattgctgctccaatcctctcaagaatggtc ggaatgatcagtggaactaccacagaaagggaactgtgggatgac tgggcaccatatgaagacgtggaaattggacccaatggagttctg aggaccagttcaggatataagtttcctttatacatgattggacat ggtatgttggactccgatcttcatcttagctcaaaggctcaggtg ttcgaacatcctcacattcaagacgctgcttcgcaacttcctgat gatgagagtttattttttggtgatactgggctatccaaaaatcca atcgagcttgtagaaggttggttcagtagttggaaaagctctatt gcctcttttttctttatcatagggttaatcattggactattcttg gttctccgagttggtatccatctttgcattaaattaaagcacacc aagaaaagacagatttatacagacatagagatgaaccgacttgga aagtaa >Wild-type VSV-G envelope protein
(with leader sequence), amino
acid sequence
(SEQ ID NO: 12):
MKCLLYLAFLFIGVNCKFTIVFPHNQKGNWKNVPSNYHYCPSSSD

LNWHNDLIGTAIQVKMPKSHKAIQADGWMCHASKWVTTCDFRWYG

PKYITQSIRSFTPSVEQCKESIEQTKQGTWLNPGFPPQSCGYATV

TDAEAVIVQVTPHHVLVDEYTGEWVDSQFINGKCSNYICPTVHNS

TTWHSDYKVKGLCDSNLISMDITFFSEDGELSSLGKEGTGFRSNY

FAYETGGKACKMQYCKHWGVRLPSGVWFEMADKDLFAAARFPECP

EGSSISAPSQTSVDVSLIQDVERILDYSLCQETWSKIRAGLPISP

VDLSYLAPKNPGTGPAFTIINGTLKYFETRYIRVDIAAPILSRMV

GMISGTTTERELWDDWAPYEDVEIGPNGVLRTSSGYKFPLYMIGH

-continued

GMLDSDLHLSSKAQVFEHPHIQDAASQLPDDESLFFGDTGLSKNP
IELVEGWFSSWKSSIASFFFIIGLIIGLFLVLRVGIHLCIKLKHT
KKRQIYTDIEMNRLGK

>Wild-type VSV-G envelope protein,
amino acid sequence
(SEQ ID NO: 13):
KFTIVFPHNQKGNWKNVPSNYHYCPSSSDLNWHNDLIGTAIQVKM
PKSHKAIQADGWMCHASKWVTTCDFRWYGPKYITQSIRSFTPSVE
QCKESIEQTKQGTWLNPGFPPQSCGYATVTDAEAVIVQVTPHHVL
VDEYTGEWVDSQFINGKCSNYICPTVHNSTTWHSDYKVKGLCDSN
LISMDITFFSEDGELSSLGKEGTGFRSNYFAYETGGKACKMQYCK
HWGVRLPSGVWFEMADKDLFAAARFPECPEGSSISAPSQTSVDVS
LIQDVERILDYSLCQETWSKIRAGLPISPVDLSYLAPKNPGTGPA
FTIINGTLKYFETRYIRVDIAAPILSRMVGMISGTTTERELWDDW
APYEDVEIGPNGVLRTSSGYKFPLYMIGHGMLDSDLHLSSKAQVF
EHPHIQDAASQLPDDESLFFGDTGLSKNPIELVEGWFSSWKSSI
ASFFFIIGLIIGLFLVLRVGIHLCIKLKHTKKRQIYTDIEMNRLG
K >VSV-G envelope protein (with leader
sequence), DNA sequence
(SEQ ID NO: 14):
atgaagtgccttttgtacttagccttttttattcattggggtgaat
tgcaagttcaccatagttttttccacacaaccaaaaggaaactgg
aaaaatgttccttctaattaccattattgcccgtcaagctcagat
ttaaattggcataatgacttaataggcacagccttacaagtcaaa
atgccccagagtcacaaggctattcaagcagacggttggatgtgt
catgcttccaaatgggtcactacttgtgatttccgctggtatgga
ccgaagtatataacacagtccatccgatccttcactccatcgta
gaacaatgcaaggaaagcattgaacaaacgaaacaaggaacttgg
ctgaatccaggcttccctcctcaaagttgtggatatgcaactgtg
acggatgccgaagcagtgattgtccaggtgactcctcaccatgtg
ctggttgatgaatacacaggagaatgggttgattcacagttcatc
aacggaaaatgcagcaattacatatgccccactgtccataactct
acaacctggcattctgactataaggtcaaagggctatgtgattct
aacctcatttccatggacatcaccttcttctcagaggacggagag
ctatcatccctgggaaaggagggcacagggttcagaagtaactac
tttgcttatgaaactggaggcaaggcctgcaaaatgcaatactgc
aagcattggggagtcagactcccatcaggtgtctggttcgagatg
gctgataaggatctcttttgctgcagccagattccctgaatgccca
gaagggtcaagtatctctgctccatctcagacctcagtggatgta
agtctaattcaggacgttgagaggatcttggattattccctctgc
caagaaacctggagcaaaatcagagcgggtcttccaatctctcca
gtggatctcagctatcttgctcctaaaaacccaggaaccggtcct gctttcaccataatcaatggtacccctaaaatactttgagaccaga
tacatcagagtcgatattgctgctccaatcctctcaagaatggtc
ggaatgatcagtggaactaccacagaagccgaactgtgggatgac
tgggcaccatatgaagacgtggaaattgacccaatggagttctg
aggaccagttcaggatataagtttcctttatacatgattggacat
ggtatgttggactccgatcttcatcttagctcaaaggctcaggtg
ttcgaacatcctcacattcaagacgctgcttcgcaacttcctgat
gatgagagtttatttttggtgatactgggctatccaaaaatcca
atcgagcttgtagaaggttggttcagtagttggaaaagctctatt
gcctcttttttctttatcataggttaatcattggactattcttg
gttctccgagttggtatccatctttgcattaaattaaagcacacc
aagaaaagacagatttatacagacatagagatgaaccgacttgga
aagtaa >VSV-G envelope protein (with leader sequence),
amino acid sequence
(SEQ ID NO: 15):
MKCLLYLAFLFIGVNCKFTIVFPHNQKGNWKNVPSNYHYCPSSSD
LNWHNDLIGTALQVKMPQSHKAIQADGWMCHASKWVTTCDFRWYG
PKYITQSIRSFTPSVEQCKESIEQTKQGTWLNPGFPPQSCGYATV
TDAEAVIVQVTPHHVLVDEYTGEWVDSQFINGKCSNYICPTVHNS
TTWHSDYKVKGLCDSNLISMDITFFSEDGELSSLGKEGTGFRSNY
FAYETGGKACKMQYCKHWGVRLPSGVWFEMADKDLFAAARFPECP
EGSSISAPSQTSVDVSLIQDVERILDYSLCQETWSKIRAGLPISP
VDLSYLAPKNPGTGPAFTIINGTLKYFETRYIRVDIAAPILSRMV
GMISGTTTEAELWDDWAPYEDVEIGPNGVLRTSSGYKFPLYMIGH
GMLDSDLHLSSKAQVFEHPHIQDAASQLPDDESLFFGDTGLSKNP
IELVEGWFSSWKSSIASFFFIIGLIIGLFLVLRVGIHLCIKLKHT
KKRQIYTDIEMNRLGK >141L/K47Q/R354A VSV-G envelope protein,
amino acid sequence
(SEQ ID NO: 16):
KFTIVFPHNQKGNWKNVPSNYHYCPSSSDLNWHNDLIGTALQVKM
PQSHKAIQADGWMCHASKWVTTCDFRWYGPKYITQSIRSFTPSVE
QCKESIEQTKQGTWLNPGFPPQSCGYATVTDAEAVIVQVTPHHVL
VDEYTGEWVDSQFINGKCSNYICPTVHNSTTWHSDYKVKGLCDSN
LISMDITFFSEDGELSSLGKEGTGFRSNYFAYETGGKACKMQYCK
HWGVRLPSGVWFEMADKDLFAAARFPECPEGSSISAPSQTSVDVS
LIQDVERILDYSLCQETWSKIRAGLPISPVDLSYLAPKNPGTGPA
FTIINGTLKYFETRYIRVDIAAPILSRMVGMISGTTTEAELWDDW
APYEDVEIGPNGVLRTSSGYKFPLYMIGHGMLDSDLHLSSKAQVF
EHPHIQDAASQLPDDESLFFGDTGLSKNPIELVEGWFSSWKSSI
ASFFFIIGLIIGLFLVLRVGIHLCIKLKHTKKRQIYTDIEMNRLG
K >K47Q/R354A VSV-G envelope protein,
amino acid sequence
(SEQ ID NO: 17):
KFTIVFPHNQKGNWKNVPSNYHYCPSSSDLNWHNDLIGTAIQVKM
PQSHKAIQADGWMCHASKWVTTCDFRWYGPKYITQSIRSFTPSVE
QCKESIEQTKQGTWLNPGFPPQSCGYATVTDAEAVIVQVTPHHVL
VDEYTGEWVDSQFINGKCSNYICPTVHNSTTWHSDYKVKGLCDSN
LISMDITFFSEDGELSSLGKEGTGFRSNYFAYETGGKACKMQYCK
HWGVRLPSGVWFEMADKDLFAAARFPECPEGSSISAPSQTSVDVS
LIQDVERILDYSLCQETWSKIRAGLPISPVDLSYLAPKNPGTGPA
FTIINGTLKYFETRYIRVDIAAPILSRMVGMISGTTTEAELWDDW
APYEDVEIGPNGVLRTSSGYKFPLYMIGHGMLDSDLHLSSKAQVF
EHPHIQDAASQLPDDESLFFGDTGLSKNPIELVEGWFSSWKSSI
ASFFFIIGLIIGLFLVLRVGIHLCIKLKHTKKRQIYTDIEMNRLG
K >Exemplary wild-type measles envelope protein (with leader sequence), DNA sequence (SEQ ID NO: 18):

ATGGGCAGCCGGATCGTGATCAACCGGGAGCACCTGATGATCGAC
CGGCCCTACGTGCTGCTGGCCGTGCTGTTCGTGATGTTCCTGAGC
CTGATCGGCTTGCTAGCCATTGCTGGAATCCGGCTGCACAGAGCC
GCCATCTACACCGCCGAGATCCACAAGAGCCTGAGCACCAACCTG
GACGTGACCAACAGCATCGAGCATCAGGTCAAGGACGTGCTGACC
CCCCTGTTTAAGATCATCGGCGACGAAGTGGGCCTGCGGACCCCC
CAGAGATTCACCGACCTGGTCAAGTTCATCAGCGACAAGATCAAG
TTCCTGAACCCCGACCGGGAGTACGACTTCCGGGACCTGACCTGG
TGCATCAACCCCCCCGAGCGGATCAAGCTGGACTACGACCAGTAC
TGCGCCGATGTGGCCGCCGAGGAACTGATGAATGCATTGGTGAAC
TCAACTCTACTGGAGACCAGAACAACCAATCAGTTCCTAGCTGTC
TCAAAGGGAAACTGCTCAGGGCCCACTACAATCAGAGGTCAATTC
TCAAACATGTCGCTGTCCCTGTTAGACTTGTATTTAGGTCGAGGT
TACAATGTGTCATCTATAGTCACTATGACATCCCAGGGAATGTAT
GGGGGAACTTACCTAGTGGAAAAGCCTAATCTGAGCAGCAAAAGG
TCAGAGTTGTCACAACTGAGCATGTACCGAGTGTTTGAAGTAGGT
GTTATCAGAAATCCGGGTTTGGGGGCTCCGGTGTTCCATATGACA
AACTATCTTGAGCAACCAGTCAGTAATGATCTCAGCAACTGTATG
GTGGCTTTGGGGGAGCTCAAACTCGCAGCCCTTTGTCACGGGGAA
GATTCTATCACAATTCCCTATCAGGGATCAGGGAAAGGTGTCAGC
TTCCAGCTCGTCAAGCTAGGTGTCTGGAAATCCCCAACCGACATG
CAATCCTGGGTCCCCTTATCAACGGATGATCCAGTGATAGACAGG
CTTTACCTCTCATCTCACAGAGGTGTTATCGCTGACAACCAAGCA
AAATGGGCTGTCCCGACAACACGAACAGATGACAAGTTGCGAATG
GAGACATGCTTCCAACAGGCGTGTAAGGGTAAAATCCAAGCACTC

-continued

TGCGAGAATCCCGAGTGGGCACCATTGAAGGATAACAGGATTCCT
TCATACGGGGTCTTGTCTGTTGATCTGAGTCTGACAGTTGAGCTT
AAAATCAAAATTGCTTCGGGATTCGGGCCATTGATCACACACGGT
TCAGGGATGGACCTATACAAATCCAACCACAACAATGTGTATTGG
CTGACTATCCCGCCAATGAAGAACCTAGCCTTAGGTGTAATCAAC
ACATTGGAGTGGATACCGAGATTCAAGGTTAGTCCCtatCTCTTC
AcaGTCCCAATTAAGGAAGCAGGCGGAGACTGCCATGCCCCAACA
TACCTACCTGCGGAGGTGGATGGTGATGTCAAACTCAGTTCCAAT
CTGGTGATTCTACCTGGTCAAGATCTCCAATATGTTTTGGCAACC
TACGATACTTCCcgGGTTGAACATGCTGTGGTTTATTACGTTTAC
AGCCCAAGCCGCTCATTTTCTTACTTTTATCCTTTTAGGTTGCCT
ATAAAGGGGGTCCCCATCGAATTACAAGTGGAATGCTTCACATGG
GACCAAAAACTCTGGTGCCGTCACTTCTGTGTGCTTGCGGACTCA
GAATCTGGTGGACATATCACTCACTCTGGGATGGTGGGCATGGGA
GTCAGCTGCACAGTCACCCGGGAAGATGGAACCAATGACTACAAA
GACGATGACGACAAGTGA >Exemplary wild-type measles envelope protein, amino acid sequence (SEQ ID NO: 19):

MGSRIVINREHLMIDRPYVLLAVLFVMFLSLIGLLAIAGIRLHRA
AIYTAEIHKSLSTNLDVTNSIEHQVKDVLTPLFKIIGDEVGLRTP
QRFTDLVKFISDKIKFLNPDREYDFRDLTWCINPPERIKLDYDQY
CADVAAEELMNALVNSTLLETRTTNQFLAVSKGNCSGPTTIRGQF
SNMSLSLLDLYLGRGYNVSSIVTMTSQGMYGGTYLVEKPNLSSKR
SELSQLSMYRVFEVGVIRNPGLGAPVFHMTNYLEQPVSNDLSNCM
VALGELKLAALCHGEDSITIPYQGSGKGVSFQLVKLGVWKSPTDM
QSWVPLSTDDPVIDRLYLSSHRGVIADNQAKWAVPTTRTDDKLRM
ETCFQQACKGKIQALCENPEWAPLKDNRIPSYGVLSVDLSLTVEL
KIKIASGFGPLITHGSGMDLYKSNHNNVYWLTIPPMKNLALGVIN
TLEWIPRFKVSPYLFTVPIKEAGGDCHAPTYLPAEVDGDVKLSSN
LVILPGQDLQYVLATYDTSRVEHAVVYYVYSPSRSFSYFYPFRLP
IKGVPIELQVECFTWDQKLWCRHFCVLADSESGGHITHSGMVGMG
VSCTVTREDGTNDYKDDDDK

>Exemplary mutant measles envelope protein, DNA sequence (SEQ ID NO: 20):

ATGGGCAGCCGGATCGTGATCAACCGGGAGCACCTGATGATCGAC
CGGCCCTACGTGCTGCTGGCCGTGCTGTTCGTGATGTTCCTGAGC
CTGATCGGCTTGCTAGCCATTGCTGGAATCCGGCTGCACAGAGCC
GCCATCTACACCGCCGAGATCCACAAGAGCCTGAGCACCAACCTG
GACGTGACCAACAGCATCGAGCATCAGGTCAAGGACGTGCTGACC
CCCCTGTTTAAGATCATCGGCGACGAAGTGGGCCTGCGGACCCCC
CAGAGATTCACCGACCTGGTCAAGTTCATCAGCGACAAGATCAAG

-continued
TTCCTGAACCCCGACCGGGAGTACGACTTCCGGGACCTGACCTGG

TGCATCAACCCCCCGAGCGGATCAAGCTGGACTACGACCAGTAC

TGCGCCGATGTGGCCGCCGAGGAACTGATGAATGCATTGGTGAAC

TCAACTCTACTGGAGACCAGAACAACCAATCAGTTCCTAGCTGTC

TCAAAGGGAAACTGCTCAGGGCCCACTACAATCAGAGGTCAATTC

TCAAACATGTCGCTGTCCCTGTTAGACTTGTATTTAGGTCGAGGT

TACAATGTGTCATCTATAGTCACTATGACATCCCAGGGAATGTAT

GGGGGAACTTACCTAGTGGAAAAGCCTAATCTGAGCAGCAAAAGG

TCAGAGTTGTCACAACTGAGCATGTACCGAGTGTTTGAAGTAGGT

GTTATCAGAAATCCGGGTTTGGGGGCTCCGGTGTTCCATATGACA

AACTATCTTGAGCAACCAGTCAGTAATGATCTCAGCAACTGTATG

GTGGCTTTGGGGGAGCTCAAACTCGCAGCCCTTTGTCACGGGGAA

GATTCTATCACAATTCCCTATCAGGGATCAGGGAAAGGTGTCAGC

TTCCAGCTCGTCAAGCTAGGTGTCTGGAAATCCCCAACCGACATG

CAATCCTGGGTCCCCTTATCAACGGATGATCCAGTGATAGACAGG

CTTTACCTCTCATCTCACAGAGGTGTTATCGCTGACAACCAAGCA

AAATGGGCTGTCCCGACAACACGAACAGATGACAAGTTGCGAATG

GAGACATGCTTCCAACAGGCGTGTAAGGGTAAAATCCAAGCACTC

TGCGAGAATCCCGAGTGGGCACCATTGAAGGATAACAGGATTCCT

TCATACGGGGTCTTGTCTGTTGATCTGAGTCTGACAGTTGAGCTT

AAAATCAAAATTGCTTCGGGATTCGGGCCATTGATCACACACGGT

TCAGGGATGGACCTATACAAATCCAACCACAACAATGTGTATTGG

CTGACTATCCCGCCAATGAAGAACCTAGCCTTAGGTGTAATCAAC

ACATTGGAGTGGATACCGAGATTCAAGGTTAGTCCCGCGCTCTTC

AATGTCCCAATTAAGGAAGCAGGCGGAGACTGCCATGCCCCAACA

TACCTACCTGCGGAGGTGGATGGTGATGTCAAACTCAGTTCCAAT

CTGGTGATTCTACCTGGTCAAGATCTCCAATATGTTTTGGCAACC

TACGATACTTCCGCGGTTGAACATGCTGTGGTTTATTACGTTTAC

AGCCCAAGCCGCTCATTTTCTTACTTTTATCCTTTTAGGTTGCCT

ATAAAGGGGGTCCCCATCGAATTACAAGTGGAATGCTTCACATGG

GACCAAAAACTCTGGTGCCGTCACTTCTGTGTGCTTGCGGACTCA

GAATCTGGTGGACATATCACTCACTCTGGGATGGTGGGCATGGGA

GTCAGCTGCACAGTCACCCGGGAAGATGGAACCAATGACTACAAA

GACGATGACGACAAGTGA

>Exemplary mutant measles envelope
protein, amino acid sequence
(SEQ ID NO: 21):
MGSRIVINREHLMIDRPYVLLAVLFVMFLSLIGLLAIAGIRLHRA

AIYTAEIHKSLSTNLDVTNSIEHQVKDVLTPLFKIIGDEVGLRTP

QRFTDLVKFISDKIKFLNPDREYDFRDLTWCINPPERIKLDYDQY

CADVAAEELMNALVNSTLLETRTTNQFLAVSKGNCSGPTTIRGQF

SNMSLSLLDLYLGRGYNVSSIVTMTSQGMYGGTYLVEKPNLSSKR

SELSQLSMYRVFEVGVIRNPGLGAPVFHMTNYLEQPVSNDLSNCM

VALGELKLAALCHGEDSITIPYQGSGKGVSFQLVKLGVWKSPTDM

QSWVPLSTDDPVIDRLYLSSHRGVIADNQAKWAVPTTRTDDKLRM

ETCFQQACKGKIQALCENPEWAPLKDNRIPSYGVLSVDLSLTVEL

KIKIASGFGPLITHGSGMDLYKSNHNNVYWLTIPPMKNLALGVIN

TLEWIPRFKVSPALFNVPIKEAGGDCHAPTYLPAEVDGDVKLSSN

LVILPGQDLQYVLATYDTSAVEHAVVYYVYSPSRSFSYFYPFRLP

IKGVPIELQVECFTWDQKLWCRHFCVLADSESGGHITHSGMVGMG

VSCTVTREDGTNDYKDDDDK

>Exemplary mutant Nipah envelope
protein, DNA sequence
(SEQ ID NO: 22):
ATGAAGAAGATCAACGAGGGCCTGCTGGACAGCAAGATCCTGAGC

GCCTTCAACACCGTGATTGCCCTGCTGGGCTCTATCGTGATCATC

GTGATGAACATCATGATCATCCAGAACTACACCCGGTCCACCGAC

AACCAGGCCGTGATTAAGGATGCTCTGCAGGGAATCCAGCAGCAG

ATCAAAGGCCTGGCCGACAAGATCGGCACAGAGATCGGCCCTAAG

GTGTCCCTGATCGACACCAGCAGCACCATCACAATCCCCGCCAAT

ATCGGACTGCTGGGAAGCAAGATCAGCCAGAGCACCGCCAGCATC

AACGAGAACGTGAACGAGAAGTGCAAGTTCACCCTGCCTCCACTG

AAGATCCACGAGTGCAACATCAGCTGCCCCAATCCTCTGCCATTC

AGAGAGTACAGACCCCAGACAGAGGGCGTGTCCAATCTCGTGGGC

CTGCCTAACAACATCTGCCTGCAGAAAACCAGCAACCAGATCCTG

AAGCCTAAGCTGATCTCCTACACACTGCCCGTCGTGGGCCAGAGC

GGCACCTGTATTACAGATCCTCTGCTGGCCATGGACGAGGGCTAC

TTTGCCTACAGCCACCTGGAAAGAATCGGCAGCTGTAGCCGGGGA

GTGTCCAAGCAGAGAATCATCGGCGTGGGCGAAGTGCTGGATAGA

GGCGACGAAGTGCCCAGCCTGTTCATGACCAATGTGTGGACCCCT

CCTAATCCTAACACCGTGTACCACTGCAGCGCCGTGTACAACAAC

GAGTTCTACTACGTGCTGTGCGCCGTGTCCACAGTGGGCGACCCT

ATCCTGAACAGCACCTATTGGAGCGGCAGCCTGATGATGACCAGA

CTGGCCGTGAAGCCCAAGAGCAATGGCGGCGGATACAACCAGCAT

CAGCTGGCCCTGCGGTCCATCGAGAAGGGCAGATACGACAAAGTG

ATGCCTTACGCCCCAGCGGCATCAAGCAAGGCGATACCCTGTAC

TTTCCCGCCGTGGGATTTCTCGTGCGGACCGAGTTCAAGTACAAC

GACAGCAACTGCCCCATCACCAAGTGCCAGTACAGCAAGCCCGAG

AACTGCAGACTGAGCATGGGCATCAGACCCAACAGCCACTACATC

CTGAGAAGCGGCCTGCTGAAGTACAACCTGAGCGACGGCGAGAAC

CCCAAGGTGGTGTTCATCGAGATCAGCGACCAGCGGCTGTCTATC

GGCAGCCCCTCCAAGATCTACGACTCTCTGGGCCAGCCAGTGTTC

TACCAGGCCAGCTTTAGCTGGGACACCATGATCAAGTTCGGCGAC

GTGCTGACCGTGAATCCCCTGGTGGTCAACTGGCGGAACAATACC

-continued
GTGATCAGCCGGCCTGGCCAGTCTCAGTGCCCCAGATTCAATACC
TGTCCTGCCATTTGCGCCGAAGGCGTGTACAATGACGCCTTCCTG
ATCGATCGGATCAACTGGATCTCTGCCGGCGTGTTCCTGGACTCT
AATGCCACAGCCGCCAATCCTGTGTTCACCGTGTTCAAGGACAAT
GAGATCCTGTATCGGGCCCAGCTGGCCTCCGAGGACACAAATGCC
CAGAAAACAATCACCAACTGCTTTCTGCTCAAGAACAAGATCTGG
TGCATCAGCCTGGTGGAAATCTACGACACCGGCGACAACGTGATC
AGGCCCAAGCTGTTCGCCGTGAAGATCCCTGAGCAGTGTACAGGC
GGCGGAGGATCTGGCGGAGGTGGAAGCGGAGGCGGTGGATCTGCT
AGCGATTACAAGGATGACGACGATAAGTGA >Exemplary mutant Nipah envelope protein,
amino acid sequence
(SEQ ID NO: 23):
MKKINEGLLDSKILSAFNTVIALLGSIVIIVMNIMIIQNYTRSTD

NQA VIKDALQGIQQQIKGLADKIGTEIGPKVSLIDTSSTITIPA

NIGLLGSKISQSTASINENVNEKCKFTLPPLKIHECNISCPNPLP

FREYRPQTEGVSNLVGLPNNICLQKTSNQILKPKLISYTLPVVGQ

SGTCITDPLLAMDEGYFAYSHLERIGSCSRGVSKQRIIGVGEVLD

RGDEVPSLFMTNVWTPPNPNTVYHCSAVYNNEFYYVLCAVSTVGD

PILNSTYWSGSLMMTRLAVKPKSNGGGYNQHQLALRSIEKGRYDK

VMPYGPSGIKQGDTLYFPAVGFLVRTEFKYNDSNCPITKCQYSKP

ENCRLSMGIRPNSHYILRSGLLKYNLSDGENPKVVFIEISDQRLS

IGSPSKIYDSLGQPVFYQASFSWDTMIKFGDVLTVNPLVVNWRNN

TVISRPGQSQCPRFNTCPAICAEGVYNDAFLIDRINWISAGVFLD

SNATAANPVFTVFKDNEILYRAQLASEDTNAQKTITNCFLLKNKI

WCISLVEIYDTGDNVIRPKLFAVKIPEQCTGGGGSGGGGSGGGGS

ASDYKDDDDK

>IG4 TCR (Variant that binds to NYESO-1
antigen with 32 uM binding affinity),
amino acid sequence
(SEQ ID NO: 24):
MSIGLLCCAALSLLWAGPVNAGVTQTPKFQVLKTGQSMTLQCAQD

MNHEYMSWYRQDPGMGLRLIHYSVGAGITDQGEVPNGYNVSRSTT

EDFPLRLLSAAPSQTSVYFCASSYVGNTGELFFGEGSRLTVLEDL

KNVFPPEVAVFEPSEAEISHTQKATLVCLATGFYPDHVELSWWVN

GKEVHSGVSTDPQPLKEQPALNDSRYCLSSRLRVSATFWQNPRNH

FRCQVQFYGLSENDEWTQDRAKPVTQIVSAEAWGRADCGFTSESY

QQGVLSATILYEILLGKATLYAVLVSALVLMAMVKRKDSRGGSAT

NFSLLKQAGDVEENPGPMETLLGLLILWLQLQWVSSKQEVTQIPA

ALSVPEGENLVLNCSFTDSAIYNLQWFRQDPGKGLTSLLLIQSSQ

REQTSGRLNASLDKSSGSSTLYIAASQPGDSATYLCAVRPTSGGS

YIPTFGRGTSLIVHPYIQNPDPAVYQLRDSKSSDKSVCLFTDFDS

QTNVSQSKDSDVYITDKTVLDMRSMDFKSNSAVAWSNKSDFACAN

AFNNSIIPEDTFFPSPESSCDVKLVEKSFETDTNLNFQNLSVIGF

RILLLKVAGFNLLMTLRLWSSAAA

>IG4 TCR (Variant that binds to NYESO-1
antigen with 84 nM binding affinity),
amino acid sequence
(SEQ ID NO: 25):
MSIGLLCCAALSLLWAGPVNAGVTQTPKFQVLKTGQSMTLQCAQD

MNHEYMSWYRQDPGMGLRLIHYSVGAQTTDQGEVPNGYNVSRSTI

EDFPLRLLSAAPSQTSVYFCASSYLGNTGELFFGEGSRLTVLEDL

KNVFPPEVAVFEPSEAEISHTQKATLVCLATGFYPDHVELSWWVN

GKEVHSGVSTDPQPLKEQPALNDSRYCLSSRLRVSATFWQNPRNH

FRCQVQFYGLSENDEWTQDRAKPVTQIVSAEAWGRADCGFTSESY

QQGVLSATILYEILLGKATLYAVLVSALVLMAMVKRKDSRGGSAT

NFSLLKQAGDVEENPGPMETLLGLLILWLQLQWVSSKQEVTQIPA

ALSVPEGENLVLNCSFTDSAIYNLQWFRQDPGKGLTSLLLIQSSQ

REQTSGRLNASLDKSSGSSTLYIAASQPGDSATYLCAVRPMIGGT

YIPTFGRGTSLIVHPYIQNPDPAVYQLRDSKSSDKSVCLFTDFDS

QTNVSQSKDSDVYITDKTVLDMRSMDFKSNSAVAWSNKSDFACAN

AFNNSIIPEDTFFPSPESSCDVKLVEKSFETDTNLNFQNLSVIGF

RILLLKVAGFNLLMTLRLWSSAAA

>IG4 TCR (Variant that binds to NYESO-1
antigen with 5 nM binding affinity),
amino acid sequence
(SEQ ID NO: 26):
MSIGLLCCAALSLLWAGPVNAGVTQTPKFQVLKTGQSMTLQCAQD

MNHEYMSWYRQDPGMGLRLIHYSVGAGTTDRGEVPNGYNVSRSTI

EDFPLRLLSAAPSQTSVYFCASSYVGDTGELFFGEGSRLTVLEDL

KNVFPPEVAVFEPSEAEISHTQKATLVCLATGFYPDHVELSWWVN

GKEVHSGVSTDPQPLKEQPALNDSRYCLSSRLRVSATFWQNPRNH

FRCQVQFYGLSENDEWTQDRAKPVTQIVSAEAWGRADCGFTSESY

QQGVLSATILYEILLGKATLYAVLVSALVLMAMVKRKDSRGGSAT

NFSLLKQAGDVEENPGPMETLLGLLILWLQLQWVSSKQEVTQIPA

ALSVPEGENLVLNCSFTDSAIYNLQWFRQDPGKGLTSLLLIQSSQ

REQTSGRLNASLDKSSGSSTLYIAASQPGDSATYLCAVRPLLDGT

YIPTFGRGTSLIVHPYIQNPDPAVYQLRDSKSSDKSVCLFTDFDS

QTNVSQSKDSDVYITDKTVLDMRSMDFKSNSAVAWSNKSDFACAN

AFNNSIIPEDTFFPSPESSCDVKLVEKSFETDTNLNFQNLSVIGF

RILLLKVAGFNLLMTLRLWSSAAA

>IG4 TCR (Variant that binds to NYESO-1
antigen with 26 pM binding affinity),
amino acid sequence
(SEQ ID NO: 27):
MSIGLLCCAALSLLWAGPVNAGVTQTPKFQVLKTGQSMTLQCAQD

MNHEYMSWYRQDPGMGLRLIHYSVAIQTTDQGEVPNGYNVSRSTI

EDFPLRLLSAAPSQTSVYFCASSYLGNTGELFFGEGSRLTVLEDL

KNVFPPEVAVFEPSEAEISHTQKATLVCLATGFYPDHVELSWWVN

-continued
GKEVHSGVSTDPQPLKEQPALNDSRYCLSSRLRVSATFWQNPRNH

FRCQVQFYGLSENDEWTQDRAKPVTQIVSAEAWGRADCGFTSESY

QQGVLSATILYEILLGKATLYAVLVSALVLMAMVKRKDSRGGSAT

NFSLLKQAGDVEENPGPMETLLGLLILWLQLQWVSSKQEVTQIPA

ALSVPEGENLVLNCSFTDSAIYNLQWFRQDPGKGLTSLLLITPWQ

REQTSGRLNASLDKSSGSSTLYIAASQPGDSATYLCAVRPLLDGT

YIPTFGRGTSLIVHPYIQNPDPAVYQLRDSKSSDKSVCLFTDFDS

QTNVSQSKDSDVYITDKTVLDMRSMDFKSNSAVAWSNKSDFACAN

AFNNSIIPEDTFFPSPESSCDVKLVEKSFETDTNLNFQNLSVIGF

RILLLKVAGFNLLMTLRLWSSAAA

>868 TCR (Beta Chain-P2A-Alpha Chain),
amino acid sequence
(SEQ ID NO: 31):
MSIGLLCCAALSLLWAGPVNADAGVTQSPTHLIKTRGQQVTLRCS

PKQGHDTVSWYQQALGQGPQFIFQYYEEEERQRGNFPDRFSGHQF

PNYSSELNVNALLLGDSALYLCASSDTVSYEQYFGPGTRLTVTED

LKNVFPPEVAVFEPSEAEISHTQKATLVCLATGFYPDHVELSWWV

NGKEVHSGVSTDPQPLKEQPALNDSRYCLSSRLRVSATFWQDPRN

HFRCQVQFYGLSENDEWTQDRAKPVTQIVSAEAWGRADCGFTSES

YQQGVLSATILYEILLGKATLYAVLVSALVLMAMVKRKDSRGGSA

TNFSLLKQAGDVEENPGPMETLLGLLILWLQLQWVSSKEVEQNSG

PLSVPEGAIASLNCTYSDRGSQSFFWYRQYSGKSPELIMFIYSNG

DKEDGRFTAQLNKASQYISLLIRDSKLSDSATYLCAVRTNSGYAL

NFGKGTSLLVTPHIQKPDPAVYQLRDSKSSDKSVCLFTDFDSQTN

VSQSKDSDVYITDKTVLDMRSMDFKSNSAVAWSNKSDFACANAFN

NSIIPEDTFFPSPESSCDVKLVEKSFETDTNLNFQNLSVIGFRIL

LLKVAGFNLLMTLRLWSS

>CMV C7 TCR, amino acid sequence
(SEQ ID NO: 33):
MGTRLLFWVAFCLLGADHTGAGVSQSPSNKVTEKGKDVELRCDPI

SGHTALYWYRQRLGQGLEFLIYFQGNSAPDKSGLPSDRFSAERTG

ESVSTLTIQRTQQEDSAVYLCASSQTQLWETQYFGPGTRLLVLED

LKNVFPPEVAVFEPSEAEISHTQKATLVCLATGFYPDHVELSWWV

NGKEVHSGVSTDPQPLKEQPALNDSRYCLSSRLRVSATFWQNPRN

HFRCQVQFYGLSENDEWTQDRAKPVTQIVSAEAWGRADCGFTSES

YQQGVLSATILYEILLGKATLYAVLVSALVLMAMVKRKDSRGGSA

TNFSLLKQAGDVEENPGPMEKNPLAAPLLILWFHLDCVSSILNVE

QSPQSLHVQEGDSTNFTCSFPSSNFYALHWYRWETAKSPEALFVM

TLNGDEKKKGRISATLNTKEGYSYLYIKGSQPEDSATYLCAFITG

NQFYFGTGTSLTVIPNIQNPDPAVYQLRDSKSSDKSVCLFTDFDS

QTNVSQSKDSDVYITDKTVLDMRSMDFKSNSAVAWSNKSDFACAN

AFNNSIIPEDTFFPSPESSCDVKLVEKSFETDTNLNFQNLSVIGF

RILLLKVAGFNLLMTLRLWSSAAA

>SL9 pMHC (SL9 peptide portion bolded),
amino acid sequence
(SEQ ID NO: 35):
MSRSVALAVLALLSLSGLEASLYNTVATLGGGASGGGGSGGGGSI

QRTPKIQVYSRHPAENGKSNFLNCYVSGFHPSDIEVDLLKNGERI

EKVEHSDLSFSKDWSFYLLYYTEFTPTEKDEYACRVNHVTLSQPK

IVKWDRDMGGGSGGGGSGGGGSGGGGSHSMRYFFTSVSRPGRGE

PRFIAVGYVDDTQFVRFDSDAASQRMEPRAPWIEQEGPEYWDGET

RKVKAHSQTHRVDLGTLRGAYNQSEAGSHTVQRMYGCDVGSDWRF

LRGYHQYAYDGKDYIALKEDLRSWTAADMAAQTTKHKWEAAHVAE

QLRAYLEGTCVEWLRRYLENGKETLQRTDAPKTHMTHHAVSDHEA

TLRCWALSFYPAEITLTWQRDGEDQTQDTELVETRPAGDGTFQKW

AAVVVPSGQEQRYTCHVQHEGLPKPLTLRWEPSSQPTIPIVGIIA

GLVLFGAVITGAVVAAVMWRRKSS

>CMV pMHC (CMV NLV peptide portion bolded),
amino acid sequence
(SEQ ID NO: 37):
MSRSVALAVLALLSLSGLEANLVPMVATVGASGGSGGGSGGGGSI

QRTPKIQVYSRHPAENGKSNFLNCYVSGFHPSDIEVDLLKNGERI

EKVEHSDLSFSKDWSFYLLYYTEFTPTEKDEYACRVNHVTLSQPK

IVKWDRDMGGGSGGGGSGGGGSGGGGSHSMRYFFTSVSRPGRGE

PRFIAVGYVDDTQFVRFDSDAASQRMEPRAPWIEQEGPEYWDGET

RKVKAHSQTHRVDLGTLRGAYNQSEAGSHTVQRMYGCDVGSDWRF

LRGYHQYAYDGKDYIALKEDLRSWTAADMAAQTTKHKWEAAHVAE

QLRAYLEGTCVEWLRRYLENGKETLQRTDAPKTHMTHHAVSDHEA

TLRCWALSFYPAEITLTWQRDGEDQTQDTELVETRPAGDGTFQKW

AAVVVPSGQEQRYTCHVQHEGLPKPLTLRWEPSSQPTIPIVGIIA

GLVLFGAVITGAVVAAVMWRRKSS

>disulfide trap MHC comprising Y84C
mutation(bolded) and position 2 of
the linker being a C (bolded);
shown with the HGH Signal Peptide
(underlined) and the GL9 peptide
(italicized), amino acid sequence
(SEQ ID NO: 39):
<u>MATGSRTSLLLAFGLLCLPWLQEGSA</u>*GILGFVFTLG*CSGGSGGGS

GGGGSIQRTPKIQVYSRHPAENGKSNFLNCYVSGFHPSDIEVDLL

KNGERIEKVEHSDLSFSKDWSFYLLYYTEFTPTEKDEYACRVNHV

TLSQPKIVKWDRDMGGGSGGSGGGSGSGGGSGGSHSMRYFFTS

VSRPGRGEPRFIAVGYVDDTQFVRFDSDAASQRMEPRAPWIEQEG

PEYWDGETRKVKAHSQTHRVDLGTLRGC**NQSEAGSHTVQRMYGC

DVGSDWRFLRGYHQYAYDGKDYIALKEDLRSWTAADMAAQTTKHK

WEAAHVAEQLRAYLEGTCVEWLRRYLENGKETLQRTDAPKTHMTH

HAVSDHEATLRCWALSFYPAEITLTWQRDGEDQTQDTELVETRPA

GDGTFQKWAAVVVPSGQEQRYTCHVQHEGLPKPLTLRWEPSSQPT

IPIVGIIAGLVLFGAVITGAVVAAVMWRRKSS

>GL9 pMHC (GL9 peptide portion bolded),
amino acid sequence
(SEQ ID NO: 41):
MSRSVALAVLALLSLSGLEAGILGFVFTLGGGASGGGGSGGGGSI

QRTPKIQVYSRHPAENGKSNFLNCYVSGFHPSDIEVDLLKNGERI

EKVEHSDLSFSKDWSFYLLYYTEFTPTEKDEYACRVNHVTLSQPK

IVKWDRDMGGGGSGGGGSGGGGSGGGGSHSMRYFFTSVSRPGRGE

PRFIAVGYVDDTQFVRFDSDAASQRMEPRAPWIEQEGPEYWDGET

RKVKAHSQTHRVDLGTLRGAYNQSEAGSHTVQRMYGCDVGSDWRF

LRGYHQYAYDGKDYIALKEDLRSWTAADMAAQTTKHKWEAAHVAE

QLRAYLEGTCVEWLRRYLENGKETLQRTDAPKTHMTHHAVSDHEA

TLRCWALSFYPAEITLTWQRDGEDQTQDTELVETRPAGDGTFQKW

AAVVVPSGQEQRYTCHVQHEGLPKPLTLRWEPSSQPTIPIVGIIA

GLVLFGAVITGAVVAAVMWRRKSS

>CD80, amino acid sequence
(SEQ ID NO: 43):
MGHTRRQGTSPSKCPYLNFFQLLVLAGLSHFCSGVIHVTKEVKEV

ATLSCGHNVSVEELAQTRIYWQKEKKMVLTMMSGDMNIWPEYKNR

TIFDITNNLSIVILALRPSDEGTYECVVLKYEKDAFKREHLAEVT

LSVKADFPTPSISDFEIPTSNIRRIICSTSGGFPEPHLSWLENGE

ELNAINTTVSQDPETELYAVSSKLDFNMTTNHSFMCLIKYGHLRV

NQTFNWNTTKQEHFPDNLLPSWAITLISVNGIFVICCLTYCFAPR

CRE

>CD86, amino acid sequence
(SEQ ID NO: 45):
MDPQCTMGLSNILFVMAFLLSGAAPLKIQAYFNETADLPCQFANS

QNQSLSELVVFWQDQENLVLNEVYLGKEKFDSVHSKYMGRTSFDS

DSWTLRLHNLQIKDKGLYQCIIHHKKPTGMIRIHQMNSELSVLAN

FSQPEIVPISNITENVYINLTCSSIHGYPEPKKMSVLLRTKNSTI

EYDGVMQKSQDNVTELYDVSISLSVSFPDVTSNMTIFCILETDKT

RLLSSPFSIELEDPQPPPDHIPWITAVLPTVIICVMVFCLILWKW

KKKKR

>mouse anti-TCR Beta Clone H57-597 Fab
antibody (light chain-P2A-heavy chain,
PDGFR transmembrane domain),
amino acid sequence:
(SEQ ID NO: 47):
METDTLLLWVLLLWVPGSTGADYKDDDDKDIQMTQSPSSLPASLG

DRVTINCQASQDISNYLNWYQQKPGKAPKLLIYYTNKLADGVPSR

FSGSGSGRDSSFTISSLESEDIGSYYCQQYYNYPWTFGPGTKLEI

KRADAKPTVSIFPPSSEQLGTGSATLVCFVNNFYPKDINVKWKVD

GSEKRDGVLQSVTDQDSKDSTYSLSSTLSLTKADYERHNLYTCEV

THKTSTAAIVKTLNRNECGSGATNFSLLKQAGDVEENPGPMVPCT

LLLLLAAALAPTQTRAEVQLVESGGGLVQPGKSLKLSCEASGFTF

SGYGMHWVRQAPGRGLESVAYITSSSINIKYADAVKGRFTVSRDN

AKNLLFLQMNILKSEDTAMYYCARFDWDKNYWGQGTMVTVSSAKT

TAPSVYPLAPACDSTTSTTNTVTLGCLVKGYFPEPVTVIWNSGAL

TSGVHTFPSVLHSGLYSLSSSVTVPSSTWPSQTVTCNVAHPASST

TVDLKIEAVGQDTQEVIVVPHSLPFKVVVISAILALVVLTIISLI

ILIMLWQKKPR

>mouse anti-CD3 Epsilon Clone 145-2C11
Fab antibody (light chain-P2A-heavy
chain, PDGFR transmembrane domain),
amino acid sequence
(SEQ ID NO: 49):
METDTLLLWVLLLWVPGSTGADYKDDDDKYELIQPSSASVTVGET

VKITCSGDQLPKNFAYWFQQKSDKNILLLIYMDNKRPSGIPERFS

GSTSGTTATLTISGAQPEDEAAYYCLSSYGDNNDLVFGSGTQLTV

LRGPKSSPKVTVFPPSPEELRTNKATLVCLVNDFYPGSATVTWKA

NGATINDGVKTTKPSKQGQNYMTSSYLSLTADQWKSHNRVSCQVT

HEGETVEKSLSPAECLGSGATNFSLLKQAGDVEENPGPMVPCTLL

LLLAAALAPTQTRAEVYLVESGGDLVQPGSSLKVSCAASGFTFSD

FWMYWVRQAPGKGLEWVGRIKNIPNNYATEYADSVRGRFTISRDD

SRNSIYLQMNRLRVDDTAIYYCTRAGRFDHFDYWGQGTMVTVSSA

TTTAPSVYPLAPACDSTTSTTDTVTLGCLVKGYFPEPVTVSWNSG

ALTSGVHTFPSVLHSGLYSLSSSVTVPSSTWPKQPITCNVAHPAS

STKVDKKIEPRAVGQDTQEVIVVPHSLPFKVVVISAILALVVLTI

ISLIILIMLWQKKPR*

>Cocal Virus Glycoprotein,
amino acid sequence:
(SEQ ID NO: 51):
MNFLLLTFIVLPLCSHAKFSIVFPQSQKGNWKNVPSSYHYCPSSS

DQNWHNDLLGITMKVKMPKTHKAIQADGWMCHAAKWITTCDFRWY

GPKYITHSIHSIQPTSEQCKESIKQTKQGTWMSPGFPPQNCGYAT

VTDSVAVVVQATPHHVLVDEYTGEWIDSQFPNGKCETEECETVHN

STVWYSDYKVTGLCDATLVDTEITFFSEDGKKESIGKPNTGYRSN

YFAYEKGDKVCKMNYCKHAGVRLPSGVWFEFVDQDVYAAAKLPEC

PVGATISAPTQTSVDVSLILDVERILDYSLCQETWSKIRSKQPVS

PVDLSYLAPKNPGTGPAFTIINGTLKYFETRYIRIDIDNPIISKM

VGKISGSQTERELWTEWFPYEGVEIGPNGILKTPTGYKFPLFMIG

HGMLDSDLHKTSQAEVFEHPHLAEAPKQLPEEETLFFGDTGISKN

PVELIEGWFSSWKSTVVTFFFAIGVFILLYVVARIVIAVRYRYQG

SNNKRIYNDIEMSRFRK*

>Cocal Virus Glycoprotein, DNA sequence:
(SEQ ID NO: 52):
ATGAACTTTCTGCTGCTCACGTTTATCGTACTCCCGTTGTGCTCT

CATGCGAAATTTTCAATAGTCTTTCCTCAGTCCCAGAAAGGGAAT

TGGAAAAATGTTCCCTCCAGTTACCACTATTGTCCCTCCTCCTCT

GACCAAAACTGGCACAATGACTTGCTCGGGATTACAATGAAGTA

AAGATGCCGAAAACCCATAAAGCCATACAGGCGGATGGGTGGATG

TGTCACGCTGCGAAGTGGATCACTACATGCGATTTCCGGTGGTAT

GGCCCTAAGTACATTACACACTCTATCCATAGCATACAGCCGACA

-continued

TCAGAGCAATGCAAAGAGAGTATTAAACAGACCAAACAAGGGACA

TGGATGAGCCCTGGCTTTCCACCTCAGAATTGTGGGTACGCGACC

GTCACGGATAGTGTCGCTGTTGTGGTGCAGGCCACGCCACATCAC

GTACTCGTAGATGAATATACTGGTGAATGGATCGACTCCCAATTC

CCGAATGGGAAATGTGAGACGGAAGAGTGCGAAACAGTGCATAAC

TCAACCGTTTGGTATTCCGATTACAAGGTTACTGGTCTTTGCGAC

GCCACCCTCGTGGATACCGAGATCACGTTTTTTAGTGAGGATGGC

AAGAAAGAGTCAATAGGCAAACCTAATACTGGCTACCGGAGTAAC

TATTTCGCTTACGAGAAGGGTGACAAGGTATGTAAAATGAACTAT

TGCAAGCATGCGGGAGTGCGACTCCCCAGTGGGGTATGGTTCGAA

TTTGTTGACCAAGACGTATACGCCGCTGCGAAGTTGCCAGAATGC

CCCGTAGGCGCGACCATTTCAGCACCTACCCAAACGTCCGTTGAC

GTCTCCTTGATACTGGATGTAGAGCGAATCCTGGACTACAGTCTC

TGCCAGGAAACGTGGTCAAAAATAAGAAGTAAGCAGCCAGTTTCA

CCCGTGGATCTGTCTTATCTGGCGCCAAAAAACCCGGGCACGGGC

CCTGCTTTTACCATAATTAACGGAACGCTTAAATACTTCGAAACC

CGCTACATTAGAATCGATATAGACAATCCTATTATCAGCAAGATG

GTAGGGAAGATATCTGGGTCTCAAACGGAGCGAGAATTGTGGACG

GAGTGGTTCCCTTATGAGGGAGTGGAAATTGGGCCCAACGGGATC

CTCAAGACCCCAACGGGTTACAAGTTCCCTCTGTTTATGATCGGC

CATGGCATGTTGGACAGTGACTTGCACAAAACATCTCAGGCAGAG

GTTTTCGAACATCCACATTTGGCGGAGGCGCCCAAGCAACTTCCA

GAAGAAGAAACTCTCTTCTTTGGAGATACAGGCATTTCAAAAAAT

CCTGTAGAACTGATAGAAGGGTGGTTCTCTTCCTGGAAATCAACG

GTTGTCACGTTTTTCTTTGCAATAGGCGTATTTATACTCCTGTAC

GTCGTAGCCCGCATTGTGATCGCAGTACGATACAGATACCAGGGC

AGTAACAATAAACGCATATATAATGACATCGAAATGTCAAGGTTC

CGAAAGtga

>Cocal-dead (mutations to ablate native tropism bolded in protein sequence; these are K64Q and R371A, counting from the start codon), amino acid sequence:
(SEQ ID NO: 53):

MNFLLLTFIVLPLCSHAKFSIVFPQSQKGNWKNVPSSYHYCPSSS

DQNWHNDLLGITMKVKMPQTHKAIQADGWMCHAAKWITTCDFRWY

GPKYITHSIHSIQPTSEQCKESIKQTKQGTWMSPGFPPQNCGYAT

VTDSVAVVVQATPHHVLVDEYTGEWIDSQFPNGKCETEECETVHN

STVWYSDYKVTGLCDATLVDTEITFFSEDGKKESIGKPNTGYRSN

YFAYEKGDKVCKMNYCKHAGVRLPSGVWFEFVDQDVYAAAKLPEC

PVGATISAPTQTSVDVSLILDVERILDYSLCQETWSKIRSKQPVS

PVDLSYLAPKNPGTGPAFTIINGTLKYFETRYIRIDIDNPIISKM

VGKISGSQTEAELWTEWFPYEGVEIGPNGILKTPTGYKFPLFMIG

-continued

HGMLDSDLHKTSQAEVFEHPHLAEAPKQLPEEETLFFGDTGISKN

PVELIEGWFSSWKSTVVTFFFAIGVFILLYVVARIVIAVRYRYQG

SNNKRIYNDIEMSRFRK

>Cocal-dead (mutations to ablate native tropism), DNA sequence:
(SEQ ID NO: 54):

ATGAACTTTCTGCTGCTCACGTTTATCGTACTCCCGTTGTGCTCT

CATGCGAAATTTTCAATAGTCTTTCCTCAGTCCCAGAAAGGGAAT

TGGAAAAATGTTCCCTCCAGTTACCACTATTGTCCCTCCTCCTCT

GACCAAAACTGGCACAATGACTTGCTCGGGATTACAATGAAAGTA

AAGATGCCGcagACCCATAAAGCCATACAGGCGGATGGGTGGATG

TGTCACGCTGCGAAGTGGATCACTACATGCGATTTCCGGTGGTAT

GGCCCTAAGTACATTACACACTCTATCCATAGCATACAGCCGACA

TCAGAGCAATGCAAAGAGAGTATTAAACAGACCAAACAAGGGACA

TGGATGAGCCCTGGCTTTCCACCTCAGAATTGTGGGTACGCGACC

GTCACGGATAGTGTCGCTGTTGTGGTGCAGGCCACGCCACATCAC

GTACTCGTAGATGAATATACTGGTGAATGGATCGACTCCCAATTC

CCGAATGGGAAATGTGAGACGGAAGAGTGCGAAACAGTGCATAAC

TCAACCGTTTGGTATTCCGATTACAAGGTTACTGGTCTTTGCGAC

GCCACCCTCGTGGATACCGAGATCACGTTTTTTAGTGAGGATGGC

AAGAAAGAGTCAATAGGCAAACCTAATACTGGCTACCGGAGTAAC

TATTTCGCTTACGAGAAGGGTGACAAGGTATGTAAAATGAACTAT

TGCAAGCATGCGGGAGTGCGACTCCCCAGTGGGGTATGGTTCGAA

TTTGTTGACCAAGACGTATACGCCGCTGCGAAGTTGCCAGAATGC

CCCGTAGGCGCGACCATTTCAGCACCTACCCAAACGTCCGTTGAC

GTCTCCTTGATACTGGATGTAGAGCGAATCCTGGACTACAGTCTC

TGCCAGGAAACGTGGTCAAAAATAAGAAGTAAGCAGCCAGTTTCA

CCCGTGGATCTGTCTTATCTGGCGCCAAAAAACCCGGGCACGGGC

CCTGCTTTTACCATAATTAACGGAACGCTTAAATACTTCGAAACC

CGCTACATTAGAATCGATATAGACAATCCTATTATCAGCAAGATG

GTAGGGAAGATATCTGGGTCTCAAACGGAGgccGAATTGTGGACG

GAGTGGTTCCCTTATGAGGGAGTGGAAATTGGGCCCAACGGGATC

CTCAAGACCCCAACGGGTTACAAGTTCCCTCTGTTTATGATCGGC

CATGGCATGTTGGACAGTGACTTGCACAAAACATCTCAGGCAGAG

GTTTTCGAACATCCACATTTGGCGGAGGCGCCCAAGCAACTTCCA

GAAGAAGAAACTCTCTTCTTTGGAGATACAGGCATTTCAAAAAAT

CCTGTAGAACTGATAGAAGGGTGGTTCTCTTCCTGGAAATCAACG

GTTGTCACGTTTTTCTTTGCAATAGGCGTATTTATACTCCTGTAC

GTCGTAGCCCGCATTGTGATCGCAGTACGATACAGATACCAGGGC

AGTAACAATAAACGCATATATAATGACATCGAAATGTCAAGGTTC

CGAAAGtga

What is claimed is:

1. A retrovirus comprising:

(a) a nucleic acid encoding a gene of interest; and (b) a viral envelope that comprises at least two different proteins:

(i) a viral envelope protein comprising at least one mutation that diminishes the native viral tropism compared to the non-mutated viral envelope protein, wherein the viral envelope protein is a vesicular stomatitis virus (VSV-G) envelope protein that comprises an amino acid substitution at position K47 and/or amino acid substitution at position R354, said positions with reference to SEQ ID NO: 13 or a cocal virus G envelope that comprises an amino acid substitution at position K64 and/or position R371, said positions with reference to SEQ ID NO: 51; and (ii) a non-viral membrane-bound protein comprising a transmembrane domain and an extracellular targeting domain that binds to a ligand expressed on the surface of a cell.

2. The retrovirus of claim 1, wherein the retrovirus is a lentivirus.

3. The retrovirus of claim 1, wherein:

(a) the at least one mutation of the VSV-G envelope protein is an amino acid substitution at position K47 to alanine (A) or glutamine (Q) and/or position R354 to alanine (A) or glutamine (Q), said positions with reference to SEQ ID NO: 13; or (b) the at least one mutation of the cocal virus G envelope protein is an amino acid substitution at position K64 to alanine (A) or glutamine (Q) and/or position R371 to alanine (A) or glutamine (Q), said positions with reference to SEQ ID NO: 51.

4. The retrovirus of claim 1, wherein the extracellular targeting domain comprises a protein, a peptide, or an antibody.

5. The retrovirus of claim 1, wherein the extracellular targeting domain binds to a ligand expressed on the surface of a T cell or B cell.

6. The retrovirus of claim 1, wherein the extracellular targeting domain comprises an interleukin-13 protein domain, a CD80 protein domain, a full-length antibody, an antibody fragment, a nanobody, a single chain antibody (scFv), an anti-CD19 antibody, an anti-TCR antibody, or an anti-CD3 antibody.

7. The retrovirus of claim 1, wherein the ligand is a T cell receptor (TCR), a cytokine receptor, a cytokine, a T cell surface marker, CD3, CD19, or CD20.

8. A retrovirus comprising:
(a) a nucleic acid encoding a gene of interest; and
(b) a viral envelope that comprises at least two different proteins:
(i) a CD80 protein that comprises a CD80 extracellular domain and a transmembrane domain; and
(ii) a mutated viral envelope protein comprising at least one mutation that diminishes the native viral tropism of the mutated viral envelope protein compared to the non-mutated viral envelope protein, wherein the viral envelope protein is a VSV-G envelope protein that comprises an amino acid substitution at position K47 and/or an amino acid substitution at position R534, said positions with reference to SEQ ID NO: 13 or a cocal virus G envelope protein that comprises an amino acid substitution at position K64 and/or an amino acid substitution at position R371, said positions with reference to SEQ ID NO: 51.

9. The retrovirus of claim 8, wherein the retrovirus is a lentivirus.

10. The retrovirus of claim 8, wherein:
(a) the at least one mutation of the VSV-G envelope protein is an amino acid substitution at position K47 to alanine (A) or glutamine (Q) and/or position R354 to alanine (A) or glutamine (Q), said positions with reference to SEQ ID NO: 13; or
(b) the at least one mutation of the cocal virus G envelope protein is an amino acid substitution at position K64 to alanine (A) or glutamine (Q) and/or position R371 to alanine (A) or glutamine (Q), said positions with reference to SEQ ID NO: 51.

11. The retrovirus of claim 8, further comprising a non-viral membrane-bound protein comprising an extracellular targeting domain that binds to a ligand expressed on the surface of a cell.

12. The retrovirus of claim 11, wherein the non-viral membrane-bound protein comprises an extracellular targeting domain extracellular targeting domain that comprises an interleukin-13 protein domain, a full-length antibody, an antibody fragment, a nanobody, a single chain antibody (scFv), an anti-CD19 antibody, an anti-TCR antibody, or an anti-CD3 antibody.

13. The retrovirus of claim 11, wherein the ligand is a T cell receptor (TCR), a cytokine receptor, a cytokine, a T cell surface marker, CD3, CD19, or CD20.

14. A retrovirus comprising:
(a) a nucleic acid encoding a gene of interest;
(b) a viral envelope that comprises at least two different proteins:
(i) a non-viral membrane-bound protein comprising a transmembrane domain and an extracellular targeting domain that comprises an anti-CD3 antibody; and
(ii) a mutated viral envelope protein comprising at least one mutation that diminishes the native viral tropism of the mutated viral envelope protein compared to the non-mutated viral envelope protein, wherein the viral envelope protein is a VSV-G envelope protein that comprises an amino acid substitution at position K47 and/or an amino acid substitution at position R354, said positions with reference to SEQ ID NO: 13 or a cocal virus G envelope protein that comprises an amino acid substitution at position K64 and/or an amino acid substitution at position R371, said positions with reference to SEQ ID NO: 51.

15. The retrovirus of claim 14, wherein the retrovirus is a lentivirus.

16. The retrovirus of claim 14, wherein:
(a) the at least one mutation of the VSV-G envelope protein is an amino acid substitution at position K47 to alanine (A) or glutamine (Q) and/or position R354 to alanine (A) or glutamine (Q), said positions with reference to SEQ ID NO: 13; or
(b) the at least one mutation of the cocal virus G envelope protein is an amino acid position at position K64 and/or position R371, said positions with reference to SEQ ID NO: 51.

17. The retrovirus of claim 14, further comprising a non-viral membrane-bound protein comprising an extracellular targeting domain that binds to a ligand of a cell.

18. The retrovirus of claim 17, wherein the non-viral membrane-bound protein comprises an extracellular targeting domain extracellular targeting domain that comprises an interleukin-13 protein domain, a CD80 protein domain, a full-length antibody, an antibody fragment, a nanobody, a single chain antibody (scFv), an anti-CD19 antibody, or an anti-TCR antibody.

19. The retrovirus of claim 17, wherein the ligand is a T cell receptor (TCR), a cytokine receptor, a cytokine, a T cell surface marker, CD19, or CD20.

* * * * *

SEQUENCE LISTING

```
Sequence total quantity: 54
SEQ ID NO: 1              moltype = AA  length = 20
FEATURE                   Location/Qualifiers
REGION                    1..20
                          note = Synthetic Polypeptide
source                    1..20
                          mol_type = protein
                          organism = synthetic construct
SEQUENCE: 1
METDTLLLWV LLLWVPGSTG                                                         20

SEQ ID NO: 2              moltype = AA  length = 20
FEATURE                   Location/Qualifiers
REGION                    1..20
                          note = Synthetic Polypeptide
source                    1..20
                          mol_type = protein
                          organism = synthetic construct
SEQUENCE: 2
MSRSVALAVL ALLSLSGLEA                                                         20

SEQ ID NO: 3              moltype = AA  length = 19
FEATURE                   Location/Qualifiers
REGION                    1..19
                          note = Synthetic Polypeptide
source                    1..19
                          mol_type = protein
                          organism = synthetic construct
SEQUENCE: 3
AVGQDTQEVI VVPHSLPFK                                                          19

SEQ ID NO: 4              moltype = AA  length = 49
FEATURE                   Location/Qualifiers
REGION                    1..49
                          note = Synthetic Polypeptide
source                    1..49
                          mol_type = protein
                          organism = synthetic construct
SEQUENCE: 4
ASAKPTTTPA PRPPTPAPTI ASQPLSLRPE AARPAAGGAV HTRGLDFAK                         49

SEQ ID NO: 5              moltype = AA  length = 6
FEATURE                   Location/Qualifiers
REGION                    1..6
                          note = Synthetic Polypeptide
source                    1..6
                          mol_type = protein
                          organism = synthetic construct
SEQUENCE: 5
GAPGAS                                                                         6

SEQ ID NO: 6              moltype = AA  length = 17
FEATURE                   Location/Qualifiers
REGION                    1..17
                          note = Synthetic Polypeptide
source                    1..17
                          mol_type = protein
                          organism = synthetic construct
SEQUENCE: 6
GAPGSGGGGS GGGGSAS                                                            17

SEQ ID NO: 7              moltype = AA  length = 5
FEATURE                   Location/Qualifiers
REGION                    1..5
                          note = Synthetic Polypeptide
source                    1..5
                          mol_type = protein
                          organism = synthetic construct
SEQUENCE: 7
GGGGS                                                                          5

SEQ ID NO: 8              moltype = AA  length = 33
FEATURE                   Location/Qualifiers
REGION                    1..33
                          note = Synthetic Polypeptide
source                    1..33
                          mol_type = protein
                          organism = synthetic construct
```

-continued

```
SEQUENCE: 8
ASESKYGPPC PPCPAVGQDT QEVIVVPHSL PFK                                      33

SEQ ID NO: 9              moltype = AA  length = 39
FEATURE                   Location/Qualifiers
REGION                    1..39
                          note = Synthetic Polypeptide
source                    1..39
                          mol_type = protein
                          organism = synthetic construct
SEQUENCE: 9
ASGGGGSGEL AAIKQELAAI KKELAAIKWE LAAIKQGAG                                39

SEQ ID NO: 10             moltype = AA  length = 14
FEATURE                   Location/Qualifiers
REGION                    1..14
                          note = Synthetic Polypeptide
source                    1..14
                          mol_type = protein
                          organism = synthetic construct
SEQUENCE: 10
ASESKYGPPC PPCP                                                           14

SEQ ID NO: 11             moltype = DNA  length = 1536
FEATURE                   Location/Qualifiers
misc_feature              1..1536
                          note = Synthetic Polynucleotide
source                    1..1536
                          mol_type = other DNA
                          organism = synthetic construct
SEQUENCE: 11
atgaagtgcc ttttgtactt agcctttta ttcattgggg tgaattgcaa gttcaccata          60
gttttccac acaaccaaaa aggaaactgg aaaaatgttc cttctaatta ccattattgc         120
ccgtcaagct cagatttaaa ttggcataat gacttaatag gcacagccat acaagtcaaa        180
atgcccaaga gtcacaaggc tattcaagca gacggttgga tgtgtcatgc ttccaaatgg        240
gtcactactt tgtgatttcg ctggtatgga ccgaagtata taacacagtc catccgatcc        300
ttcactccat ctgtagaaca atgcaaggaa agcattgaac aaacgaaaca aggaacttgg        360
ctgaatccag gcttccctcc tcaaagttgt ggatatgcaa ctgtgacgga tgccgaagca        420
gtgattgtcc aggtgactcc tcaccatgtg ctggttgatg aatacacagg agaatgggtt        480
gattcacagt tcatcaacgg aaaatgcagc aattacatat gccccactgt ccataactct        540
acaacctggc attctgacta taaggtcaaa gggctatgtg attctaacct catttccatg        600
gacatcacct tcttctcaga ggacgagag ctatcatccc tggaaaagga gggcacaggg         660
ttcagaagta actactttgc ttatgaaact ggaggcaagg cctgcaaaat gcaatactgc        720
aagcattggg gagtcagact cccatcaggt gtcggttcg agatggctga taaggatctc         780
tttgctgcag ccagattccc tgaatgccca gaagggtcaa gtatctctgc tccatctcag        840
acctcagtgg atgtaagtct aattcaggac gttgagagga tcttggatta ttccctctgc        900
caagaaacct ggagcaaaat cagagcgggt cttccaatct ctccagtgga tctcagctat        960
cttgctccta aaaacccagg aaccggtcct gctttcacca taatcaatgg taccctaaaa       1020
tactttgaga ccagatacat cagagtcgat attgctgctc caatcctctc aagaatggtc       1080
ggaatgatca gtggaactac cacagaaagg gaactgtggg atgactgggc accatatgaa       1140
gacgtgagaa ttggacccaa tggagttctg aggaccagtt caggatataa gtttcctta        1200
tacatgattg gacatggtat gttggactcc gatcttcatc ttagctcaaa ggctcaggta       1260
ttcgaacatc ctcacattca agacgctgct tcgcaacttc ctgatgatga gagtttattt       1320
tttggtgata ctgggctatc caaaaatcca atcgagcttg tagaaggttg gttcagtagt       1380
tggaaaagct ctattgcctc tttttctttt atcatagggt taatcattgg actattcttg       1440
gttctccgag ttggtatcca tctttgcatt aaattaaagc acaccaagaa aagacagatt       1500
tatacagaca tagagatgaa ccgacttgga aagtaa                                 1536

SEQ ID NO: 12             moltype = AA  length = 511
FEATURE                   Location/Qualifiers
REGION                    1..511
                          note = Synthetic Polypeptide
source                    1..511
                          mol_type = protein
                          organism = synthetic construct
SEQUENCE: 12
MKCLLYLAFL FIGVNCKFTI VFPHNQKGNW KNVPSNYHYC PSSSDLNWHN DLIGTAIQVK         60
MPKSHKAIQA DGWMCHASKW VTTCDFRWYG PKYITQSIRS FTPSVEQCKE SIEQTKQGTW        120
LNPGFPPQSC GYATVTDAEA VIVQVTPHHV LVDEYTGEWV DSQFINGKCS NYICPTVHNS        180
TTWHSDYKVK GLCDSNLISM DITFFSEDGE LSSLGKEGTG FRSNYFAYET GGKACKMQYC        240
KHWGVRLPSG VWFEMADKDL FAAARFPECP EGSSISAPSQ TSVDVSLIQD VERILDYSLC        300
QETWSKIRAG LPISPVDLSY LAPKNPGTGP AFTIINGTLK YFETRYIRVD IAAPILSRMV        360
GMISGTTTER ELWDDWAPYE DVEIGPNGVL RTSSGYKFPL YMIGHGMLDS DLHLSSKAQV        420
FEHPHIQDAA SQLPDDESLF FGDTGLSKNP IELVEGWFSS WKSSIASFFF IIGLIIGLFL        480
VLRVGIHLCI KLKHTKKRQI YTDIEMNRLG K                                      511

SEQ ID NO: 13             moltype = AA  length = 495
FEATURE                   Location/Qualifiers
REGION                    1..495
```

```
                         note = Synthetic Polypeptide
source                   1..495
                         mol_type = protein
                         organism = synthetic construct
SEQUENCE: 13
KFTIVFPHNQ KGNWKNVPSN YHYCPSSSDL NWHNDLIGTA IQVKMPKSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
LISMDITFFS EDGELSSLGK EGTGFRSNYF AYETGGKACK MQYCKHWGVR LPSGVWFEMA   240
DKDLFAAARF PECPEGSSIS APSQTSVDVS LIQDVERILD YSLCQETWSK IRAGLPISPV   300
DLSYLAPKNP GTGPAFTIIN GTLKYFETRY IRVDIAAPIL SRMVGMISGT TTERELWDDW   360
APYEDVEIGP NGVLRTSSGY KFPLYMIGHG MLDSDLHLSS KAQVFEHPHI QDAASQLPDD   420
ESLFFGDTGL SKNPIELVEG WFSSWKSSIA SFFFIIGLII GLFLVLRVGI HLCIKLKHTK   480
KRQIYTDIEM NRLGK                                                   495

SEQ ID NO: 14            moltype = DNA   length = 1536
FEATURE                  Location/Qualifiers
misc_feature             1..1536
                         note = Synthetic Polynucleotide
source                   1..1536
                         mol_type = other DNA
                         organism = synthetic construct
SEQUENCE: 14
atgaagtgcc ttttgtactt agccttttta ttcattgggg tgaattgcaa gttcaccata    60
gtttttccac acaaccaaaa aggaaactgg aaaaatgttc cttctaatta ccattattgc   120
ccgtcaagct cagatttaaa ttggcataat gacttaatag gcacagcctt acaagtcaaa   180
atgcccagag tcacaaggc tattcaagca gacggttgga tgtgtcatgc ttccaaatgg   240
gtcactactt gtgatttccg ctggtatgga ccgaagtata taacacagtc catccgatcc   300
ttcactccat ctgtagaaca atgcaaggaa agcattgaac aaacgaaaca aggaacttgg   360
ctgaatccag gcttccctcc tcaaagttgt ggatatgcaa ctgtgacgga tgccgaagca   420
gtgattgtcc aggtgactcc tcaccatgtg ctggttgatg aatacacagg agaatgggtt   480
gattcacagt tcatcaacgg aaaatgcagc aattacatat gccccactgt ccataactct   540
acaacctggc attctgacta taaggtcaaa gggctatgtg attctaacct catttccatg   600
gacatcacct tcttctcaga ggacggagag ctatcatccc tgggaaagga gggcacaggg   660
ttcagaagta actactttgc ttatgaaact ggaggcaagg cctgcaaaat gcaatactgc   720
aagcattggg gagtcagact cccatcaggt gtctggttcg agatggctga taaggatctc   780
tttgctgcag ccagattccc tgaatgccca gaagggtcaa gtatctctgc tccatctcag   840
acctcagtgg atgtaagtct aattcaggac gttgagagga tcttggatta ttcccctgc   900
caagaaacct ggagcaaaat cagagcgggt cttccaatct ctccagtgga tctcagctat   960
cttgctccta aaaacccagg aaccggtcct gctttcacca taatcaatgg taccctaaaa  1020
tactttgaga ccagatacat cagagtcgat attgctgctc caatcctctc aagaatggtc  1080
ggaatgatca gtggaactac cacagaagcc gaactgtggg atgactgggc accatatgaa  1140
gacgtggaaa ttggacccaa tggagttctg aggaccagtt caggatataa gtttcctta   1200
tacatgattg gacatggtat gttggactcc gatcttcatc ttagctcaaa ggctcaggtg  1260
ttcgaacatc ctcacattca agacgctgct tcgcaacttc ctgatgatga gagtttattt  1320
tttggtgata ctgggctatc caaaaatcca atcgagcttg tagaaggttg gttcagtagt  1380
tggaaaagct ctattgcctc ttttttcttt atcatagggt taatcattgg actattcttg  1440
gttctccgag ttggtatcca tctttgcatt aaaattaaagc acaccaagaa aagacagatt  1500
tatacagaca tagagatgaa ccgacttgga aagtaa                            1536

SEQ ID NO: 15            moltype = AA   length = 511
FEATURE                  Location/Qualifiers
REGION                   1..511
                         note = Synthetic Polypeptide
source                   1..511
                         mol_type = protein
                         organism = synthetic construct
SEQUENCE: 15
MKCLLYLAFL FIGVNCKFTI VFPHNQKGNW KNVPSNYHYC PSSSDLNWHN DLIGTALQVK    60
MPQSHKAIQA DGWMCHASKW VTTCDFRWYG PKYITQSIRS FTPSVEQCKE SIEQTKQGTW   120
LNPGFPPQSC GYATVTDAEA VIVQVTPHHV LVDEYTGEWV DSQFINGKCS NYICPTVHNS   180
TTWHSDYKVK GLCDSNLISM DITFFSEDGE LSSLGKEGTG FRSNYFAYET GGKACKMQYC   240
KHWGVRLPSG VWFEMADKDL FAAARFPECP EGSSISAPSQ TSVDVSLIQD VERILDYSLC   300
QETWSKIRAG LPISPVDLSY LAPKNPGTGP AFTIINGTLK YFETRYIRVD IAAPILSRMV   360
GMISGTTTEA ELWDDWAPYE DVEIGPNGVL RTSSGYKFPL YMIGHGMLDS DLHLSSKAQV   420
FEHPHIQDAA SQLPDDESLF FGDTGLSKNP IELVEGWFSS WKSSIASFFF IIGLIIGLFL   480
VLRVGIHLCI KLKHTKKRQI YTDIEMNRLG K                                  511

SEQ ID NO: 16            moltype = AA   length = 495
FEATURE                  Location/Qualifiers
REGION                   1..495
                         note = Synthetic Polypeptide
source                   1..495
                         mol_type = protein
                         organism = synthetic construct
SEQUENCE: 16
KFTIVFPHNQ KGNWKNVPSN YHYCPSSSDL NWHNDLIGTA LQVKMPQSHK AIQADGWMCH    60
ASKWVTTCDF RWYGPKYITQ SIRSFTPSVE QCKESIEQTK QGTWLNPGFP PQSCGYATVT   120
DAEAVIVQVT PHHVLVDEYT GEWVDSQFIN GKCSNYICPT VHNSTTWHSD YKVKGLCDSN   180
```

```
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEAELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 17            moltype = AA  length = 495
FEATURE                  Location/Qualifiers
REGION                   1..495
                         note = Synthetic Polypeptide
source                   1..495
                         mol_type = protein
                         organism = synthetic construct
SEQUENCE: 17
KFTIVFPHNQ KGNWKNVPSN YHYCPSSSDL NWHNDLGTIA IQVKMPQSHK AIQADGWMCH     60
ASKWVTTCDF RWYGPKYITQ SIRSFTPSVE QCKESIEQTK QGTWLNPGFP PQSCGYATVT    120
DAEAVIVQVT PHHVLVDEYT GEWVDSQFIN GKCSNYICPT VHNSTTWHSD YKVKGLCDSN    180
LISMDITFFS EDGELSSLGK EGTGFRSNYF AYETGGKACK MQYCKHWGVR LPSGVWFEMA    240
DKDLFAAARF PECPEGSSIS APSQTSVDVS LIQDVERILD YSLCQETWSK IRAGLPISPV    300
DLSYLAPKNP GTGPAFTIIN GTLKYFETRY IRVDIAAPIL SRMVGMISGT TTEAELWDDW    360
APYEDVEIGP NGVLRTSSGY KFPLYMIGHG MLDSDLHLSS KAQVFEHPHI QDAASQLPDD    420
ESLFFGDTGL SKNPIELVEG WFSSWKSSIA SFFFIIGLII GLFLVLRVGI HLCIKLKHTK    480
KRQIYTDIEM NRLGK                                                    495

SEQ ID NO: 18            moltype = DNA  length = 1818
FEATURE                  Location/Qualifiers
source                   1..1818
                         mol_type = other DNA
                         organism = Synthetic construct
SEQUENCE: 18
atgggcagcc ggatcgtgat caaccgggag cacctgatga tcgaccggcc ctacgtgctg     60
ctggccgtgc tgttcgtgat gttcctgagc ctgatcggct tgctagccat tgctggaatc    120
cggctgcaca gagccgccat ctacaccgcc gagatccaca agagcctgag caccaacctg    180
gacgtgacca acagcatcga gcatcaggtc aaggacgtgc tgaccccctc gtttaagatc    240
atcggcgacg aagtgggcct gcggacccccc agagattcca ccgacctggt caagttcatc    300
agcgacaaga tcaagttcct gaaccccgac cgggagtacg acttccggga cctgacctgg    360
tgcatcaacc ccccgagcg gatcaagctg gactacgacc agtactgcgc cgatgtggcc    420
gccgaggaac tgatgaatgc attggtgaac tcaactctac tggagacgag aacaaccaat    480
cagttcctag ctgtctcaaa gggaaactgc tcagggccca ctacaatcag aggtcaattc    540
tcaaacatgt cgctgtccct gttagacttg tatttaggtc gaggttacaa tgtgtcatct    600
atagtcacta tgacatccca gggaatgtat ggggaactt acctagtgga aaagcctaat    660
ctgagcagca aaaggtcaga gttgtcacaa ctgagcatgt accgagtgtt tgaagtaggt    720
gttatcagaa atccgggttt gggggctccg gtgttccata tgacaaacta tcttgagcaa    780
ccagtcagta atgatctcag caactgtatg gtggctttgg gggagctcaa actcgcagcc    840
ctttgtcacg gggaagattc tatcacaatt ccctatcagg gatcagggaa aggtgtcagc    900
ttccagctcg tcaagctagg tgtctggaaa tccccaaccg acatgcaatc ctgggtcccc    960
ttatcaacgg atgatccagt gatagacagg ctttacctct catctcacag aggtgttatc   1020
gctgacaacc aagcaaaatg ggctgtcccg acaacacgaa cagatgacaa gttgcgaatg   1080
gagacatgct ccaacaggc gtgtaaggt aaatccaag cactctgcga gaatcccgag   1140
tgggcaccat tgaaggataa caggattcct tcatacggtg tcttgtctgt tgatctgaca   1200
ctgacagttg agcttaaaat caaaattgct tcgggattcg gccattgat cacacacggt   1260
tcagggatgg acctatacaa atccaaccac aacaatgtgt attggctgac atcccgcca   1320
atgaagaacc tagcccttag tgtaatcaac acattggagt ggataccgag attcaaggtt   1380
agtcccctatc tcttcacagt cccaattaag gaagcaggga gagctgcca tgccccaaca   1440
tacctacctg cggaggtgga tggtgatgtc aaactcagtt ccaatctggt gattctacct   1500
ggtcaagatc tccaatatgt tttggcaacc tacgatactt cccggggtga acatgctgtg   1560
gtttattacg tttacagccc aagccgctca ttttcttact tttatccttt taggttgcct   1620
ataaggggg tccccatcga attcaagtg gaatgcttca catgggacca aaaactctgg   1680
tgccgtcact tctgtgtgct tcggactca gaatcggtg gacatatcac tcactctggg   1740
atggtgggca tgggagtcag ctgcacagtc acccgggaag atggaaccaa tgactacaaa   1800
gacgatgacg acaagtga                                                1818

SEQ ID NO: 19            moltype = AA  length = 605
FEATURE                  Location/Qualifiers
REGION                   1..605
                         note = Synthetic Polypeptide
source                   1..605
                         mol_type = protein
                         organism = synthetic construct
SEQUENCE: 19
MGSRIVINRE HLMIDRPYVL LAVLFVMFLS LIGLLAIAGI RLHRAAIYTA EIHKSLSTNL     60
DVTNSIEHQV KDVLTPLFKI IGDEVGLRTP QRFTDLVKFI SDKIKFLNPD REYDFRDLTW    120
CINPPERIKL DYDQYCADVA AEELMNALVN STLLETRTTN QFLAVSKGNC SGPTTIRGQF    180
SNMSLSLLDL YLGRGYNVSS IVTMTSQGMY GGTYLVEKPN LSSKRSELSQ LSMYRVFEVG    240
VIRNPGLGAP VFHMTNYLEQ PVSNDLSNCM VALGELKLAA LCHGEDSITI PYQGSGKGVS    300
FQLVKLGVWK SPTDMQSWVP LSTDDPVIDR LYLSSHRGVI ADNQAKWAVP TTRTDDKLRM    360
ETCFQQACKG KIQALCENPE WAPLKDNRIP SYGVLSVDLS LTVELKIKIA SGFGPLITHG    420
SGMDLYKSNH NNVYWLTIPP MKNLALGVIN TLEWIPRFKV SPYLFTVPIK EAGGDCHAPT    480
```

```
YLPAEVDGDV KLSSNLVILP GQDLQYVLAT YDTSRVEHAV VYYVYSPSRS FSYFYPFRLP   540
IKGVPIELQV ECFTWDQKLW CRHFCVLADS ESGGHITHSG MVGMGVSCTV TREDGTNDYK   600
DDDDK                                                                605

SEQ ID NO: 20           moltype = DNA   length = 1818
FEATURE                 Location/Qualifiers
source                  1..1818
                        mol_type = other DNA
                        organism = synthetic construct
SEQUENCE: 20
atgggcagcc ggatcgtgat caaccgggag cacctgatga tcgaccggcc ctacgtgctg    60
ctggccgtgc tgttcgtgat gttcctgagc ctgatcggct tgctagccat tgctggaatc   120
cggctgcaca gagccgccat ctacaccgcc gagatccaca gagcctgag  caccaacctg   180
gacgtgacca acagcatcga gcatcaggtc aaggacgtgc tgaccccct  gtttaagatc   240
atcggcgacg aagtgggcct gcggaccccc cagagattca ccgacctggt caagttcatc   300
agcgacaaga tcaagttcct gaaccccgac cgggagtacg acttccggga cctgacctgg   360
tgcatcaacc cccccgagcg gatcaagctg gactacgacc agtactgcgc cgatgtggcc   420
gccgagaac  tgatgaatgc cttggtgaac tcaactctac tggagaccga aacaaccaat   480
cagttcctag ctgtctcaaa gggaaactgc tcagggccca ctacaatcag aggtcaattc   540
tcaaacatgt cgctgtccct gttagacttg tatttaggtc gaggttacaa tgtgtcatct   600
atagtcacta tgacatccca gggaatgtat ggggaacttt accagtggaa aaagcctaat   660
ctgagcagca aaaggtcaga gttgtcacaa ctgagcatgt accgagtgtt tgaagtaggt   720
gttatcagaa atccgggttt ggggctccg  tgttccata  tgacaaacta tcttgagcaa   780
ccagtcagta atgatctcag caactgtatg gtggctttgg gggagctcaa actcgcagcc   840
cttttgtcacg gggaagattc tatcacaatt ccctatcagg gatcagggaa aggtgtcagc   900
ttccagctcg tcaagctagg tgtctggaaa tccccaacg  acatgcaatc ctgggtcccc   960
ttatcaacgg atgatccagt gatagacagg ctttacctct catctcacag aggtgttatc  1020
gctgacaacc aagcaaaatg ggctgtcccg acaacacgaa cagatgacaa gttgcgaatg  1080
gagacatgct ccaacaggc  gtgtaagggt aaaatccaag cactctgcga gaatcccgag  1140
tgggcaccat tgaaggataa caggattcct tcatacggg  tcttgtctgt tgatctgagt  1200
ctgacagttg agcttaaaat caaaattgct tcgggattcg gccattgat  cacacacgtg  1260
tcagggatgg acctatacaa atccaaccac aacaatgtgt attggctgac tatcccgcca  1320
atgaagaacc tagccttagg tgtaatcaac acattggagt ggataccgag attcaaggtt  1380
agtcccgcgc tcttcaatgt cccaattaag aagcaggcg  gagactgcca tgccccaaca  1440
tacctacctg cggaggtgga tggtgatgtc aaactcagtt ccaatctgtg gattctacct  1500
ggtcaagatc tccaatatgt tttggcaacc tacgatactt ccgcggttga acatgctgtg  1560
gtttattacg tttacagccc aagccgctca ttttcttact tttatccttt  taggttgcct  1620
ataaaggggg tccccatcga attacaagtg gaatgcttca catgggacca aaaactctgg  1680
tgccgtcact tctgtgtgct tgcggactca gaatctggtg gacatatcac tcactctggg  1740
atggtgggca tgggagtcag ctgcacagtc acccgggaag atggaaccaa tgactacaaa  1800
gacgatgacg acaagtga                                                 1818

SEQ ID NO: 21           moltype = AA   length = 605
FEATURE                 Location/Qualifiers
REGION                  1..605
                        note = Synthetic Polypeptide
source                  1..605
                        mol_type = protein
                        organism = synthetic construct
SEQUENCE: 21
MGSRIVINRE HLMIDRPYVL LAVLFVMFLS LIGLLAIAGI RLHRAAIYTA EIHKSLSTNL    60
DVTNSIEHQV KDVLTPLFKI IGDEVGLRTP QRFTDLVKFI SDKIKFLNPD REYDFRDLTW   120
CINPPERIKL DYDQYCADVA AEELMNALVN STLLETRTTN QFLAVSKGNC SGPTTIRGQF   180
SNMSLSLLDL YLGRGYNVSS IVTMTSQGMY GGTYLVEKPN LSSKRSELSQ LSMYRVFEVG   240
VIRNPGLGAP VFHMTNYLEQ PVSNDLSNCM VALGELKLAA LCHGEDSITI PYQGSGKGVS   300
FQLVKLGVWK SPTDMQSWVP LSTDDPVIDR LYLSSHRGVI ADNQAKWAVP TTRTDDKLRM   360
ETCFQQACKG KIQALCENPE WAPLKDNRIP SYGVLSVDLS LTVELKIKIA SGFGPLITHG   420
SGMDLYKSNH NNVYWLTIPP MKNLALGVIN TLEWIPRFKV SPALFNVPIK EAGGDCHAPT   480
YLPAEVDGDV KLSSNLVILP GQDLQYVLAT YDTSAVEHAV VYYVYSPSRS FSYFYPFRLP   540
IKGVPIELQV ECFTWDQKLW CRHFCVLADS ESGGHITHSG MVGMGVSCTV TREDGTNDYK   600
DDDDK                                                                605

SEQ ID NO: 22           moltype = DNA   length = 1785
FEATURE                 Location/Qualifiers
source                  1..1785
                        mol_type = other DNA
                        organism = synthetic construct
SEQUENCE: 22
atgaagaaga tcaacgaggg cctgctggac agcaagatcc tgagcgcctt caacaccgtg    60
attgccctgc tgggctctat cgtgatcatc gtgatgaaca tcatgatcat ccagaactac   120
acccggtcca ccgacaacca ggccgtgatt aaggatgctc tgcagggaat ccagcagcag   180
atcaaaggcc tggccgacaa gatcggcaca gagatcggcc taaggtgtc  cctgatcgac   240
accagcagca ccatcacaat cccgccaat  atcggactgt gggaagcaa  gatcagccag   300
agcaccgcca gcatcaacga gaacgtgaac gagaagtgca gttcaccct  gcctccactg   360
aagatccacg agtgcaacat cagctgcccc aatcctctgc cattcagaga gtacagaccc   420
cagacagagg gcgtgtccaa tctcgtgggc ctgcctaaca  acatctgcct gcagaaaacc   480
agcaaccaga tcctgaagcc taagctgatc  tcctacacac tgcccgtcgt gggccagagc   540
ggcacctgta ttacagatcc tctgctggcc atggacgagg ctactttgc  ctacagccac   600
ctggaaagaa tcggcagctg tagccgggga gtgtccaagc agagaatcat cggcgtgggc   660
```

```
gaagtgctgg atagaggcga cgaagtgccc agcctgttca tgaccaatgt gtggacccct    720
cctaatccta acaccgtgta ccactgcagc gccgtgtaca acaacgagtt ctactacgtg    780
ctgtgcgccg tgtccacagt gggcgaccct atcctgaaca gcacctattg gagcggcagc    840
ctgatgatga ccagactggc cgtgaagccc aagagcaatg gcggcggata caaccagcat    900
cagctggccc tgcggtccat cgagaagggc agatacgaca agtgatgcc ttacggcccc    960
agcggcatca agcaaggcga taccctgtac tttcccgccg tgggatttct cgtgcggacc   1020
gagttcaagt acaacgacag caactgcccc atcaccaagt gccagtacag caagcccgag   1080
aactgcagac tgagcatggg catcagacc aacagccact acatcctgag aagcggcctg   1140
ctgaagtaca acctgagcga cggcgagaac cccaaggtgg tgttcatcga gatcagcgac   1200
cagcggctgt ctatcggcag ccctccaag atctacgacc tctgggcca gccagtgttc   1260
taccaggcca gctttagctg ggacaccatg atcaagttcg gcgacgtgct gaccgtgaat   1320
cccctggtgg tcaactggcg gaacaatacc gtgatcagcc ggcctggcca gtctcagtgc   1380
cccagattca ataccgtgcc tgccatttgc gccgaaggcg tgtacaatga cgccttcctg   1440
atcgatcgga tcaactggat ctctgccggc gtgttcctgg actctaatgc cacagccgcc   1500
aatcctgtgt tcaccgtgtt caaggacaat gagatcctgt atcgggccca gctggcctcc   1560
gaggacacaa atgcccagaa aacaatcacc aactgctttc tgctcaagaa caagatctgg   1620
tgcatcagcc tggtggaaat ctacgacacc ggcgacaacg tgatcaggcc aagctgttc    1680
gccgtgaaga tccctgagca gtgtacaggc ggcggaggt ctggcggagg tggaagcgga   1740
ggcggtggat ctgctagcga ttacaaggat gacgacgata agtga                   1785

SEQ ID NO: 23            moltype = AA  length = 594
FEATURE                  Location/Qualifiers
REGION                   1..594
                         note = Synthetic Polypeptide
source                   1..594
                         mol_type = protein
                         organism = synthetic construct
SEQUENCE: 23
MKKINEGLLD SKILSAFNTV IALLGSIVII VMNIMIIQNY TRSTDNQAVI KDALQGIQQQ     60
IKGLADKIGT EIGPKVSLID TSSTITIPAN IGLLGSKISQ STASINENVN EKCKFTLPPL    120
KIHECNISCP NPLPFREYRP QTEGVSNLVG LPNNICLQKT SNQILKPKLI SYTLPVVGQS    180
GTCITDPLLA MDEGYFAYSH LERIGSCSRG VSKQRIIGVG EVLDRGDEVP SLFMTNVWTP    240
PNPNTVYHCS AVYNNEFYYV LCAVSTVGDP ILNSTYWSGS LMMTRLAVKP KSNGGGYNQH    300
QLALRSIEKG RYDKVMPYGP SGIKQGDTLY FPAVGFLVRT EPFKYNDSNCP ITKCQYSKPE   360
NCRLSMGIRP NSHYILRSGL LKYNLSDGEN PKVVFIEISD QRLSIGSPSK IYDSLGQPVF    420
YQASFSWDTM IKFGDVLTVN PLVVNWRNNT VISRPGQSQC PRFNTCPAIC AEGVYNDAFL    480
IDRINWISAG VFLDSNATAA NPVFTVFKDN EILYRAQLAS EDTNAQKTIT NCFLLKNKIW    540
CISLVEIYDT GDNVIRPKLF AVKIPEQCTG GGGSGGGGS GGGSASDYKD DDDK           594

SEQ ID NO: 24            moltype = AA  length = 609
FEATURE                  Location/Qualifiers
REGION                   1..609
                         note = Synthetic Polypeptide
source                   1..609
                         mol_type = protein
                         organism = synthetic construct
SEQUENCE: 24
MSIGLLCCAA LSLLWAGPVN AGVTQTPKFQ VLKTGQSMTL QCAQDMNHEY MSWYRQDPGM     60
GLRLIHYSVG AGITDQGEVP NGYNVSRSTT EDFPLRLLSA APSQTSVYFC ASSYVGNTGE    120
LFFGEGSRLT VLEDLKNVFP PEVAVFEPSE AEISHTQKAT LVCLATGFYP DHVELSWWVN    180
GKEVHSGVST DPQPLKEQPA LNDSRYCLSS RLRVSATFWQ NPRNHFRCQV QFYGLSENDE    240
WTQDRAKPVT QIVSAEAWGR ADCGFTSESY QQGVLSATIL YEILLGKATL YAVLVSALVL    300
MAMVKRKDSR GGSATNFSLL KQAGDVEENP GPMETLLGLL ILWLQLQWVS SKQEVTQIPA    360
ALSVPEGENL VLNCSFTDSA IYNLQWFRQD PGKGLTSLLL IQSSQREQTS GRLNASLDKS    420
SGSSTLYIAA SQPGDSATYL CAVRPTSGGS YIPTFGRGTS LIVHPYIQNP DPAVYQLRDS    480
KSSDKSVCLF TDFDSQTNVS QSKDSDVYIT DKTVLDMRSM DFKSNSAVAW SNKSDFACAN    540
AFNNSIIPED TFFPSPESSC DVKLVEKSFE TDTNLNFQNL SVIGFRILLL KVAGFNLLMT    600
LRLWSSAAA                                                            609

SEQ ID NO: 25            moltype = AA  length = 609
FEATURE                  Location/Qualifiers
REGION                   1..609
                         note = Synthetic Polypeptide
source                   1..609
                         mol_type = protein
                         organism = synthetic construct
SEQUENCE: 25
MSIGLLCCAA LSLLWAGPVN AGVTQTPKFQ VLKTGQSMTL QCAQDMNHEY MSWYRQDPGM     60
GLRLIHYSVG AQTTDQGEVP NGYNVSRSTI EDFPLRLLSA APSQTSVYFC ASSYLGNTGE    120
LFFGEGSRLT VLEDLKNVFP PEVAVFEPSE AEISHTQKAT LVCLATGFYP DHVELSWWVN    180
GKEVHSGVST DPQPLKEQPA LNDSRYCLSS RLRVSATFWQ NPRNHFRCQV QFYGLSENDE    240
WTQDRAKPVT QIVSAEAWGR ADCGFTSESY QQGVLSATIL YEILLGKATL YAVLVSALVL    300
MAMVKRKDSR GGSATNFSLL KQAGDVEENP GPMETLLGLL ILWLQLQWVS SKQEVTQIPA    360
ALSVPEGENL VLNCSFTDSA IYNLQWFRQD PGKGLTSLLL IQSSQREQTS GRLNASLDKS    420
SGSSTLYIAA SQPGDSATYL CAVRPMIGGT YIPTFGRGTS LIVHPYIQNP DPAVYQLRDS    480
KSSDKSVCLF TDFDSQTNVS QSKDSDVYIT DKTVLDMRSM DFKSNSAVAW SNKSDFACAN    540
AFNNSIIPED TFFPSPESSC DVKLVEKSFE TDTNLNFQNL SVIGFRILLL KVAGFNLLMT    600
LRLWSSAAA                                                            609
```

```
SEQ ID NO: 26          moltype = AA   length = 609
FEATURE                Location/Qualifiers
REGION                 1..609
                       note = Synthetic Polypeptide
source                 1..609
                       mol_type = protein
                       organism = synthetic construct
SEQUENCE: 26
MSIGLLCCAA LSLLWAGPVN AGVTQTPKFQ VLKTGQSMTL QCAQDMNHEY MSWYRQDPGM  60
GLRLIHYSVG AGTTDRGEVP NGYNVSRSTI EDFPLRLLSA APSQTSVYFC ASSYVGDTGE 120
LFFGEGSRLT VLEDLKNVFP PEVAVFEPSE AEISHTQKAT LVCLATGFYP DHVELSWWVN 180
GKEVHSGVST DPQPLKEQPA LNDSRYCLSS RLRVSATFWQ NPRNHFRCQV QFYGLSENDE 240
WTQDRAKPVT QIVSAEAWGR ADCGFTSESY QQGVLSATIL YEILLGKATL YAVLVSALVL 300
MAMVKRKDSR GGSATNFSLL KQAGDVEENP GPMETLLGLL ILWLQLQWVS SKQEVTQIPA 360
ALSVPEGENL VLNCSFTDSA IYNLQWFRQD PGKGLTSLLL IQSSQREQTS GRLNASLDKS 420
SGSSTLYIAA SQPGDSATYL CAVRPLLDGT YIPTFGRGTS LIVHPYIQNP DPAVYQLRDS 480
KSSDKSVCLF TDFDSQTNVS QSKDSDVYIT DKTVLDMRSM DFKSNSAVAW SNKSDFACAN 540
AFNNSIIPED TFFPSPESSC DVKLVEKSFE TDTNLNFQNL SVIGFRILLL KVAGFNLLMT 600
LRLWSSAAA                                                         609

SEQ ID NO: 27          moltype = AA   length = 609
FEATURE                Location/Qualifiers
REGION                 1..609
                       note = Synthetic Polypeptide
source                 1..609
                       mol_type = protein
                       organism = synthetic construct
SEQUENCE: 27
MSIGLLCCAA LSLLWAGPVN AGVTQTPKFQ VLKTGQSMTL QCAQDMNHEY MSWYRQDPGM  60
GLRLIHYSVA IQTTDQGEVP NGYNVSRSTI EDFPLRLLSA APSQTSVYFC ASSYLGNTGE 120
LFFGEGSRLT VLEDLKNVFP PEVAVFEPSE AEISHTQKAT LVCLATGFYP DHVELSWWVN 180
GKEVHSGVST DPQPLKEQPA LNDSRYCLSS RLRVSATFWQ NPRNHFRCQV QFYGLSENDE 240
WTQDRAKPVT QIVSAEAWGR ADCGFTSESY QQGVLSATIL YEILLGKATL YAVLVSALVL 300
MAMVKRKDSR GGSATNFSLL KQAGDVEENP GPMETLLGLL ILWLQLQWVS SKQEVTQIPA 360
ALSVPEGENL VLNCSFTDSA IYNLQWFRQD PGKGLTSLLL ITPWQREQTS GRLNASLDKS 420
SGSSTLYIAA SQPGDSATYL CAVRPLLDGT YIPTFGRGTS LIVHPYIQNP DPAVYQLRDS 480
KSSDKSVCLF TDFDSQTNVS QSKDSDVYIT DKTVLDMRSM DFKSNSAVAW SNKSDFACAN 540
AFNNSIIPED TFFPSPESSC DVKLVEKSFE TDTNLNFQNL SVIGFRILLL KVAGFNLLMT 600
LRLWSSAAA                                                         609

SEQ ID NO: 28          moltype = AA   length = 30
FEATURE                Location/Qualifiers
REGION                 1..30
                       note = Synthetic Polypeptide
source                 1..30
                       mol_type = protein
                       organism = synthetic construct
SEQUENCE: 28
VVVISAILAL VVLTIISLII LIMLWQKKPR                                   30

SEQ ID NO: 29          moltype = AA   length = 60
FEATURE                Location/Qualifiers
REGION                 1..60
                       note = Synthetic Polypeptide
REGION                 7..60
                       note = MISC_FEATURE - may be absent
source                 1..60
                       mol_type = protein
                       organism = synthetic construct
SEQUENCE: 29
GAPGASGAPG ASGAPGASGA PGASGAPGAS GAPGASGAPG ASGAPGASGA PGASGAPGAS  60

SEQ ID NO: 30          moltype = AA   length = 50
FEATURE                Location/Qualifiers
REGION                 1..50
                       note = Synthetic Polypeptide
REGION                 6..50
                       note = MISC_FEATURE - may be absent
source                 1..50
                       mol_type = protein
                       organism = synthetic construct
SEQUENCE: 30
GGGGSGGGGS GGGGSGGGGS GGGGSGGGGS GGGGSGGGGS GGGGSGGGGS              50

SEQ ID NO: 31          moltype = AA   length = 603
FEATURE                Location/Qualifiers
REGION                 1..603
                       note = Synthetic Polypeptide
source                 1..603
```

```
                        mol_type = protein
                        organism = synthetic construct
SEQUENCE: 31
MSIGLLCCAA  LSLLWAGPVN  ADAGVTQSPT  HLIKTRGQQV  TLRCSPKQGH  DTVSWYQQAL   60
GQGPQFIFQY  YEEEERQRGN  FPDRFSGHQF  PNYSSELNVN  ALLLGDSALY  LCASSDTVSY  120
EQYFGPGTRL  TVTEDLKNVF  PPEVAVFEPS  EAEISHTQKA  TLVCLATGFY  PDHVELSWWV  180
NGKEVHSGVS  TDPQPLKEQP  ALNDSRYCLS  SRLRVSATFW  QDPRNHFRCQ  VQFYGLSEND  240
EWTQDRAKPV  TQIVSAEAWG  RADCGFTSES  YQQGVLSATI  LYEILLGKAT  LYAVLVSALV  300
LMAMVKRKDS  RGGSATNFSL  LKQAGDVEEN  PGPMETLLGL  LILWLQLQWV  SSKEVEQNSG  360
PLSVPEGAIA  SLNCTYSDRG  SQSFFWYRQY  SGKSPELIMF  IYSNGDKEDG  RFTAQLNKAS  420
QYISLLIRDS  KLSDSATYLC  AVRTNSGYAL  NFGKGTSLLV  TPHIQKPDPA  VYQLRDSKSS  480
DKSVCLFTDF  DSQTNVSQSK  DSDVYITDKT  VLDMRSMDFK  SNSAVAWSNK  SDFACANAFN  540
NSIIPEDTFF  PSPESSCDVK  LVEKSFETDT  NLNFQNLSVI  GFRILLLKVA  GFNLLMTLRL  600
WSS                                                                    603

SEQ ID NO: 32           moltype = DNA  length = 1812
FEATURE                 Location/Qualifiers
misc_feature            1..1812
                        note = Synthetic Polynucleotide
source                  1..1812
                        mol_type = other DNA
                        organism = synthetic construct
SEQUENCE: 32
atgtctatcg ggctgctgtg ttgcgccgct ctgtccctgc tgtgggccgg acctgtcaat   60
gctgatgctg gcgtaacgca gagcccgaca catctgataa aaacaagagg ccaacaagtt  120
actctgaggt gcagtccaaa gcaagggcac gatactgtgt cttggtacca acaggctctt  180
gggcaagggc cacaattcat ctttcaatac tacgaggaag aagagcgcca acgaggaaac  240
tttcctgatc gcttcagcgg tcaccaattt cctaattaca gttccgaatt gaatgtaaat  300
gctctcctgc tcggcgatag cgctctgtac ctttgtgcct cctccgacac cgtaagctat  360
gaacaatact ttggtcctgg cactcgcctc accgtaaccg aagatctgaa gaacgttttt  420
ccgccagagg tcgccgtttt tgaaccaagc gaagcggaaa tcagtcacac acagaaggca  480
acactcgttt gtctggccac tggcttctac cccgatcacg tcgaactttc atggtgggtc  540
aatggaaagg aagttcacag cggtgtaagt actgatccac agcctctcaa agagcagccc  600
gccttgaatg acagcagata ttgtttgagt tcacggttga gagtaagcgc taccttctgg  660
caagatcctc gcaatcactt ccgatgtcag gtgcagtttt atggactgtc agaaaatgat  720
gaatggacac aagataggc  taaacccgtg acccaaatcg tgagcgctga ggcatggggt  780
cgagcagact gcggcttcac aagtgaatca taccagcagg gggtgctgag cgccactatc  840
ctgtacgaga ttctgctggg aaaggctacc ctgtatgcag tgctggtctc cgccctggtg  900
ctgatggcta tggcaagcg aaaagacagc cggggccgca acaaactcttttccctg  960
ctgaaacagg ccggcgatgt ggaggaaat cctgggccaa tggagactct gctgggactg  1020
ctgatcctgt ggctgcagct gcagtgggtg tcaagcaaag aagtagaaca aaactcaggc  1080
cccctgtccg taccagaggg agctatagcg tctctcaatt gtacgtacag cgaccggggc  1140
tcccaatcat tcttctggta tcggcagtac agcgggaaa gtccggaatt gattatgttc  1200
atatattcta acggcgacaa agaggacggg cgatttacgc cacaactgaa caaagcgagc  1260
caatacatca gtcttcttat tcgagatagc aaattgtctg actccgctac ataccctctgt  1320
gcagtccgga ctaactccgg ttacgccttg aacttgggaa aagggacgtc attgttggtc  1380
acgccgcata cagaagcc cgatcctgca gtttaccaaa tccggggactc aaagtcttcc  1440
gataagagtg tctgtcttt caccgacttc gatagtcaaa cgaatgttag ccagtctaag  1500
gacagcgatg tttatatcac cgacaaaacc gtcctcgaca tgaggtctat ggactttaag  1560
agcaacagcg cggtagcgtg gtcaaataag agcgactttg cttgcgcgaa cgcttttcaat  1620
aattcaatca tacccgagga tactttcttc ccaagtccgg aatctagttg tgacgtgaag  1680
ctggtcgaga aaagtttcga aacagatact aacctgaatt ttcagaacct gtcagtgatc  1740
ggcttccgga ttctgctgct gaaggtcgcc gggttcaatc tgctgatgac cctgagactg  1800
tggtcaagct ga                                                      1812

SEQ ID NO: 33           moltype = AA  length = 609
FEATURE                 Location/Qualifiers
REGION                  1..609
                        note = Synthetic Polypeptide
source                  1..609
                        mol_type = protein
                        organism = synthetic construct
SEQUENCE: 33
MGTRLLFWVA  FCLLGADHTG  AGVSQSPSNK  VTEKGKDVEL  RCDPISGHTA  LYWYRQRLGQ   60
GLEFLIYFQG  NSAPDKSGLP  SDRFSAERTG  ESVSTLTIQR  TQQEDSAVYL  CASSQTQLWE  120
TQYFGPGTRL  LVLEDLKNVF  PPEVAVFEPS  EAEISHTQKA  TLVCLATGFY  PDHVELSWWV  180
NGKEVHSGVS  TDPQPLKEQP  ALNDSRYCLS  SRLRVSATFW  QNPRNHFRCQ  VQFYGLSEND  240
EWTQDRAKPV  TQIVSAEAWG  RADCGFTSES  YQQGVLSATI  LYEILLGKAT  LYAVLVSALV  300
LMAMVKRKDS  RGGSATNFSL  LKQAGDVEEN  PGPMEKNPLA  APLLILWFHL  DCVSSILNVE  360
QSPQSLHVQE  GDSTNFTCSF  PSSNFYALHW  YRWETAKSPE  ALFVMTLNGD  EKKKGRISAT  420
LNTKEGYSYL  YIKGSQPEDS  ATYLCAFITG  NQFYFGTGTS  LTVIPNIQNP  DPAVYQLRDS  480
KSSDKSVCLF  TDFDSQTNVS  QSKDSDVYIT  DKTVLDMRSM  DFKSNSAVAW  SNKSDFACAN  540
AFNNSIIPED  TFFPSPESSC  DVKLVEKSFE  TDTNLNFQNL  SVIGFRILLL  KVAGFNLLMT  600
LRLWSSAAA                                                             609

SEQ ID NO: 34           moltype = DNA  length = 1830
FEATURE                 Location/Qualifiers
misc_feature            1..1830
                        note = Synthetic Polynucleotide
```

```
source                  1..1830
                        mol_type = other DNA
                        organism = synthetic construct
SEQUENCE: 34
atgggcacac ggttgctgtt ttgggttgct ttctgcctgc tcggcgcaga tcacacggga    60
gcggggtta gtcagtcccc tagcaataaa gtgacggaaa aagggaaaga tgtcgagctg    120
aggtgtgatc caatttctgg acacactgcc ctctactggt atagacaacg ccttggtcag   180
gggctggagt tccttatcta tttccagggc aactccgcgc cgacaaaag tggtctcccg    240
agcgaccggt tttcagcgga gcgcacgggt gaaagtgtta gcacactgac aatccaaccg   300
acgcagcagg aggatagtgc tgtttatctg tgtgcctcta gtcagactca actttgggga   360
actcaatact tcggcctgg tacgcgcctc tcgttcttg aagacctgaa gaatgtcttc     420
cccctgagg tggccgtctt tgaaccttca gaggctgaaa ttagcacac tcagaaagct     480
accctggtgt gtctggcaac tggcttctat ccagatcacg tggagctgag ctggtgggtc   540
aacggaagg aagtgcattc cggagtctct acagacccac agccctgaa agagcagccc     600
gccctgaatg attcccggta ttgcctgtct agtcggctga gagtgtctgc tacctttgg    660
cagaacccta ggaatcattt ccgctgtcag gtgcagttt acggcctgtc tgagaatgac    720
gaatggaccc aggatcgagc taagcctgtg acacagatcg tcagtgcaga ggcttgggga   780
cgagcagact gcggcttcac aagtgaatca taccagcagg gtgctgag cgccactatc     840
ctgtacgaga ttctgctggg aaaggctacc ctgtatgcag tgctggtctc cgccctggtg   900
ctgatggcta tggtcaagcg aaaagacagc cggggcgggt ccgcaacaaa cttttccctg   960
ctgaaacagg ccggcgatgt ggaggaaaat cctgggccaa tggaaaagaa tccattggct   1020
gcaccctgc ttatactctg gtttcacttg gactgcgtat cctcaatttt gaatgttgaa    1080
caatcacccc agagtctcca cgtccaagaa ggggactcaa caaactttac ctgtagtttc   1140
ccctcaagta acttctacgc tctccactgg tatcggtggg agactgccaa gagccccgaa   1200
gctctcttcg taatgaccct taatggagac gaaaaaaga agggagaat aagtgccact     1260
ctgaatacca aagagggcta ttcctatctc tacataaagg aagtcaacc tgaggattcc    1320
gccacttacc tgtgcgcgtt catcactgga aaccagttct atttcgggac cggaacatct   1380
ctgactgtaa tccaaatat tcagaacccc gatcctgccg tctatcagct gagggacagc    1440
aagagctccg ataaatccgt gtgtctgttc acagactttg attctcagac taatgtgagc   1500
cagtccaagg acagtgatgt gtacatcacc gacaaaacag tcctggatat gcgcagcatg   1560
gacttcaagt ctaacagtgc agtggcctgg agtaacaagt cagacttcgc ttgcgcaaac   1620
gcctttaaca attcaatcat tcccgaggat accttctttc caagcccga atctagttgt    1680
gacgtgaagc tggtcgagaa aagtttcgaa acagatacta acctgaattt tcagaacctg   1740
tcagtgatcg gcttccggat tctgctgctg aaggtcgccg ggttcaatct gctgatgacc   1800
ctgagactgt ggtcaagcgc ggccgcctga                                    1830

SEQ ID NO: 35         moltype = AA  length = 474
FEATURE               Location/Qualifiers
REGION                1..474
                      note = Synthetic Polypeptide
source                1..474
                      mol_type = protein
                      organism = synthetic construct
SEQUENCE: 35
MSRSVALAVL ALLSLSGLEA SLYNTVATLG GGASGGGGSG GGGSIQRTPK IQVYSRHPAE    60
NGKSNFLNCY VSGFHPSDIE VDLLKNGERI EKVEHSDLSF SKDWSFYLLY YTEFTPTEKD   120
EYACRVNHVT LSQPKIVKWD RDMGGGGSGG GGSGGGGSGG GGSHSMRYFF TSVSRPGRGE   180
PRFIAVGYVD DTQFVRFDSD AASQRMEPRA PWIEQEGPEY WDGETRKVKA HSQTHRVDLG   240
TLRGAYNQSE AGSHTVQRMY GCDVGSDWRF LRGYHQYAYD GKDYIALKED LRSWTAADMA   300
AQTTKHKWEA AHVAEQLRAY LEGTCVEWLR RYLENGKETL QRTDAPKTHM THHAVSDHEA   360
TLRCWALSFY PAEITLTWQR DGEDQTQDTE LVETRPAGDG TFQKWAAVVV PSGQEQRYTC   420
HVQHEGLPKP LTLRWEPSSQ PTIPIVGIIA GLVLFGAVIT GAVVAAVMWR RKSS         474

SEQ ID NO: 36         moltype = DNA  length = 1425
FEATURE               Location/Qualifiers
misc_feature          1..1425
                      note = Synthetic Polynucleotide
source                1..1425
                      mol_type = other DNA
                      organism = synthetic construct
SEQUENCE: 36
atgagccgca gcgtggcgct ggcggtgctg gcgctgctga gcctgagcgg cctggaagcg    60
agcctttaca cacggtcgc gacactgggt ggaggagcta gcggaggtgg tggtagtggt   120
ggtggttggtt ccatacaaag aactccaaag atccaagttt acagtagaca tcctgctgaa   180
aacggtaaat ctaatttctt gaactgttac gtctccggtt tccacccaag tgatatagaa   240
gttgactgt gaaaaatgg tgaaagaatc gaaaaggttg aacattcaga tttgtctttt    300
tctaaggact ggtccttcta tttgttgtac tacacagagt tcactccaac tgaaaaggat   360
gaatacgctt gcagagtaa tcatgtaacc ttgtctcaac ctaaaatcgt taagtgggat   420
agagacatgg gtggtggcgg cagtggcggt ggtggcagcg gtggtggaggc cagcggtgg   480
ggtggttccc atagtatgag atattttctt acttctgttt caagaccagg tagaggtgaa   540
cctagattca tcgcagtcgg ttacgttgat gacacacaat tgtaagatt cgattccgac    600
gctgcaagtc aaagaatgga accaagagca ccttggattaa acaagaagg tccagaatat   660
tgggatggtg aaactagaaa agttaaggcc attctcaaa ctcacagagt agatttgggt    720
acattaagag gcgcttataa tcaatctgaa gcaggttcac atactgtaca gagaatgtac   780
ggttgtgatg tcggttcaga ctggagattt ttgagaggtt atcaccaata tgcttacgat   840
ggtaaagact acattgcatt gaaggaagat ttgagatcct ggaccgccgc tgacatggca   900
gcccaaacta caaacataa gtggaagct gcacacgtag cagaacaatt gagagcctat   960
ttggaaggta catgtgtcga atggttgaga agatacttag aaaacggtaa agaaacattg   1020
caaagaaccg atgctccaaa gactcatatg acacatcacg ccgttagtga tcacgaagct   1080
```

```
actttgagat gctgggcatt atcttttac cctgccgaaa tcacattgac ctggcaaaga   1140
gatggtgaag accaaaccca agatactgaa ttagttgaaa ccagaccagc aggtgacggt   1200
actttccaaa aatgggccgc tgttgtagtc ccttcaggtc aagaacaaag atacacatgc   1260
catgtccaac acgaaggttt accaaagcca ttgacattga tgggaacc atcctctcag     1320
cctacaatac caatagtcgg cataatcgct ggactggtcc tgttcggggc ggtaatcacg   1380
ggagctgtag tcgctgcggt gatgtggcgc agaaaaagct cctga                   1425
```

SEQ ID NO: 37        moltype = AA   length = 474
FEATURE               Location/Qualifiers
REGION                1..474
                        note = Synthetic Polypeptide
source                1..474
                        mol_type = protein
                        organism = synthetic construct
SEQUENCE: 37

```
MSRSVALAVL ALLSLSGLEA NLVPMVATVG ASGGSGGGSG GGGSIQRTPK IQVYSRHPAE    60
NGKSNFLNCY VSGFHPSDIE VDLLKNGERI EKVEHSDLSF SKDWSFYLLY YTEFTPTEKD   120
EYACRVNHVT LSQPKIVKWD RDMGGGGSGG GGSGGGGSGG GGSHSMRYFF TSVSRPGRGE   180
PRFIAVGYVD DTQFVRFDSD AASQRMEPRA PWIEQEGPEY WDGETRKVKA HSQTHRVDLG   240
TLRGAYNQSE AGSHTVQRMY GCDVGSDWRF LRGYHQYAYD GKDYIALKED LRSWTAADMA   300
AQTTKHKWEA AHVAEQLRAY LEGTCVEWLR RYLENGKETL QRTDAPKTHM THHAVSDHEA   360
TLRCWALSFY PAEITLTWQR DGEDQTQDTE LVETRPAGDG TFQKWAAVVV PSGQEQRYTC   420
HVQHEGLPKP LTLRWEPSSQ PTIPIVGIIA GLVLFGAVIT GAVVAAVMWR RKSS         474
```

SEQ ID NO: 38        moltype = DNA  length = 1425
FEATURE               Location/Qualifiers
misc_feature        1..1425
                        note = Synthetic Polynucleotide
source                1..1425
                        mol_type = other DNA
                        organism = synthetic construct
SEQUENCE: 38

```
atgagccgca gcgtggcgct ggcggtgctg gcgctgctga gcctgagcgg cctggaagcg    60
aacttggttc cgatggtggc aaccgtaggt gctagcggag ggtccggcgg gggtagcggt   120
ggtgaggaa gcatacaaag aactccaaag atccaagttt acagtagaca tcctgctgaa   180
aacggtaaat ctaatttctt gaactgttac gtctccggtt tccacccaag tgatatagaa   240
gttgacttgt tgaaaaatgg tgaaagaatc gaaaagttg aacattcaga tttgtctttt   300
tctaaggact ggtccttcta ttgttgtac tacacagagt tcactccaac tgaaaaggat   360
gaatacgctt gcagagttaa tcatgtaacc ttgtctcaac ctaaaatcgt taagtggat   420
agagacatgg gtggtggcgg cagtggtggc ggggggcagcg gtggtggggg cagcggtggt   480
ggtggttccc atagtatgag atattctt acttctgtt caagaccagg tagaggtgaa    540
cctagattca tcgcagtcgg ttacgttgat gacacacaat ttgtaagatt cgattccgac   600
gctcaagtc aaagaatgga accaagagca ccttggattg aacaagaag tccagaatat    660
tgggatggtg aaactagaaa agttaaggcc cattctcaaa ctcacagagt agattgggt    720
acattaagag gtgcttataa tcaatctgaa gcaggttcac atacagtaca aagaatgtac   780
ggttgtgatg tcggttcaga ctggagattt ttgagaggtt atcaccaata tgcttacgat   840
ggtaaagact acattgcatt gaaggaaga tgatcct ggaccgccgc tgacatggca    900
gcccaaacta caaaacataa gtgggaagct gcacacgtag caaacaatt gagagcctat   960
ttgaaggta catgtgtcga atggttgaga agatacttag aaaacggtaa agaaacattg   1020
caaagaaccg atgctccaaa gactcatatg acacatcacg ccgttagtga tcacgaagct   1080
actttgagat gctgggcatt atcttttac cctgccgaaa tcacattgac ctggcaaaga   1140
gatggtgaag accaaaccca agatactgaa ttagttgaaa ccagaccagc aggtgacggt   1200
actttccaaa aatgggccgc tgttgtagtc ccttcaggtc aagaacaaag atacacatgc   1260
catgtccaac acgaaggttt accaaagcca ttgacattga tgggaacc atcctctcag     1320
cctacaatac caatagtcgg cataatcgct ggactggtcc tgttcggggc ggtaatcacg   1380
ggagctgtag tcgctgcggt gatgtggcgc agaaaaagct cctga                   1425
```

SEQ ID NO: 39        moltype = AA   length = 482
FEATURE               Location/Qualifiers
REGION                1..482
                        note = Synthetic Polypeptide
source                1..482
                        mol_type = protein
                        organism = synthetic construct
SEQUENCE: 39

```
MATGSRTSLL LAFGLLCLPW LQEGSAGILG FVFTLGCSGG SGGGSGGGGS IQRTPKIQVY    60
SRHPAENGKS NFLNCYVSGF HPSDIEVDLL KNGERIEKVE HSDLSFSKDW SFYLLYYTEF   120
TPTEKDEYAC RVNHVTLSQP KIVKWDRDMG GGGSGGGGSG GSGGGGSGG SHSMRYFFTS   180
VSRPGRGEPR FIAVGYVDDT QFVRFDSDAA SQRMEPRAPW IEQEGPEYWD GETRKVKAHS   240
QTHRVDLGTL RGCYNQSEAG SHTVQRMYGC DVGSDWRFLR GYHQYAYDGK DYIALKEDLR   300
SWTAADMAAQ TTKHKWEAAH VAEQLRAYLE GTCVEWLRRY LENGKETLQR TDAPKTHMTH   360
HAVSDHEATL RCWALSFYPA EITLTWQRDG EDQTQDTELV ETRPAGDGTF QKWAAVVVPS   420
GQEQRYTCHV QHEGLPKPLT LRWEPSSQPT IPIVGIIAGL VLFGAVITGA VVAAVMWRRK   480
SS                                                                 482
```

SEQ ID NO: 40        moltype = DNA  length = 1449
FEATURE               Location/Qualifiers
misc_feature        1..1449
                        note = Synthetic Polynucleotide

```
source                  1..1449
                        mol_type = other DNA
                        organism = synthetic construct
SEQUENCE: 40
atggcgacgg gttcaagaac ttccctactt cttgcatttg gcctgctttg tttgccgtgg    60
ttacaggagg gatccgcagg tatcctcgga tttgtgttta cacttggatg cagcggaggg   120
tccggcgggg gtagcggtgg tggaggaagc atacaaagaa ctccaaagat ccaagtttac   180
agtagacatc ctgctgaaaa cggtaaatct aatttcttga actgttacgt ctccggtttc   240
cacccaagtg atatagaagt tgacttgttg aaaaatggtg aaagaatcga aaaggttgaa   300
cattcagatt tgtctttttc taaggactgg tccttctatt tgttgtacta cacagagttc   360
actccaactg aaaaggatga aatacgcttg cagagttaat catgtaacct tgtctcaacct  420
aaaatcgtta agtgggatag agacatggga ggcggcggct ctggtggcag cggctctgga   480
ggttctggaa gtggaggcgg ctctggaggc tcccatagta tgagatattt cttttacttcc  540
gtttcaagac caggtagagg tgaacctaga ttcatcgcag ttcggttacgt tgatgacaca   600
caatttgtaa gattcgattc cgacgctgca agtcaaagaa tggaaccaag agcaccttgg   660
attgaacaag aaggtccaga atattgggat ggtgaaacta gaaaagttaa ggcccattct   720
caaactcaca gagtagattt gggtacatta agaggttgtt ataatcaatc tgaagcaggt   780
tcacatacag tacaaagaat tacggttgt gatgtcgatt cagactggag attttttgaa   840
ggttatcacc aatatgctta cgatggtaaa gactacattg cattgaagga agatttgaga   900
tcctggaccg ccgctgacat ggcagcccaa actacaaaac ataagtggga agctgcacac   960
gtagcagaac aattgagagc ctatttggaa ggtacatgtg tcgaatggtt gagaagatac  1020
ttagaaaacg gtaaagaaac attgcaaaga accgatgctc caaagactca tatgacacat  1080
cacgccgtta gtgatcacga agctactttg agatgctggg cattatcttt ttaccctgcc  1140
gaaatcacat tgacctggca agagatggtg aagaccaaa cccaagatac tgaattagtt   1200
gaaaccagac cagcaggtga cggtactttc caaaaatggg ccgctgttgt agtcccttca   1260
ggtcaagaac aaagatacac atgccatgtc aacacgaag tttaccaaa gccattgaca   1320
ttgagatggg aaccatcctc tcagcctaca ataccaatag tcggcataat cgctggactg  1380
gtcctgttcg gggcggtaat cacgggagct gtagtcgctg cggtgatgtg gcgcagaaaa  1440
agctcctga                                                          1449

SEQ ID NO: 41           moltype = AA  length = 474
FEATURE                 Location/Qualifiers
REGION                  1..474
                        note = Synthetic Polypeptide
source                  1..474
                        mol_type = protein
                        organism = synthetic construct
SEQUENCE: 41
MSRSVALAVL ALLSLSGLEA GILGFVFTLG GGASGGGSG GGGSIQRTPK IQVYSRHPAE     60
NGKSNFLNCY VSGFHPSDIE VDLLKNGERI EKVEHSDLSF SKDWSFYLLY YTEFTPTEKD   120
EYACRVNHVT LSQPKIVKWD RDMGGGGSGG GGSGGGGSGG GGSHSMRYFF TSVSRPGRGE   180
PRFIAVGYVD DTQFVRFDSD AASQRMEPRA PWIEQEGPEY WDGETRKVKA HSQTHRVDLG   240
TLRGAYNQSE AGSHTVQRMY GCDVGSDWRF LRGYHQYAYD GKDYIALKED LRSWTAADMA   300
AQTTKHKWEA AHVAEQLRAY LEGTCVEWLR RYLENGKETL QRTDAPKTHM THHAVSDHEA   360
TLRCWALSFY PAEITLTWQR DGEDQTQDTE LVETRPAGDG TFQKWAAVVV PSGQEQRYTC   420
HVQHEGLPKP LTLRWEPSSQ PTIPIVGIIA GLVLFGAVIT GAVVAAVMWR RKSS         474

SEQ ID NO: 42           moltype = DNA  length = 1425
FEATURE                 Location/Qualifiers
misc_feature            1..1425
                        note = Synthetic Polynucleotide
source                  1..1425
                        mol_type = other DNA
                        organism = synthetic construct
SEQUENCE: 42
atgagccgca gcgtggcgct ggcggtgctg gcgctgctga gcctgagcgg cctggaagcg    60
ggtatcctcg gatttgtgtt tacacttggt ggaggagcta gcggaggtgg tggtagtggt   120
ggtggtggtt ccatacaaag aactccaaag atccaagttt acagtagaca tcctgctgaa   180
aacggtaaat ctaatttctt gaactgttac gtctccggtt tccacccaag tgatatagaa   240
gttgacttgt tgaaaaatgg tgaaagaatc gaaaaggttg aacattcaga tttgtctttt   300
tctaaggact ggtccttcta tttgttgtac tacacagagt tcactccaac tgaaaaggat   360
gaatacgctt gcagagttaa tcatgtaacc ttgtctcaac ctaaaatcgt taagtgggat   420
agagacatgg gtggtggcgg cagtggtggc ggggcagcg gtggtgggg cagcggtggt    480
ggtggttccc atagtatgag atatttcttt acttctgttt caagaccagg tagaggtgaa   540
cctagattca tcgcagtcgg ttacgttgat gacacacaat tgtaagatt cgattccgac   600
gctgcaagtc aaagaatgga accaagagcc cttggattg aacaagaagg tccagaatat    660
tgggatggtg aaactagaaa agttaaggcc cattctcaaa ctcacagagt agatttgggt   720
acattaagag gtgcttataa tcaatctgaa gcaggttcac atacagtaca aagaatgtac   780
ggttgtgatg tcggttcaga ctggagattt ttgagaggtt atcaccaata tgcttacgat   840
ggtaaagact acattgcatt gaaggaagat ttgagatcct ggaccgccgc tgacatggca   900
gcccaaacta caaaacataa gtgggaagct gcacacgtag caacaattga gagcctat     960
ttggaaggta catgtgtcga atggttgaga agatacttag aaaacggtaa agaaacattg  1020
caaagaaccg atgctccaaa gactcatatg acacatcacg ccgttagtga tcacgaagct  1080
actttgagat gctgggcatt atctttttac cctgccgaaa tcacattgac ctggcaaaga  1140
gatggtgaag accaaaccca agatactgaa ttagttgaaa ccagaccagc aggtgacggt  1200
actttccaaa aatgggccgc tgttgtagtc ccttcaggtc aagaacaaag atacacatgc  1260
catgtccaac acgaaggttt accaaagcca ttgacattga gatgggaacc atcctctcag  1320
cctacaatac caatagtcgg cataatcgct ggactggtcc tgttcggggc ggtaatacg    1380
ggagctgtag tcgctgcggt gatgtggcgc agaaaaagct cctga                  1425
```

```
SEQ ID NO: 43           moltype = AA   length = 273
FEATURE                 Location/Qualifiers
REGION                  1..273
                        note = Synthetic Polypeptide
source                  1..273
                        mol_type = protein
                        organism = synthetic construct
SEQUENCE: 43
MGHTRRQGTS PSKCPYLNFF QLLVLAGLSH FCSGVIHVTK EVKEVATLSC GHNVSVEELA    60
QTRIYWQKEK KMVLTMMSGD MNIWPEYKNR TIFDITNNLS IVILALRPSD EGTYECVVLK   120
YEKDAFKREH LAEVTLSVKA DFPTPSISDF EIPTSNIRRI ICSTSGGFPE PHLSWLENGE   180
ELNAINTTVS QDPETELYAV SSKLDFNMTT NHSFMCLIKY GHLRVNQTFN WNTTKQEHFP   240
DNLLPSWAIT LISVNGIFVI CCLTYCFAPR CRE                                273

SEQ ID NO: 44           moltype = DNA   length = 822
FEATURE                 Location/Qualifiers
misc_feature            1..822
                        note = Synthetic Polynucleotide
source                  1..822
                        mol_type = other DNA
                        organism = synthetic construct
SEQUENCE: 44
atgggtcata cacgccgcca aggaacctca ccatctaagt gcccatatct gaatttcttt    60
caacttctcg tgctggcggg gctcagtcat ttctgcagtg gggtcattca cgttactaaa   120
gaggtcaagg aggtcgcaac attgagttgt ggccataagt gaactcgcg               180
cagacacgga tttactggca aaaggaaaag aagatggtgt tgacaatgat gagcggtgac   240
atgaacattt ggccagagta caaaaatcga acgatattcg atataaccaa taacttgtcc   300
atagtaatac ttgccttgcg accttctgac gagggaacgt atgaatgtgt agtgcttaag   360
tatgaaaaag atgcctttaa gcgggaacac ttggctgaag ttacactctc cgttaaggcg   420
gactttccta cgccgtctat atcccgactt gagatacccca cttctaacat tcgacgcatc   480
atttgctcaa cctcaggtgg tttcccagag cctcacttga gctggctgga aatggcgaa    540
gaacttaacg caatcaatac cacggtgtcc caagacccgg agacagagct gtacgccgtg   600
tcatccaaac tggatttaa catgacgaca aatcatagtt tcatgtgtct gatcaaatat    660
gggcatctca gggtgaatca gactttaat tggaacacta ccaaacaaga gcacttccca    720
gataatctgt tgccaagctg ggcgataact cttatctccg tcaacggtat cttcgtaatt   780
tgctgcctca cctattgttt cgcgcctcga tgccgagaat ga                      822

SEQ ID NO: 45           moltype = AA   length = 275
FEATURE                 Location/Qualifiers
REGION                  1..275
                        note = Synthetic Polypeptide
source                  1..275
                        mol_type = protein
                        organism = synthetic construct
SEQUENCE: 45
MDPQCTMGLS NILFVMAFLL SGAAPLKIQA YFNETADLPC QFANSQNQSL SELVVFWQDQ    60
ENLVLNEVYL GKEKFDSVHS KYMGRTSFDS DSWTLRLHNL QIKDKGLYQC IIHHKKPTGM   120
IRIHQMNSEL SVLANFSQPE IVPISNITEN VYINLTCSSI HGYPEPKKMS VLLRTKNSTI   180
EYDGVMQKSQ DNVTELYDVS ISLSVSFPDV TSNMTIFCIL ETDKTRLLSS PFSIELEDPQ   240
PPPDHIPWIT AVLPTVIICV MVFCLILWKW KKKKR                              275

SEQ ID NO: 46           moltype = DNA   length = 828
FEATURE                 Location/Qualifiers
misc_feature            1..828
                        note = Synthetic Polynucleotide
source                  1..828
                        mol_type = other DNA
                        organism = synthetic construct
SEQUENCE: 46
atggatccgc aatgcacaat ggggcttagc aacattctct tgtaatggc ttttctcctg    60
tccggtgcag cgcccctcaa gattcaggca tattttaacg aaaccgcgga cctcccttgt   120
cagttcgcaa atagtcagaa tcaaagtctc agtgagttgg tcgtattttg gcaggatcaa   180
gagaatctcg tcctgaacga ggtttacctg gcaaagtaa agtttgattc ggtgcatagt   240
aagtacatgg gtcgcacgtc ctttgactcc gacagctgga cacttaggct gcacaacctc   300
cagatcaaag ataagggtct ttaccagtgc attatacacc ataaaaaacc tactgggatg   360
atcaggattc accagatgaa cagcgagttg tcagtgttgg caaatttctc acaaccagaa   420
atagtaccta tctcaaacat caccgaaaac gtatatata acctcacctg ttctagtata   480
catggttatc cagagccaaa gaaaatgtcc gtgttgctga gaacaaagaa ctctacaata   540
gagtacgacg gagtgatgca aaaatcccag gacaacgtaa cagaactgta cgatgttagc   600
atctctcttt ctgtgagctt tcctgatgtg acatccaaca tgaccatttt ttgcatactc   660
gaaacagaca aaacgcgact tttgtcctcc ccctttcaa tcgagttgga ggatcccaa    720
cctcccccg accatatccc gtggatcacc gctgttcttc ctaccgtaat catctgtgtc   780
atggtattct gccttattct ctggaaatgg aagaaaaaga gcgatga                 828

SEQ ID NO: 47           moltype = AA   length = 551
FEATURE                 Location/Qualifiers
REGION                  1..551
                        note = Synthetic Polypeptide
```

| | | |
|---|---|---|
| source | 1..551<br>mol_type = protein<br>organism = synthetic construct | |
| SEQUENCE: 47 | | |

```
METDTLLLWV LLLWVPGSTG ADYKDDDDKD IQMTQSPSSL PASLGDRVTI NCQASQDISN    60
YLNWYQQKPG KAPKLLIYYT NKLADGVPSR FSGSGSGRDS SFTISSLESE DIGSYYCQQY   120
YNYPWTFGPG TKLEIKRADA KPTVSIFPPS SEQLGTGSAT LVCFVNNFYP KDINVKWKVD   180
GSEKRDGVLQ SVTDQDSKDS TYSLSSTLSL TKADYERHNL YTCEVTHKTS TAAIVKTLNR   240
NECGSGATNF SLLKQAGDVE ENPGPMVPCT LLLLLAAALA PTQTRAEVQL VESGGGLVQP   300
GKSLKLSCEA SGFTFSGYGM HWVRQAPGRG LESVAYITSS SINIKYADAV KGRFTVSRDN   360
AKNLLFLQMN ILKSEDTAMY YCARFDWDKN YWGQGTMVTV SSAKTTAPSV YPLAPACDST   420
TSTTNTVTLG CLVKGYFPEP VTVIWNSGAL TSGVHTFPSV LHSGLYSLSS SVTVPSSTWP   480
SQTVTCNVAH PASSTTVDLK IEAVGQDTQE VIVVPHSLPF KVVVISAILA LVVLTIISLI   540
ILIMLWQKKP R                                                       551
```

| | | |
|---|---|---|
| SEQ ID NO: 48<br>FEATURE<br>misc_feature | moltype = DNA   length = 1656<br>Location/Qualifiers<br>1..1656<br>note = Synthetic Polynucleotide | |
| source | 1..1656<br>mol_type = other DNA<br>organism = synthetic construct | |
| SEQUENCE: 48 | | |

```
atggaaaccg acaccttgct cctgtgggtt ctcctgttgt gggtgccggg atcaacggga    60
gctgattaca aggatgacga cgataaggac attcaaatga cccagtctcc ttccagcctg   120
ccagcgagcc tgggggacag agtgaccatt aactgtcagg cttcacagga tattacaat   180
tacctcaact ggtatcaaca gaagccaggc aaggccccca aactgctcat ttattacacg   240
aacaaactgg cggacggtgt tccttccaga tttagcggct ccggttccgg gcgggacagt   300
agctttacta taagcagttt ggaatccgag acataggtt cctattactg ccagcagtat   360
tacaattacc cttggacatt tggtccgggt actaagctcg agataaagcg ggccgatgcc   420
aagcccaccg tatcaatctt cccgccatcc agtgagcagc tcggtacaga aagcgcgact   480
ctggttttgtt tcgttaacaa ttttttatcct aaggacataa acgttaagtg aaggtagac   540
ggaagcgaga acgagatgg tgtattgcag agtgtcacag accaggattc caaagactcc   600
acatactccc tctcctcaac tcttagtctt acgaaggctg attacgaaag gcacaacctg   660
tatacgtgtg aggtcactca taaaaccagt actgcggcga ttgtaaaaac gctgaacagg   720
aacgaatgtg gaagtggtgc tacgaacttc tcactgctta agcaagctgg agatgttgag   780
gaaaaccctg gaccaatggt gccgtgcacc ctcctttgc ttttggccgc tgcgttggct   840
ccaacccaga ctagggcaga agtacagctt gtggaaagcg gcggagggct tgtgcagcct   900
ggcaaatccc tcaaactcag ttgtgaggct agtggcttca catttagcgg gtacggtatg   960
cactgggtcc gacaggcacc tgggcgcgga ttggaaagcg tcgcatacat tacaagctca  1020
agcataaata taaatatgc ggatgctgtc aaggggagat tcaccgtttc tagggataac  1080
gcgaagaacc ttttgttcct gcaaatgaac attctcaaga gcgaggacac ggctatgtac  1140
tattgtgcta ggttcgactg ggacaagaat tattgggaac aaggtactat ggttacagta  1200
agtagtgcta aaactactgc tccgtcagta tatcccctcg caccagcctg cgattctact  1260
accagcacta ctaatacagt aacactcggg tgcctcgtga aggggtattt ccctgaacca  1320
gttacggtca tctggaatag tggggccttg actagtggtg tacatacgtt cccatccgtc  1380
cttcactcag gactctacag cctcagctca agtgttaccg taccctcttc aacatggccg  1440
tctcagacag ttacgtgcaa cgtcgctcat cctgcaagtt ccacgactgt ggaccttaaa  1500
attgaagccg tcgccagga cacccaggag gtaattgttg tcccacattc acttccattc  1560
aaggtggtca tgatctctgc gatcctcgcg ctcgtcgttt tgacgatcat tagcctcatc  1620
atcctcatca tgttgtggca gaaaaagccc cggtaa                           1656
```

| | | |
|---|---|---|
| SEQ ID NO: 49<br>FEATURE<br>REGION | moltype = AA   length = 555<br>Location/Qualifiers<br>1..555<br>note = Synthetic Polypeptide | |
| source | 1..555<br>mol_type = protein<br>organism = synthetic construct | |
| SEQUENCE: 49 | | |

```
METDTLLLWV LLLWVPGSTG ADYKDDDDKY ELIQPSSASV TVGETVKITC SGDQLPKNFA    60
YWFQQKSDKN ILLLIYMDNK RPSGIPERFS GSTSGTTATL TISGAQPEDE AAYYCLSSYG   120
DNNDLVFGSG TQLTVLRGPK SSPKVTVFPP SPEELRTNKA TLVCLVNDFY PGSATVTWKA   180
NGATINDGVK TTKPSKQGQN YMTSSYLSLT ADQWKSHNRV SCQVTHEGET VEKSLSPAEC   240
LGSGATNFSL LKQAGDVEEN PGPMVPCTLL LLLAAALAPT QTRAEVLVE SGGDLVQPGS   300
SLKVSCAASG FTFSDFWMYW VRQAPGKGLE WVGRIKNIPN NYATEYADSV RGRFTISRDD   360
SRNSIYLQMN RLRVDDTAIY YCTRAGRFDH FDYWGQGTMV TVSSATTTAP SVYPLAPACD   420
STTSTTDTVT LGCLVKGYFP EPVTVSWNSG ALTSGVHTFP SVLHSGLYSL SSSVTVPSST   480
WPKQPITCNV AHPASSTKVD KKIEPRAVGQ DTQEVIVVPH SLPFKVVVIS AILALVVLTI   540
ISLIILIMLW QKKPR                                                   555
```

| | | |
|---|---|---|
| SEQ ID NO: 50<br>FEATURE<br>misc_feature | moltype = DNA   length = 1668<br>Location/Qualifiers<br>1..1668<br>note = Synthetic Polynucleotide | |
| source | 1..1668<br>mol_type = other DNA<br>organism = synthetic construct | |
| SEQUENCE: 50 | | |

-continued

```
atggaaaccg acaccttgct cctgtgggtt ctcctgttgt gggtgccggg atcaacggga   60
gctgattaca aggatgacga cgataagtat gaattgatcc aaccctccag tgcgagtgtc  120
actgtcggtg agaccgttaa aataacttgt agcggcgacc aacttccgaa gaactttgct  180
tactggtttc aacaaaagtc agacaagaat atattgcttt tgatatatat ggacaataag  240
agacccagtg ggattccaga gagattttcc ggctcaacct ctggaacaac agccacactt  300
acgatatcag gggcccagcc tgaagacgag gcagcgtact actgcctttc ctcctacgga  360
gataataacg atcttgtgtt cggctccgga acacagctta ccgttctgcg gggaccaaag  420
agcagtccca aagtaaccgt ctttcccca agccccgagg agcttaggac taataaagcg  480
acgctggtct gtcttgtcaa tgactttac cctggctgcc ccacagtgac atggaaggca  540
aatggggcca ctattaacga cggtgtcaag actacgaagc caagcaaaca ggggcaaaac  600
tacatgacaa gcagctactt gagtttgact gcggaccagt ggaagtctca aatagagtt   660
agctgtcaag tcacacatga aggcgagact gttgaaaaat cactctcccc tgcggaatgc  720
ttgggaagtg gtgctacgaa cttctcactg cttaagcaag ctggagatgt tgaggaaaac  780
cctggaccaa tggtgccgtg caccctcctt ttgcttttgg ccgctgcgtt ggctccaacc  840
cagactaggg cagaggttta tcttgttgag tccggaggtg acttggtgca gcctggctct  900
tcccttaagg tctcatgcgc cgcatccggc tttacattct ctgattttg gatgtattgg   960
gttcgccagg ctcctggtaa agggctgaaa tgggtgggca gaatcaagaa catccccaat 1020
aactacgcta cagaatatgc cgactcagtg aggggcgct tcactatatc acgagacgat 1080
tcacggaact ctatttatct gcagatgaac cggttgaggg ttgatgacac cgcgatatat 1140
tattgcacca gagctggcag gtttgaccac tttgactact ggggacaggg tacgatggtg 1200
actgtgagta gcgcaacgac aaccgcacct tcagtgtacc cactcgctcc tgcttgcgac 1260
tccaccacta gcacgacaga caccgtcact ctcggatgtt tggtaaaagg atatttttca 1320
gaacctgtca ccgtttcttg aatagtggc gcattgactt caggtgtcca tacgttcct   1380
tccgtcttgc acagtggact gtactcattg tcatctagtg ttacagtacc gtcctccaca 1440
tggccgaagc agccgataac ttgtaatgtc gcccatccag cctcctccac taaggtggac 1500
aagaaaatag agcctagagc cgtcggccag gacacccagg agttaattgt tgtcccacat 1560
tcacttccat tcaaggtggt cgtgatctct gcgatcctcg cgctcgtcgt tttgacgatc 1620
attagcctca tcatcctcat catgttgtgg cagaaaaagc cccggtaa              1668

SEQ ID NO: 51           moltype = AA  length = 512
FEATURE                 Location/Qualifiers
REGION                  1..512
                        note = Synthetic Polypeptide
source                  1..512
                        mol_type = protein
                        organism = synthetic construct
SEQUENCE: 51
MNFLLLTFIV LPLCSHAKFS IVFPQSQKGN WKNVPSSYHY CPSSSDQNWH NDLLGITMKV   60
KMPKTHKAIQ ADGWMCHAAK WITTCDFRWY GPKYITHSIH SIQPTSEQCK ESIKQTKQGT  120
WMSPGFPPQN CGYATVTDSV AVVVQATPHH VLVDEYTGEW IDSQFPNGKC ETEECETVHN  180
STVWYSDYKV TGLCDATLVD TEITFFSEDG KKESIGKPNT GYRSNYFAYE KGDKVCKMNY  240
CKHAGVRLPS GVWFEFVDQD VYAAAKLPEC PVGATISAPT QTSVDVSLIL DVERILDYSL  300
CQETWSKIRS KQPVSPVDLS YLAPKNPGTG PAFTIINGTL KYFETRYIRI DIDNPIISKM  360
VGKISGSQTE RELWTEWFPY EGVEIGPNGI LKTPTGYKFP LFMIGHGMLD SDLHKTSQAE  420
VFEHPHLAEA PKQLPEEETL FFGDTGISKN PVELIEGWFS SWKSTVVTFF FAIGVFILLY  480
VVARIVIAVR YRYQGSNNKR IYNDIEMSRF RK                                512

SEQ ID NO: 52           moltype = DNA  length = 1539
FEATURE                 Location/Qualifiers
misc_feature            1..1539
                        note = Synthetic Polynucleotide
source                  1..1539
                        mol_type = other DNA
                        organism = synthetic construct
SEQUENCE: 52
atgaactttc tgctgctcac gtttatcgta ctcccgttgt gctctcatgc gaaattttca   60
atagtctttc ctcagtccca gaagggaat tggaaaaatg ttccctccag ttaccactat   120
tgtccctcct cctctgacca aaactggcac aatgacttgc tcgggattac aatgaaagta  180
aagatgccga aaaccataa gccatacag gcggatgggt ggatgtgtca cgctgcgaag   240
tggatcacta catgcgattt ccggtggtat ggccctaagt acattacaca ctctatccat  300
agcatacagc cgacatcaga gcaatgcaaa gagagtatta aacagaccaa acaagggaca  360
tggatgagcc ctggctttcc acctcagaat tgtgggtacg cgaccgtcac ggatagtgtc  420
gctgttgtgg tgcaggccac gccacatcac gtactcgtag atgaatatac tggtgaatgg  480
atcgactccc aatttcccga tgggaaatgt gagacgaaag agtgcgaaac agtgcataac  540
tcaaccgttt ggtattccga ttacaaggtt actggtcttt gcgacgccac cctcgtggat  600
accgagatca cgttttttag tgaggatgcc aagaaagagt caataggcaa acctaatact  660
ggctaccgga gtaactattt cgcttacgag aagggtgaca aggtatgtaa aatgaactat  720
tgcaagcatg cgggagtgcg actccccagt ggggtatggt tcgaatttgt tgaccaagac  780
gtatacgccg ctgcgaagtt gccagaatgc ccgtaggccg cgaccattc agcacctacc   840
caaacgtccg ttgacgtctc cttgatactg gatgtagagc gaatcctgga ctacagtctc  900
tgccaggaaa cgtggtcaaa aataagaagt aagcagccag tttcaccgt ggatctgtct   960
tatctggcgc aaaaaaccc gggcacgggc ctgcttttta ccataattaa cggaacgctt 1020
aaatactttg aaacccgcta cattagaatc gatatagaca atcctattat cagcaagatg 1080
gtagggaaga tatctgggtc tcaaacggag cgagaattgt ggacggagtg gttccctat   1140
gagggagtga aaattgggcc caacgggatc ctcaagaccc caacgggtta caagttccct 1200
ctgtttatga tcgccatgg catgttggac agtgacttgc acaaaacatc tcaggcagag 1260
gttttcgaac atccacattt ggcggaggcg cccaagcaac ttccagaaga gaaactctc  1320
ttctttggag atacaggcat ttcaaaaaat cctgtagaac tgatagaagg tggttctct   1380
tcctggaaat caacggttgt cacgtttttc tttgcaatag gcgtatttat actcctgtac 1440
```

```
gtcgtagccc gcattgtgat cgcagtacga tacagatacc agggcagtaa caataaacgc  1500
atatataatg acatcgaaat gtcaaggttc cgaaagtga                         1539

SEQ ID NO: 53           moltype = AA  length = 512
FEATURE                 Location/Qualifiers
REGION                  1..512
                        note = Synthetic Polypeptide
source                  1..512
                        mol_type = protein
                        organism = synthetic construct
SEQUENCE: 53
MNFLLLTFIV LPLCSHAKFS IVFPQSQKGN WKNVPSSYHY CPSSSDQNWH NDLLGITMKV   60
KMPQTHKAIQ ADGWMCHAAK WITTCDFRWY GPKYITHSIH SIQPTSEQCK ESIKQTKQGT  120
WMSPGFPPQN CGYATVTDSV AVVVQATPHH VLVDEYTGEW IDSQFPNGKC ETEECETVHN  180
STVWYSDYKV TGLCDATLVD TEITFFSEDG KKESIGKPNT GYRSNYFAYE KGDKVCKMNY  240
CKHAGVRLPS GVWFEFVDQD VYAAAKLPEC PVGATISAPT QTSVDVSLIL DVERILDYSL  300
CQETWSKIRS KQPVSPVDLS YLAPKNPGTG PAFTIINGTL KYFETRYIRI DIDNPIISKM  360
VGKISGSQTE AELWTEWFPY EGVEIGPNGI LKTPTGYKFP LFMIGHGMLD SDLHKTSQAE  420
VFEHPHLAEA PKQLPEEETL FFGDTGISKN PVELIEGWFS SWKSTVVTFF FAIGVFILLY  480
VVARIVIAVR YRYQGSNNKR IYNDIEMSRF RK                                512

SEQ ID NO: 54           moltype = DNA  length = 1539
FEATURE                 Location/Qualifiers
misc_feature            1..1539
                        note = Synthetic Polynucleotide
source                  1..1539
                        mol_type = other DNA
                        organism = synthetic construct
SEQUENCE: 54
atgaactttc tgctgctcac gtttatcgta ctcccgttgt gctctcatgc gaaattttca   60
atagtctttc ctcagtccca gaaagggaat tggaaaaatg ttccctccag ttaccactat  120
tgtccctcct cctctgacca aaactggcac aatgacttgc tcgggattac aatgaaagta  180
aagatgccgc agacccataa agccatacag gcggatgggt ggatgtgtca cgctgcgaag  240
tggatcacta catgcgattt ccggtggtat ggccctaagt acattacaca ctctatccat  300
agcatacagc cgacatcaga gcaatgcaaa gagagtatta aacagaccaa acaagggaca  360
tggatgagcc ctggctttcc acctcagaat tgtgggtacg cgaccgtcac ggatagtgtc  420
gctgttgtgg tgcaggccac gccacatcac gtactcgtag atgaatatac tggtgaatgg  480
atcgactccc aattcccgaa tgggaaatgt gagacggaag agtgcgaaac agtgcataac  540
tcaaccgttt ggtattccga ttacaaggtt actggtcttt gcgacgccac cctcgtggat  600
accgagatca cgttttttag tgaggatggc aagaaagagt caataggcaa acctaatact  660
ggctaccgga gtaactattt cgcttacgag aagggtgaca aggtatgtaa aatgaactat  720
tgcaagcatg cgggagtgcg actccccagt ggggtatggt tcgaatttgt tgaccaagac  780
gtatacgccg ctgcgaagtt gccagaatgc cccgtaggcg cgaccatttc agcaccctacc  840
caaacgtccg ttgacgtctc cttgatactg gatgtagagc gaatcctgga ctacagtctc  900
tgccaggaaa cgtggtcaaa aataagaagt aagcagccag tttcacccgt ggatctgtct  960
tatctggcgc aaaaaaccc gggcacgggc cctgcttta ccataattaa cggaacgctt  1020
aaatacttcg aaacccgcta cattagaatc gatatagaca atcctattat cagcaagatg  1080
gtagggaaga tatctgggtc tcaaacggag gccgaattgt ggacggagtg gttcccttat  1140
gagggagtgg aaatttgggcc caacgggatc ctcaagaccc caacgggtta caagttccct  1200
ctgtttatga tcggccatgg catgttggac agtgacttgc acaaaacatc tcaggcagag  1260
gttttcgaac atccacattt ggcggaggcg cccaagcaac ttccagaaga aaaactctc  1320
ttctttggag atacaggcat ttcaaaaaat cctgtagaac tgatagaagg gtggttctct  1380
tcctggaaat caacgttgt cacgtttttc tttgcaatag gcgtatttat actcctgtac  1440
gtcgtagccc gcattgtgat cgcagtacga tacagatacc agggcagtaa caataaacgc  1500
atatataatg acatcgaaat gtcaaggttc cgaaagtga                         1539
```